United States Patent
Morris et al.

(10) Patent No.: US 12,064,601 B2
(45) Date of Patent: *Aug. 20, 2024

(54) METHODS FOR PROVIDING AN ALERT OR AN ALARM TO A USER OF A MOBILE COMMUNICATIONS DEVICE

(71) Applicant: Dexcom, Inc., San Diego, CA (US)

(72) Inventors: Gary A. Morris, San Marcos, CA (US); Scott M. Belliveau, San Diego, CA (US); Esteban Cabrera, Jr., San Diego, CA (US); Anna Leigh Davis, San Diego, CA (US); Rian W. Draeger, San Diego, CA (US); Laura J. Dunn, San Diego, CA (US); Timothy Joseph Goldsmith, San Diego, CA (US); Hari Hampapuram, Beaverton, OR (US); Christopher Robert Hannemann, San Diego, CA (US); Apurv Ullas Kamath, San Diego, CA (US); Katherine Yerre Koehler, Solana Beach, CA (US); Patrick Wile McBride, San Diego, CA (US); Michael Robert Mensinger, San Diego, CA (US); Francis William Pascual, San Diego, CA (US); Philip Mansiel Pellouchoud, San Diego, CA (US); Nicholas Polytaridis, San Diego, CA (US); Philip Thomas Pupa, San Diego, CA (US); Kevin Shoemaker, San Diego, CA (US); Brian Christopher Smith, San Diego, CA (US); Benjamin Elrod West, San Diego, CA (US); Atiim Joseph Wiley, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/465,839

(22) Filed: Sep. 12, 2023

(65) Prior Publication Data

US 2023/0414873 A1 Dec. 28, 2023

Related U.S. Application Data

(63) Continuation of application No. 18/065,943, filed on Dec. 14, 2022, now Pat. No. 11,826,549, which is a
(Continued)

(51) Int. Cl.
*A61M 5/172* (2006.01)
*A61B 5/00* (2006.01)
(Continued)

(52) U.S. Cl.
CPC ....... *A61M 5/1723* (2013.01); *A61B 5/14532* (2013.01); *A61B 5/4839* (2013.01);
(Continued)

(58) Field of Classification Search
CPC ........ A61M 5/1723; A61M 2205/3584; A61M 2205/50; A61M 2205/502;
(Continued)

(56) References Cited

U.S. PATENT DOCUMENTS

| 3,014,603 A | 12/1961 | Taubmann |
|---|---|---|
| 7,624,028 B1 | 11/2009 | Brown |

(Continued)

FOREIGN PATENT DOCUMENTS

| JP | 2016539760 A | 12/2016 |
|---|---|---|
| JP | 2017525451 A | 9/2017 |

(Continued)

OTHER PUBLICATIONS

Bernet Palacin V., et al., "GlucoServer. Design, Development and Exploitation Plan of a Health Monitoring Network," University Polytechnic of Catalonia (UPC), Jun. 14, 2011,92 pages, Retrieved from the Internet: URL: https://upcommons.upc.edU/bitstream/handle/2099.1/13634/PFC.pdf?sequence=1.

(Continued)

*Primary Examiner* — Kambiz Zand
*Assistant Examiner* — Aubrey H Wyszynski
(74) *Attorney, Agent, or Firm* — PATTERSON + SHERIDAN, LLP

(57) ABSTRACT

Methods, devices and systems are disclosed for inter-app communications between software applications on a mobile
(Continued)

communications device. In one aspect, a computer-readable medium on a mobile computing device comprising an inter-application communication data structure to facilitate transitioning and distributing data between software applications in a shared app group for an operating system of the mobile computing device includes a scheme field of the data structure providing a scheme id associated with a target software app to transition to from a source software app, wherein the scheme id is listed on a scheme list stored with the source software app; and a payload field of the data structure providing data and/or an identification where to access data in a shared file system accessible to the software applications in the shared app group, wherein the payload field is encrypted.

16 Claims, 27 Drawing Sheets

Related U.S. Application Data continuation of application No. 17/202,845, filed on Mar. 16, 2021, which is a continuation-in-part of application No. 15/475,010, filed on Mar. 30, 2017, now Pat. No. 10,980,941, which is a continuation of application No. 15/474,886, filed on Mar. 30, 2017, now Pat. No. 10,596,318.

(60) Provisional application No. 62/370,182, filed on Aug. 2, 2016, provisional application No. 62/315,948, filed on Mar. 31, 2016.

(51) Int. Cl.

| | |
|---|---|
| *A61B 5/145* | (2006.01) |
| *G06F 9/54* | (2006.01) |
| *G06F 16/22* | (2019.01) |
| *G06F 16/955* | (2019.01) |
| *G06F 21/60* | (2013.01) |
| *G08B 21/04* | (2006.01) |
| *G08B 25/08* | (2006.01) |
| *G16H 10/60* | (2018.01) |
| *G16H 20/17* | (2018.01) |
| *G16H 40/63* | (2018.01) |
| *H04L 9/06* | (2006.01) |
| *H04L 9/08* | (2006.01) |
| *H04L 9/14* | (2006.01) |
| *H04L 9/30* | (2006.01) |
| *H04L 9/40* | (2022.01) |
| *H04M 1/72409* | (2021.01) |
| *H04M 1/72412* | (2021.01) |
| *H04W 12/084* | (2021.01) |

(52) U.S. Cl.
CPC ............ *A61B 5/7405* (2013.01); *A61B 5/742* (2013.01); *G06F 9/54* (2013.01); *G06F 9/546* (2013.01); *G06F 16/2228* (2019.01); *G06F 16/955* (2019.01); *G06F 21/606* (2013.01); *G08B 21/0453* (2013.01); *G08B 25/08* (2013.01); *G16H 10/60* (2018.01); *G16H 20/17* (2018.01); *G16H 40/63* (2018.01); *H04L 9/0637* (2013.01); *H04L 9/0822* (2013.01); *H04L 9/0833* (2013.01); *H04L 9/0861* (2013.01); *H04L 9/0891* (2013.01); *H04L 9/14* (2013.01); *H04L 9/30* (2013.01); *H04L 63/0428* (2013.01); *H04M 1/72409* (2021.01); *H04W 12/084* (2021.01); *A61M 2205/3584* (2013.01); *A61M 2205/50* (2013.01); *A61M 2205/502* (2013.01); *A61M 2230/201* (2013.01); *H04L 2209/80* (2013.01); *H04M 1/724095* (2022.02); *H04M 1/72412* (2021.01)

(58) Field of Classification Search
CPC ......... A61M 2230/201; A61B 5/14532; A61B 5/4839; A61B 5/7405; A61B 5/742; G06F 9/54; G06F 9/546; G06F 16/2228; G06F 16/955; G06F 21/606; G08B 21/0453; G08B 25/08; G16H 10/60; G16H 20/17; G16H 40/63; H04L 9/0637; H04L 9/0822; H04L 9/0833; H04L 9/0861; H04L 9/0891; H04L 9/14; H04L 9/30; H04L 63/0428; H04L 2209/80; H04M 1/72409; H04M 1/724095; H04M 1/72412; H04W 12/084
USPC ........................................................ 715/771
See application file for complete search history.

(56) References Cited

U.S. PATENT DOCUMENTS

| | | |
|---|---|---|
| 8,077,634 B2 | 12/2011 | Maggenti et al. |
| 8,424,007 B1 | 4/2013 | Hernacki et al. |
| 8,494,046 B2 | 7/2013 | Yang |
| 8,839,266 B1 | 9/2014 | Partridge et al. |
| 10,596,318 B2 | 3/2020 | Morris et al. |
| 10,980,941 B2 | 4/2021 | Morris et al. |
| 2003/0012149 A1 | 1/2003 | Maggenti et al. |
| 2005/0080526 A1 | 4/2005 | Williams et al. |
| 2007/0047392 A1 | 3/2007 | Parkinson et al. |
| 2007/0190991 A1 | 8/2007 | Cargille |
| 2007/0240166 A1 | 10/2007 | Marappan |
| 2008/0033960 A1* | 2/2008 | Banks ................... H04L 9/0894 707/999.009 |
| 2008/0215883 A1 | 9/2008 | Fok et al. |
| 2008/0272910 A1 | 11/2008 | Anderson |
| 2008/0309485 A1 | 12/2008 | Raduchel |
| 2009/0099864 A1* | 4/2009 | Cronrath ................ G16H 10/40 705/2 |
| 2009/0318792 A1 | 12/2009 | Fennell et al. |
| 2010/0016700 A1* | 1/2010 | Sieh ........................ G16H 15/00 726/16 |
| 2010/0317952 A1 | 12/2010 | Budiman et al. |
| 2011/0025499 A1 | 2/2011 | Hoy et al. |
| 2011/0119087 A1 | 5/2011 | Drucker et al. |
| 2011/0193704 A1 | 8/2011 | Harper et al. |
| 2012/0035958 A1 | 2/2012 | Rhine-Pallas et al. |
| 2012/0165639 A1 | 6/2012 | Engelhardt et al. |
| 2012/0191362 A1 | 7/2012 | Schmitt et al. |
| 2012/0221886 A1* | 8/2012 | Barsness ............. G06F 11/1482 714/4.2 |
| 2012/0232520 A1* | 9/2012 | Sloan ..................... G16H 20/17 604/504 |
| 2012/0245447 A1 | 9/2012 | Karan et al. |
| 2012/0266251 A1* | 10/2012 | Birtwhistle ........... H04W 12/50 726/26 |
| 2013/0035865 A1 | 2/2013 | Mayou et al. |
| 2013/0130215 A1 | 5/2013 | Bock et al. |
| 2013/0172692 A1 | 7/2013 | Choi et al. |
| 2014/0012117 A1 | 1/2014 | Mensinger et al. |
| 2014/0012511 A1 | 1/2014 | Mensinger et al. |
| 2014/0068273 A1 | 3/2014 | Sobel et al. |
| 2014/0068593 A1 | 3/2014 | McErlane et al. |
| 2014/0088393 A1 | 3/2014 | Bernstein et al. |
| 2014/0095874 A1 | 4/2014 | Desai et al. |
| 2014/0118166 A1 | 5/2014 | Hampapuram et al. |
| 2014/0173625 A1 | 6/2014 | Kumar et al. |
| 2014/0177839 A1 | 6/2014 | Wagner et al. |
| 2014/0180711 A1 | 6/2014 | Kamen et al. |
| 2014/0181842 A1 | 6/2014 | Kim et al. |
| 2014/0184422 A1 | 7/2014 | Mensinger et al. |
| 2014/0187890 A1 | 7/2014 | Mensinger et al. |

(56) References Cited

U.S. PATENT DOCUMENTS

| | | |
|---|---|---|
| 2014/0188398 A1 | 7/2014 | Cohen et al. |
| 2014/0195639 A1 | 7/2014 | Kamen et al. |
| 2014/0221911 A1 | 8/2014 | Van Wieren et al. |
| 2014/0275852 A1 | 9/2014 | Hong et al. |
| 2014/0282003 A1 | 9/2014 | Gruber et al. |
| 2014/0325065 A1* | 10/2014 | Birtwhistle ............ H04L 47/70 709/225 |
| 2014/0364711 A1 | 12/2014 | Ismail et al. |
| 2015/0123813 A1 | 5/2015 | Hernandez-Rosas et al. |
| 2015/0173674 A1 | 6/2015 | Hayes et al. |
| 2015/0222637 A1 | 8/2015 | Hung et al. |
| 2015/0244775 A1 | 8/2015 | Vibhor et al. |
| 2015/0282767 A1 | 10/2015 | Stivoric et al. |
| 2015/0289823 A1 | 10/2015 | Rack-Gomer et al. |
| 2015/0319143 A1 | 11/2015 | Kim et al. |
| 2015/0335272 A1 | 11/2015 | Natale et al. |
| 2016/0066843 A1 | 3/2016 | Mensinger et al. |
| 2016/0081597 A1 | 3/2016 | Bhavaraju et al. |
| 2016/0084869 A1 | 3/2016 | Yuen et al. |
| 2016/0117520 A1 | 4/2016 | Safa |
| 2016/0147942 A1 | 5/2016 | Chmura |
| 2016/0157733 A1 | 6/2016 | Gil |
| 2016/0171871 A1 | 6/2016 | Zhang |
| 2016/0232318 A1 | 8/2016 | Mensinger et al. |
| 2016/0256063 A1 | 9/2016 | Friedman et al. |
| 2016/0262707 A1 | 9/2016 | DeVries |
| 2016/0287142 A1 | 10/2016 | Han et al. |
| 2016/0335002 A1 | 11/2016 | Malkin |
| 2017/0018886 A1 | 1/2017 | Juds et al. |
| 2017/0100072 A1 | 4/2017 | Heikenfeld |
| 2017/0216524 A1 | 8/2017 | Haider et al. |
| 2017/0221344 A1 | 8/2017 | Cox et al. |
| 2017/0286194 A1 | 10/2017 | Morris et al. |
| 2017/0286614 A1 | 10/2017 | Morris et al. |
| 2017/0329917 A1 | 11/2017 | McRaith et al. |
| 2017/0372017 A1 | 12/2017 | Steffen |
| 2018/0005332 A1* | 1/2018 | Testa ............... G16H 10/60 |
| 2018/0137939 A1 | 5/2018 | Steiger |
| 2018/0199890 A1 | 7/2018 | Hayter et al. |
| 2018/0303417 A1 | 10/2018 | Mensinger et al. |
| 2019/0088353 A1* | 3/2019 | Humphrys ............ G16H 40/63 |
| 2020/0097777 A1 | 3/2020 | Goto et al. |
| 2020/0196922 A1* | 6/2020 | Kamath ................ G16H 40/67 |
| 2020/0203012 A1 | 6/2020 | Kamath et al. |

FOREIGN PATENT DOCUMENTS

| | | |
|---|---|---|
| KR | 20120006632 A | 1/2012 |
| WO | 2015017996 A1 | 2/2015 |
| WO | 2015066051 A2 | 5/2015 |
| WO | 2016019192 A1 | 2/2016 |
| WO | 2017011346 A1 | 1/2017 |
| WO | 2017116692 A1 | 7/2017 |
| WO | 2019126047 A1 | 6/2019 |

OTHER PUBLICATIONS

Chang P.S., et aL, "Secure Intra-Device Communication Protocol Between Applications on a Smart Device," 14th Annual Conference on Privacy, Security and Trust (PST), IEEE, 2016, 5 pages.

Fletcher L., et al., "Feasibility of an Implanted, Closed-Loop, Blood-Glucose Control Device," Immunology 230, 2001, pp. 1-31.

International Preliminary Report on Patentability for Application No. PCT/US2017/025170 dated Oct. 11, 2018, 13 pages.

International Search Report and Written opinion for Application No. PCT/US2017/025170 dated Jul. 21, 2017, 14 pages.

International Search Report and Written Opinion for Application No. PCT/US2019/66958 dated Apr. 21, 2020, 12 pages.

Keith-Hynes P. et al., "DiAs User Interface: A Patient-Centric Interface for Mobile Artificial Pancreas Systems," Journal of Diabetes Science and Technology, Nov. 2013, vol. 7, No. 6, pp. 1416-1426, Retrieved from the Internet: URL: https://journals.sagepub.com/doi/pdf/10.1177/193229681300700602.

Shah V.N., et al., "Managing Diabetes in the Digital Age," Clinical Diabetes and Endocrinology, 2015, vol. 1, No. 16, 7 pages, Retrieved from the Internet: URL: https://link.springer.com/content/pdf/10.1186/s40842-015-0016-2.pdf?pdf=button.

Wood B.P., "Software and Hardware Support for Data-Race Exceptions," Dissertation, University of Washington, 2014, 188 pages, Retrieved from the Internet: URL: https://digital.lib.washington.edu/researchworks/bitstream/handle/1773/26022/Wood_washington_0250E_13670.pdf?sequence=1.

International Search Report and Written Opinion for Application No. PCT/US2023/020800 dated Aug. 24, 2023, 19 pages.

* cited by examiner

METHODS FOR PROVIDING AN ALERT OR AN ALARM TO A USER OF A MOBILE COMMUNICATIONS DEVICE

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 18/065,943, filed Dec. 14, 2022, which is a continuation of U.S. application Ser. No. 17/202,845, filed Mar. 16, 2021, which is a continuation of U.S. application Ser. No. 15/475,010, filed Mar. 30, 2017, and now U.S. Pat. No. 10,980,941, which is a continuation of U.S. application Ser. No. 15/474,886, filed Mar. 30, 2017 and now U.S. Pat. No. 10,596,318, which claims the benefit of U.S. Provisional Application No. 62/315,948, filed Mar. 31, 2016 and U.S. Provisional Application No. 62/370,182 filed Aug. 2, 2016. Each of the aforementioned applications is incorporated by reference herein in its entirety, and each is hereby expressly made a part of this specification.

TECHNICAL FIELD

The present disclosure relates to a continuous glucose monitor system for sensing glucose levels and wirelessly transmitting glucose data to a mobile computing device, and controlling the display and distribution of that data on the mobile computing device.

BACKGROUND

Continuous glucose monitors have been increasing in popularity as an easy way to monitor glucose levels. In the past, patients sample their blood glucose levels several times throughout a day, such as in the morning, around lunch, and in the evening. The levels can be measured by taking a small blood sample of the patient and measuring the glucose levels with a test strip or glucose meter. This technique, however, has drawbacks because patients would prefer to not have to take a blood sample, and users do not know what their blood glucose levels are throughout the day between the samples.

One potentially dangerous timeframe is at night because a patient's glucose levels can fall dangerously low during sleep. As a result, continuous glucose monitors have gained popularity by providing a sensor that continuously measures glucose levels of a patient and transmits the measured glucose levels wirelessly to a display. This allows the patient or patient's caregiver to monitor the patient's glucose levels throughout the day and even set alarms for when glucose levels reach a predefined level or experience a defined change.

Initially, continuous glucose monitors wirelessly transmitted data relating to glucose levels to a dedicated display. The dedicated display is a medical device designed to display glucose levels, trending patterns, and other information for a user. However, with the increasing popularity of smart phones and software applications (apps) executing on smart phones, some users prefer to avoid having to carry a dedicated display. Instead, some users prefer to monitor their glucose levels using a dedicated software app executing on their mobile computing device, such as a smart phone, tablet or wearable device like a smartwatch or smartglasses.

SUMMARY

Certain embodiments of the present disclosure generally relate to techniques for managing data communication between software apps on a computing device.

In an example embodiment, a method for facilitating inter-app communications between software applications includes receiving, by a first software app on a mobile computing device, a first instruction to transition from the first software app to a second software app on the mobile computing device; generating a data structure to initiate the transition and provide a data payload to the second software app; and providing, by the first software app, the data structure to cause initiation of the second software app in a foreground mode of the mobile computing device. In some implementations of the method, for example, the method further includes generating, by the first software app, the first instruction based on a user selection of an identifier of the second software app (e.g., icon and/or text associated with the second software app) presented on a display screen of the first software app. In some implementations of the method, for example, the generating the data structure includes (i) populating a first field of the data structure with a scheme id associated with the second software app, (ii) populating a second field of the data structure with the data payload, and (iii) encrypting at least the second field of the data structure.

In an example embodiment, a method for initiating inter-application communication between software applications includes designating software apps to a shared app group for an operating system of a mobile computing device, the shared app group including a first software app and one or more preapproved software apps, the first software app stored on a computer-readable medium of the mobile computing device and comprising instructions executable by a processor of the mobile computing device; establishing an inter-app data communication architecture on the mobile computing device to link the first software app and a second software app included among the preapproved software apps, in which the inter-app data communication architecture includes a data structure including (i) a scheme field to identify a software app from a scheme list and (ii) a payload field that is encrypted and includes data and/or an identification where to access data in a shared file system of the shared app group; generating a public/private key pair for encryption and decryption of the payload field of the data structure by: providing a first public key for the first software app in a shared keychain of the shared app group, providing a first private key for the first software app in a first private keychain accessible to the first software app, providing a second public key for the second software app in the shared keychain, and providing a second private key for the second software app in a second private keychain accessible to the second software app; and generating a database key for encryption of a shared database in the shared file system by producing a database key in the first private keychain accessible to the first software app, and creating an encrypted database key by encrypting a copy of the database key with the second public key, in which the encrypted database key is stored in the shared keychain.

In an example embodiment, a method is disclosed for inter-application communication between software applications in a shared app group for an operating system of a mobile computing device, in which the software applications are stored on a computer-readable medium of the mobile computing device and each comprise their own instructions executable by a processor of the mobile computing device. The method includes operating a first software app in a foreground on the mobile computing device; generating a data structure to initiate a transition from the first software app to a second software app in the foreground, the generating including (i) populating a scheme field of the data structure with a scheme id associated with the second software app from a scheme list stored with the first software app, (ii) populating a payload field of the data structure with data and/or an identification where to access data in a shared file system accessible to the software applications in the shared app group, and (iii) encrypting at least the payload field of the data structure; providing the data structure to cause initiation of the second software app to the foreground; and providing at least the encrypted payload field of the data structure for the second software app.

In an example embodiment, a system for managing care of diabetes includes a continuous glucose monitoring (CGM) device operable to obtain glucose measurements and wirelessly transmit the glucose measurements to an external device; an insulin delivery device operable to inject a dose of insulin; and a mobile computing device, comprising a wireless receiver to receive the glucose measurements, a memory to store data including the received glucose measurements, a processor to process the data, a first software application pertaining to the CGM device and a second software application pertaining to the insulin delivery device. The first software application includes instructions stored in the memory which, when executed by the processor, generate a data structure to initiate a transition from the first software app to the second software app in the foreground, provide the data structure to cause initiation of the second software app to the foreground, and provide at least the encrypted payload field of the data structure for the second software app. The second software application includes instructions stored in the memory which, when executed by the processor, receive the at least encrypted payload field. In some implementations of the system, for example, the instructions of the first software application to generate the data structure includes instructions to populate a scheme field of the data structure with a scheme id associated with the second software app from a scheme list stored with the first software app, populate a payload field of the data structure with data and/or an identification where to access data in a shared file system accessible to the software applications in a shared app group for an operating system of the mobile computing device, and encrypt at least the payload field of the data structure. In some implementations of the system, for example, the payload field of the data structure is encrypted by a public/private key pair. In some implementations, for example, the public/private key pair includes a first public key for the first software app stored in a shared keychain of the shared app group, a first private key for the first software app in a first private keychain accessible to the first software app, a second public key for the second software app in the shared keychain, and a second private key for the second software app in a second private keychain accessible to the second software app. In some implementations of the system, for example, the shared file system includes an encrypted shared database that is accessible to the first software app using a master database key in a first private keychain accessible to the first software app and accessible to the second software app using an asymmetric encrypted database key in a shared keychain of the shared app group. In some implementations, for example, the asymmetric encrypted database key is an encrypted copy of the master database key encrypted using a second public key for the second software app in the shared keychain and decrypted using a second private key for the second software app in a second private keychain accessible to the second software app.

In an example embodiment, a computer-readable medium on a mobile computing device includes instructions which, when executed by a processor of the mobile computing device, perform a method for transitioning and distributing data between software applications in a shared app group for an operating system of a mobile computing device, in which the method includes generating a data structure to initiate a transition from a first software app operating in the foreground to a second software app to operate in the foreground, the generating including (i) populating a scheme field of the data structure with a scheme id associated with the second software app from a scheme list stored with the first software app, (ii) populating a payload field of the data structure with data and/or an identification where to access data in a shared file system accessible to the software applications in the shared app group, and (iii) encrypting at least the payload field of the data structure; providing the data structure to cause initiation of the second software app to the foreground; and providing at least the encrypted payload field of the data structure for the second software app.

In an example embodiment, a computer-readable medium on a mobile computing device is provided comprising an inter-application communication data structure to facilitate transitioning and distributing data between software applications in a shared app group for an operating system of the mobile computing device. The inter-application communication data structure includes a scheme field of the data structure providing a scheme id associated with a target software app to transition to, from a source software app, where the scheme id is listed on a scheme list stored with the source software app. A payload field of the data structure provides data and/or an identification where to access data in a shared file system accessible to the software applications in the shared app group. The payload field is encrypted. In some implementations of the computer-readable medium, for example, the payload field of the data structure is encrypted using a public/private key pair comprising a first public key for the source software app stored in a shared keychain of the shared app group, a first private key for the source software app in a first private keychain accessible to the source software app, a second public key for the target software app in the shared keychain, and a second private key for the target software app in a second private keychain accessible to the target software app.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
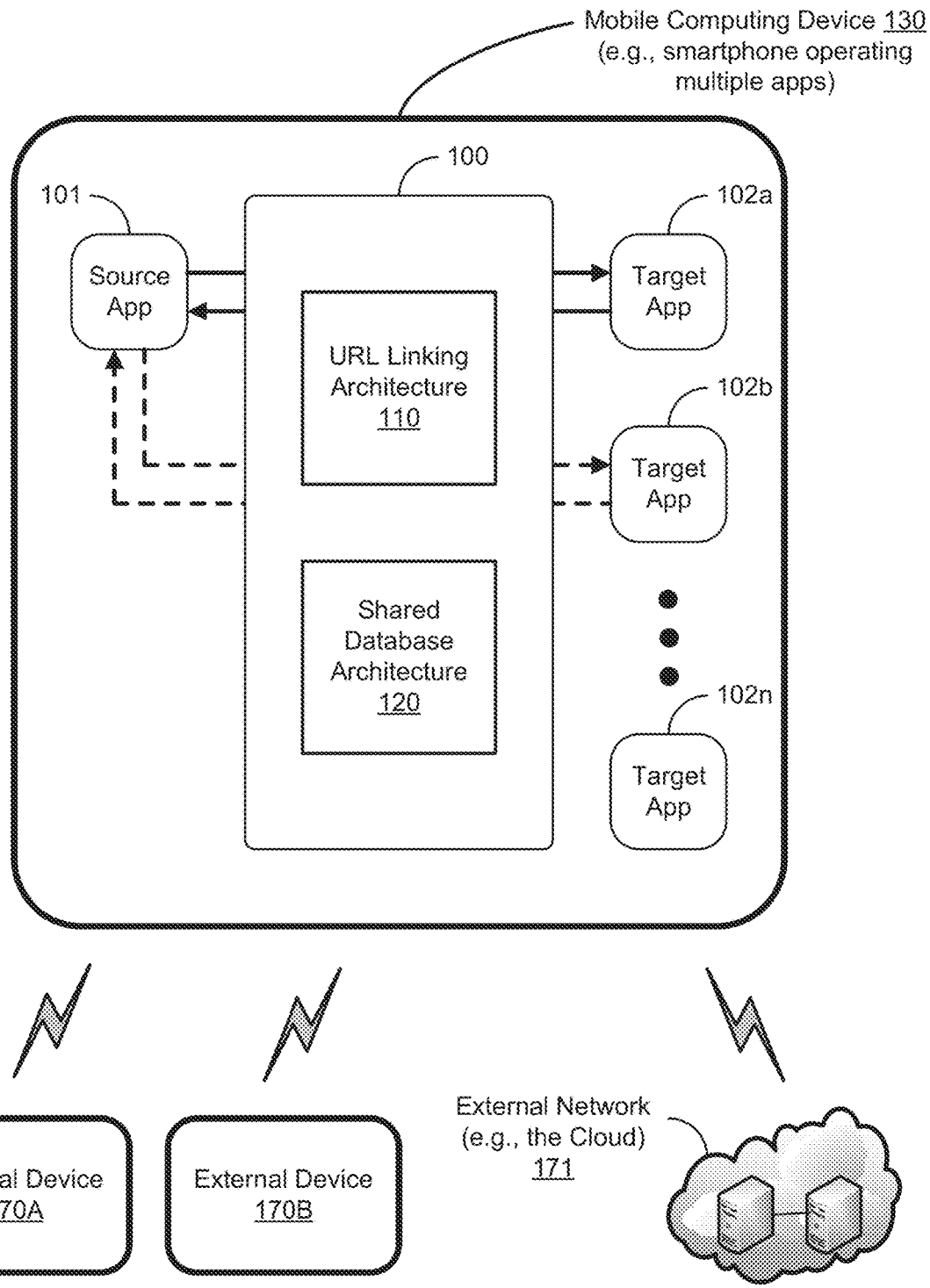
FIG. 1A is a diagram showing an inter-app communications architecture on a computing device to facilitate data distribution and inter-app transitions between a source app and one or more target apps linked to the source app in accordance with embodiments of the inter-app communications of the present technology.

Illustrative embodiments described in the present disclosure relate to techniques for controlling the protection and distribution of data between independent software applications (apps) on a computing device so that such data can be used in an intended manner. Some embodiments control which apps can receive data or select portions of data, provide security measures for maintaining the privacy of the data for storage and transfer between the apps, and/or manage the processing and/or display of the data for the presentation of the data to an end user. Embodiments therefore provide users with the convenience of accessing different yet related forms of data, such as glucose and insulin data, on a single app on their computing device, such as a smart phone, while maintaining security and privacy of their data between the applications on the device. In accordance with some implementations of the disclosed technology, a specialized architecture is provided that integrates two or more apps on the back end for managing inter-app transition and data sharing and flow, e.g., which can provide a homogenized end-user interface and experience on the front end. In some implementations, the inter-app communications architecture may be applied to linking and integrating software applications operable on a mobile computing device, e.g., such as a smartphone, tablet, smartwatch, etc., which have a potential relationship or similarity in their content, accessibility to data, or intended use. While various embodiments and implementations of the inter-app communications architecture are described in the present disclosure for mobile computing devices, the inter-app communications architecture may also be applied on non-mobile computing devices, e.g., such as desktop, laptop and network computers (e.g., servers).

With rapid growth of patient use of personal and wearable medical devices and capabilities to display and store medical data on and via the medical devices and remote servers in communication over a network such as the Internet (e.g., referred to as the Cloud), there are increasing challenges in secure and controlled management of patients' medical data. In particular, many patients may use more than one medical device to manage their care for one or multiple conditions. For example, one medical device may be used to monitor biomedical analytes or signals associated with a disease or medical condition, and another device may be used to determine and provide or recommend the course of treatment for the disease or medical condition. In both cases, medical data is generated by each device that is likely stored by the respective medical device, e.g., on the medical device and/or on another user device like a smartphone, and/or on the Cloud. Yet, there are challenges in allowing data from one medical device to be shared or provided to the other. In some cases, access to the other device's medical data can be used to enhance the functionality and capability of the first medical device, and vice versa. Providing each device's respective medical data to a third-party source, e.g., such as a database on the Cloud, poses several challenges to maintaining security and preventing breaches, as well as maintaining persistent communication channels to ensure continuous and consistent access.

An example for patient use of multiple medical device includes diabetes management using a glucose sensor device, e.g., such as a single-point glucose meter or a continuous glucose monitor, and an insulin delivery device, e.g., such as an insulin pump or pen. Continuous glucose monitor (CGM) devices have been increasing in popularity as an easy and effective way for a diabetic patient to autonomously and continuously monitor his/her glucose levels and display the monitored glucose data in real time, as well as generate and track a variety of other data relating to glucose levels. An insulin pump is a device to at least partially automate the delivery of insulin to balance glucose levels in a safe range, and typically includes a cartridge of insulin (e.g., fast-acting insulin or slow-acting insulin), a controller to set a precise insulin dose to be delivered, and a motor to push the insulin from the cartridge into the body through a thin plastic tube called an infusion set. An insulin pen is a device for the diabetic patient user to manually deliver insulin to their body, e.g., typically by dialing a dose of insulin stored in a cartridge of the pen and depressing a plunger to push the insulin through a needle the patient has inserted into their body. Many recent insulin pen devices are beginning to include electronics to automate certain features, e.g., such as dialing a dose. In general, these devices can acquire and/or generate medical data that is valuable, if not critical, to inform the diabetic patient of his/her condition.

Distributing this information throughout a system and to other devices, systems and/or applications creates challenges associated with protecting patient confidentiality. The glucose level data and associated data and diagnostic information may be confidential (and for some type of associated data, also proprietary) and inappropriate for reproduction to additional devices, systems and applications. Because additional devices, systems and applications, at least in some implementations, should not have access to all of the data, there is a need for a way to control the access and distribution of the medical data from any or each of these devices to facilitate appropriate data sharing and use. Therefore, there is a need for a way to protect medical data that ensures patient confidentiality while providing certain medical data to authorized devices, systems and/or applications to enhance the patient's capabilities to manage their disease or medical condition.

Moreover, conventional means for distributing data among and between multiple medical and/or health-related devices (e.g., Fitbit®, food or exercise tracking apps, etc.) include providing and storing such data on the Cloud. While many cloud-based data management solutions include adequate security measures to protect the data from breach, such solutions require a communication between the medical and/or health-related devices through a network connection. For example, while some devices in a cloud-based data distribution architecture should be allowed to access some of the data, others should not be provided access to that data. There may be a great number of other devices or software applications that access data stored by the cloud server, which may complicate the level of classification of the medical device and put further burden on the medical device manufacturers to comply with regulations, thereby increasing costs. For example, a medical device that provides its medical data to such cloud-based systems may have to meet additional criteria to obtain regulatory approval as a medical device. And once approved, changes to the system may require further regulatory approval, which can be a timely and costly process.

Also, in many instances, network connections are not reliable for persistent connections, as well as subject for interception from unauthorized entities. For many medical conditions, this is unacceptable because the patient user must have access to certain medical and/or health-data constantly and in real-time. And for medical devices that integrate some of their functionalities with other devices, such persistent access and distribution of the data may be critical to maintain the integrated capabilities. An example includes the insulin delivery device requesting access to glucose levels, e.g., in real-time and/or retrospectively, such as glucose levels of the previous days, so that the insulin delivery device can integrate the glucose levels with information it may have, such as insulin on board (JOB), insulin action, and food (e.g., carbohydrate) consumption. Similarly, the glucose sensor device may request access to certain data from the insulin delivery device, such as time of a bolus, amount of bolus, or JOB, which can be used by the glucose sensor device to perform device self-diagnostics, detect patterns, and/or enrich the user's information about their glucose monitoring.

Some aspects of the present technology disclosed in this patent document is directed to overcoming these and other challenges. While several examples of challenges that arise in a system for managing diabetes including continuous glucose monitoring and/or insulin delivery are described, other problems and solutions are discussed below throughout the specification, and the scope of the disclosure and claims of the present technology should not be limited to addressing only challenges associated with managing data associated with continuous glucose monitoring and insulin delivery.

Examples are discussed to illustrate some embodiments of the present technology disclosed herein.

In some embodiments, the inter-app communications architecture includes a universal resource locator (URL) linking structure to transition and provide data between a source app (e.g., a first app) and one or more target apps (e.g., a second app). The URL linking structure is configured to, when executed, initiate a second app to open in the foreground while concurrently sending a secure data payload to the second app from the first app. Similarly, the URL linking structure can request data for the first app from the second app and facilitate reception of the requested data. The URL linking structure therefore enables the first app to start another app while providing a payload containing a request and parameters, e.g., such as show the home screen of the second app, execute a particular feature or secondary screen of the second app, or request data from the second app.

In some embodiments, the inter-app communications architecture includes a shared database architecture between a source app and one or more target apps that facilitates secure data distribution via an encrypted database file system. In the shared database architecture, the source app possesses a database key that is a symmetric key for encrypting and decrypting the encrypted, shared database file system. The symmetric key is itself encrypted, in which a public/private key pair is provided to each linked target app, e.g., the private key stored in the private keychains, and public key kept in a shared app group's shared keychain. The source app manages the database key to the shared database file, in which the source app provides encrypted copies of the database key in the shared app group's shared keychain, and removes the database key copies from the shared keychain when a target app is unlinked, and rekeys the database to a new key.

In some embodiments, the inter-app communications architecture utilizes the URL linking structure with the shared database to transition between the source app and the target app, and vice versa, and distribute data. The URL linking structure, when implemented from the source app, initiates the target app to open in the foreground and may concurrently send a secure data payload to the target app from the source app. The shared database architecture facilitates access for the source and target apps to the secured shared database file, e.g., which allows efficient distribution of real-time data and modifications to data shared between the apps. The shared database is secured using an encryption system in which the source app possesses a symmetric key (the "database key") and each linked target app possesses a private key stored in their private keychains to decrypt their copies of the database key kept in a shared keychain. The source app manages the creation and destruction of the database key to the shared database file so that access to the shared database is limited to apps published by the source app entity (e.g., by the use of a shared app group within the operating system (OS) structure).

One particular example implementation of the present technology applies to a software application for continuous glucose monitoring (CGM), referred to as a "CGM app," and a software application for insulin management, e.g., for an insulin pump device or insulin pen device, referred to as an "Insulin app." In some embodiments of the present technology, the disclosed inter-app architecture allows for a source app (e.g., the CGM app) to seamlessly link to one or more target apps (e.g., Insulin apps), e.g., in a manner that is analogous to 'plugging in' an Insulin app into the CGM app, or vice versa. For example, a user of the CGM app can simply click a tab, icon, or other representation to open the Insulin app and import in any of the relevant data from the CGM in a transition that appears invisible to the user. In one example, there is only one CGM app and there can be several Insulin apps that can be stored and operating on the user's smartphone. The Insulin app is the smartphone representative for the user's insulin device (e.g., insulin pump and/or insulin injection device, such as a pen, syringe, etc.). The CGM app is a mobile medical software application ("mobile medical app") that receives medical data from a patient user's medical device, e.g., such as a continuous glucose sensor device, and processes the medical data to provide the medical data to (i) the patient user on his/her mobile computing device (e.g., smartphone) executing the mobile medical app and/or (ii) the Insulin app to utilize in the management of insulin delivery for the patient user. For example, the architecture can facilitate the interaction of the CGM app with the one or more Insulin apps that support multiple models of the insulin pump or pen in a controlled fashion. For example, the CGM app can also provide the raw and/or processed medical data to a data repository (e.g., in the Cloud) for access by a healthcare professional (HCP), caregiver, or other user in accordance with some implementations.

In an illustrative example, a patient user of an insulin delivery device (e.g. pump or pen) selects, in the CGM App, an Insulin app that corresponds to their specific insulin device. More specifically, to link between the appropriate Insulin app and the CGM app in accordance with this example, the CGM app provides a display screen listing approved Insulin apps (one of which corresponds to the user's delivery device). Once the user selects the Insulin app corresponding to the user's insulin delivery device (e.g., via a button title "Link" located proximate to identification information of the Insulin app), the computing device establishes a link between the apps.

In this illustrative example, by a user selecting a "Link" button, the computing device establishes the link between the CGM app and the corresponding Insulin app and immediately and seamlessly transitions to the selected Insulin app. That is, the user-selection initiates the smart device to open the Insulin app and present the Insulin app in the foreground of the computing device's display. If the user has not yet downloaded the Insulin app, selection of a button corresponding to that Insulin app also initiates the computing device to download Insulin app from a digital distribution platform for mobile apps that provides the Insulin app for download, such as Apple's App Store digital app distribution platform. The button can be user-selectable button titled "Get" located proximate to identification information of the Insulin app to be downloaded).

Further to this illustrative example, only Insulin apps linked to the CGM app in the above fashion on the user's computing device have access to the user's data distributed from the CGM app in a manner according to implementations of the inter-app communications architecture. Once the link between the CGM app and the Insulin app is established, the user can unlink the CGM app from the linked Insulin app, thereby severing the seamless transition between apps and terminating the data sharing between the two apps.

In some implementations, an Insulin app manages data associated with the Insulin Pump status and device management, whereas a CGM app imports insulin data and integrates it with CGM data. The CGM app can then present the key or most-important glucose and insulin information to the patient user for empowering real-time decision-making based on his/her condition quickly, safely and effectively. The CGM app can also be configured to manage the sharing of the glucose and insulin data with the patient user's remote monitors, e.g., via providing such data to a server that manages data permissions and notification rules for remote monitors to be informed about the patient user's glucose state.

Example Embodiments

FIG. 1A is a diagram showing an inter-app communications architecture 100 on a mobile computing device 130 to facilitate data distribution and inter-app transitions between a source app 101 and one or more target apps 102a, 102b, . . . 102n that may be linked to the source app 101 in accordance with embodiments of the inter-app communications 100 of the present technology. Various embodiments of the inter-app communications architecture 100 can control the distribution of data associated with the source app 101 to a target app in which the inter-app communications architecture 100 has been established, and vice versa. In some example embodiments, the inter-app communications architecture 100 includes a universal resource locator (URL) linking architecture 110, also referred to as the URL linking structure. In some example embodiments, the inter-app communications architecture 100 includes a shared database architecture 120. In some example embodiments, the inter-app communications architecture 100 includes the URL linking architecture 110 and the shared database architecture 120. As shown in the example of FIG. 1A, the source app 101 provides data to the target app 102a through the inter-app communication architecture 100. In this example, the source app 101 can implement the URL linking structure 110 to provide a data payload and initiate the target app 102a to open in the foreground of the computing device 130. Also, for example, the source app 101 can utilize the shared database architecture 120 to provide access to shared data between the source app and target app 102a having the architecture 120 established to an encrypted shared database, in which the linked apps 101 and 102a can add, delete and/or modify the shared data in the shared database.

The mobile computing device 130 can be in communication with one or more external devices, shown as external devices 170A and 170B for example, and/or with one or more external networks 171 of computing devices, e.g., such as servers in the Cloud. For example, the mobile computing device 130 can communicatively interface with the external devices 170A, 170B and/or external networks 171 using various types of wired or wireless interfaces, e.g., such as those compatible with typical data communication standards, for example, including, but not limited to, Bluetooth, Bluetooth low energy (BLE), ZigBee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, and parallel interfaces. Therefore, the mobile computing device 130 is able to receive data from external devices 170A, 170B and/or external networks 171 that can be provided to the source app 101 and the one or more target apps 102a, 102b, . . . 102n, and in turn that data can be distributed between the source app 101 and target apps 102a, 102b, . . . 102n through the inter-app communications architecture 100. For example, the source app 102a may receive data, via the mobile computing device 130, from the external device 170A, and the target app 102a may receive data, via the mobile computing device 130, from the external device 170B. Implementations of the inter-app communications architecture 100 provides a secure data distribution technique to control how data from the external device 170B may be provided to the source app 101, for example; and similarly, the inter-app communications architecture 100 provides a secure data distribution technique to control how data from the external device 170A may be provided to the target app 102a.

Similarly, as shown in the example of FIG. 1A, the source app 101 can provide data to the target app 102b through the inter-app communication architecture 100 when established between the two apps. In certain implementations in accordance with the present technology, the specific target apps with which the source app may establish the inter-app communications architecture 100 are preapproved and listed with the source app. In the example shown in FIG. 1A, the target app 102n is shown as one of the preapproved apps with which the source app may establish the inter-app communications architecture 100, but has not yet established. While not shown in FIG. 1A, some implementations in accordance with the inter-app communications architecture 100 can include an established architecture between the target apps 102a, 102b, and/or 102n, which may differ in some ways from that established between the source app and the one or more target apps 102a, 102b . . . 102n. For example, the target app 102a can have a different list of preapproved apps with which it is capable to establish the inter-app communications architecture 100, e.g., which can include other apps besides the source app 101 and the target apps 102b . . . 102n.

Figure 1B:
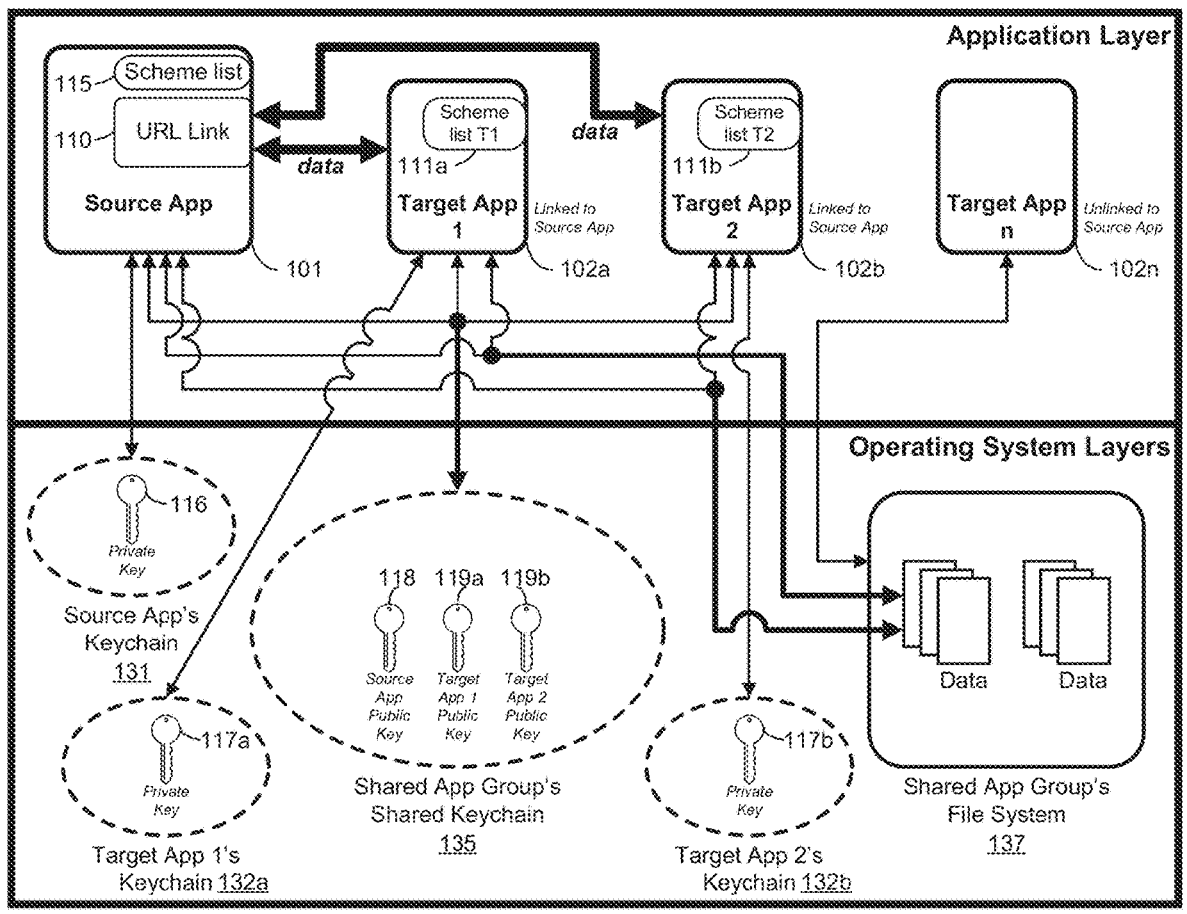
FIG. 1B is a diagram showing an example of an inter-app communications architecture between a source app and one or more target apps integrated with the device operating system using a URL linking architecture in accordance with some implementations of the present technology.
Figure 1C:
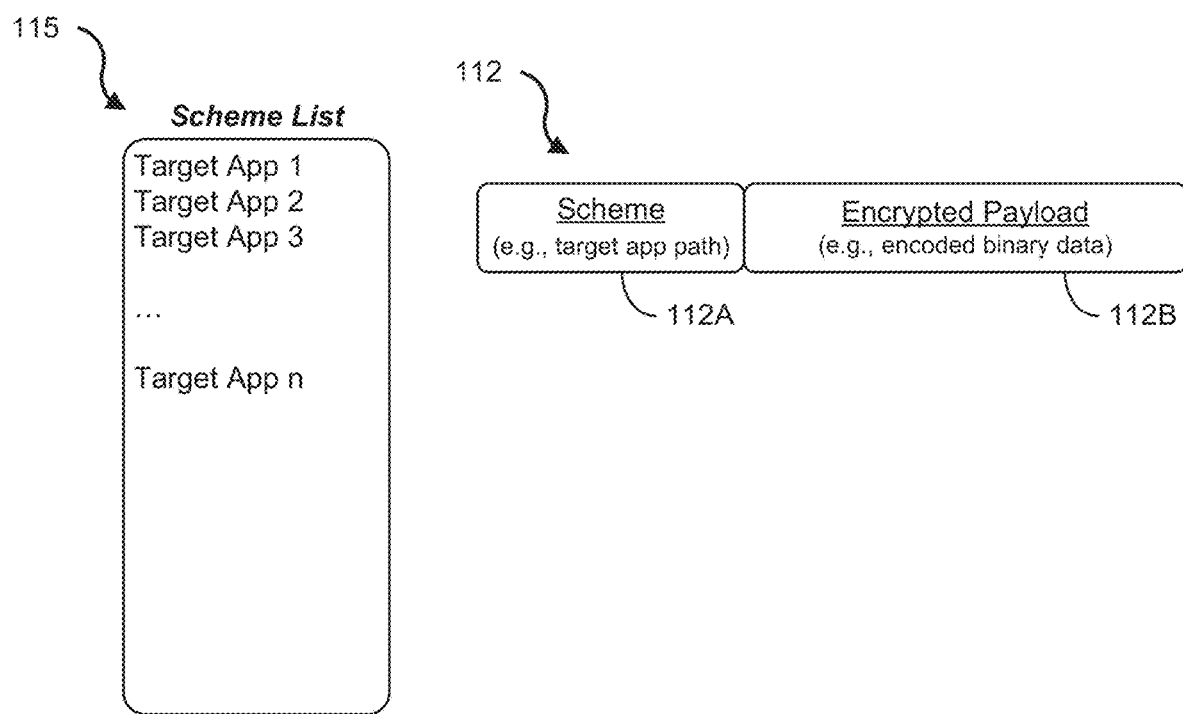
FIG. 1C is a diagram of an example URL linking data structure in accordance with some implementations of the present technology.

In some embodiments of the inter-app communications architecture 100 in accordance with FIG. 1A and FIGS. 1B and 1C, the inter-app communications architecture 100 includes the URL linking structure 110 to control secure data transmissions between the source app 101 and the one or more target apps 102a, 102b, . . . 102n operating on the mobile computing device 130. The URL linking structure 110 is configured to, when executed, initiate a linked target app (e.g., the target app 102a or 102b) into the foreground of the mobile computing device 130 while concurrently sending a secure data payload to the target app. The URL linking architecture 110 includes a data structure 112 includes a scheme 112A that identifies the target app to initiate and transition to from the source app 101. The target app is identified from a list of pre-approved target apps to allow linking with the source app. The data structure 112 includes a secure payload including encrypted data and/or an optional path to encrypted data. The URL linking architecture 110 includes a scheme list 115 providing the scheme path of pre-approved target apps to populate the scheme 112A in the data structure 112 when the URL linking architecture 110 is employed. In some implementations in accordance with this example embodiment of the URL linking architecture 110, an icon representative of the linked target app is presented on the user interface of the source app 101 to allow the user to seamlessly transition between the source app 101 and the linked target app when desired. For example, when the linked target app is the target app 102a, selection of the icon activates execution of the URL linking structure 110 to initiate the target app 102a on the mobile computing device 130 based on the scheme 112A identifying the scheme path of the target app 102, and, moreover, the URL linking structure 110 provides the target app 102a with encrypted data from the source app 101 and/or a path to the encrypted data stored in a shared file system 137 with the source app 101 and the pre-approved target apps. For example, if it is the first execution of the URL linking structure 110, a reciprocal copy of the scheme 112A may be provided to the linked target app, where the scheme identifies the source app. In implementations where the URL linking architecture 110 is established with the one or more target apps, the linked target app is configured to utilize a reciprocal URL linking structure to link back from the linked target app to the source app. For example, when the linked target app is the target app 102a, the target app 102a is configured to display a link (e.g., an icon representative of the linked source app 101) to activate execution of the reciprocal URL linking structure to seamlessly transition back to the source app 101, when the icon is selected by the user. The reciprocal URL linking structure can request data from the target app for the source app and facilitate reception of the requested data, e.g., via the payload. The URL linking structure therefore enables the source app to start another pre-approved app while providing a payload. In some implementations of the inter-app communications architecture 100, for example, the payload can contain data, a path to data, and/or parameters of linking between the apps, e.g., such as show the home screen of the target app, execute a particular feature or secondary screen of the target app, or request data from the target app. To ensure privacy of the data exchanged between apps, the inter-app communications architecture 100 can be configured such that all payload data sent in the URL linking structure 110 is encrypted using public key cryptography. For example, the payload can include a dictionary of key/value pairs containing the request and its parameters, in which the dictionary is encoded into binary data, digitally signed, encrypted, and encoded into a string for the path section of the URL linking structure.

FIG. 1B is a diagram showing an example of the URL linking architecture 110 between a source app and one or more target apps integrated with the device operating system in accordance with some implementations of the present technology. In the example shown in FIG. 1B, the URL linking architecture 110 is established between the source app 101 and two apps of the shared app group, the target app 1 (labeled as 102a) and a target app 2 (labeled as 102b). The source app includes the scheme list 115 of the preapproved target apps, e.g., which are included in the shared app group. FIG. 1C is a diagram of an example embodiment of the URL linking data structure 112, which can be implemented in code, and including the scheme 112A and encrypted payload 112B. Referring to the example shown in FIG. 1B, the public keys for the linked apps are stored in the shared app group keychain, and the private keys for the linked apps are stored in the respective private keychains. Public key 116 of the source app 101, public key 119a of the target app 102a, and public key 119b of the target app 102b are kept in the shared app group's shared keychain 135. Private key 116 of the source app 101 is kept in the source app's keychain 131. Private key 117a of the target app 102a is kept in the target app 1's keychain 132a, and private key 117b of the target app 102b is kept in the target app 2's keychain 132b. When the URL linking is implemented, e.g., from the source app 101 to transition the target app 102a into the foreground, the encrypted payload 112B is provided to the target app 102a. Similarly, when the URL linking is implemented, e.g., from the source app 101 to transition the target app 102b into the foreground, the encrypted payload 112B is provided to the target app 102b. In some implementations, the encrypted payload 112B contains data such as a data point or points. In addition or alternatively, the encrypted payload 112B can contain one or more identifiers to data in the shared app group's file system 137. The linked target apps can also include their own respective scheme lists (e.g., shown as 111a and 111b in FIG. 1B), which lists the source app scheme such that the URL linking can be implemented to transition from the target app (e.g., target app 1 or target app 2) to the source app 101 to operate in the foreground.

Figure 1D:
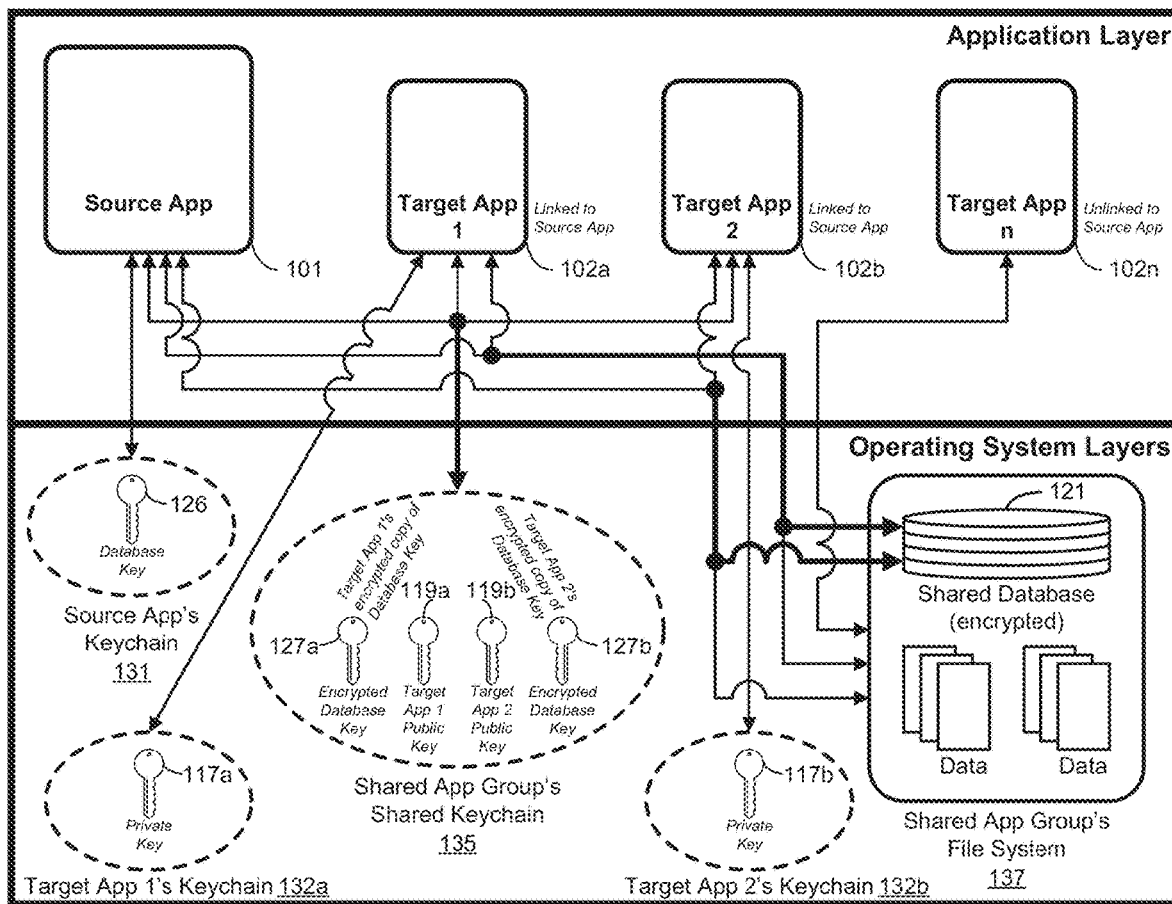
FIG. 1D is a diagram showing an example of an inter-app communications architecture between a source app and one or more target apps integrated with the device operating system using a shared database architecture in accordance with some implementations of the present technology.

In some embodiments of the inter-app communications architecture 100 in accordance with FIG. 1A and FIG. 1D, the inter-app communications architecture 100 includes the shared database architecture 120 between the source app 101 and the one or more target apps 102a, 102b . . . 102n that facilitates secure data distribution via an encrypted database file system. In this example embodiment, the source app 101 possesses a symmetric key 126 (e.g., the "database key") stored in the source app's keychain 131. Each linked target app possesses a private key stored in their private keychains (e.g., the target app 102a's private keychain 132a and the target app 102b's private keychain 132b, as depicted in FIG. 1D) to decrypt their respective copies of the encrypted database key kept in the shared app group's shared keychain 135. The source app 101 manages the encryption key to the shared database file, in which encrypted copies of the database key are provided to the target apps in the shared app group's shared keychain 135, where a linked target app can decrypt using its private key, so that it can be used in accessing the encrypted database file system. The source app 101 is able to remove the copy of the database key from the shared keychain 135 when a target app is unlinked, and rekey the database to a new key.

Implementations of embodiments of the shared database architecture 120 can include data distribution of real-time data and modifications of shared data, e.g., such as background data like icons and graphics, user profile data, device status data, and other types of data that should be automatically shared between the source and target apps without necessitating a user-selected transition.

In the shared database architecture 120, the source app 101 manages the encryption key to the shared database file. The source app 101 keeps the database key 126 in its private keychain 131. Pre-approved target apps in the shared app group are able to access to the shared app group's file system 137 and the shared keychain 135, but only linked target apps that have the encrypted copy of the database key can access the data associated with the encrypted shared database 121 (e.g., read/write data from/to the shared database 121). In some implementations of the shared database architecture 120, the public/private key pair is generated for the linked target app during its initial setup, e.g., when the linked target app is first run. In an example where the linked target apps include the target app 102a, the target app 102a's public key 119a is kept in the shared app group's shared keychain 135 (and thereby available to the source app 101), and the target app 102a's private key 117a is kept in the target app's (private) keychain. When the target app is initially linked to the source app 101, a copy of the database key is made available to target apps in the shared app group's shared keychain 135 that is encrypted with the "linked" target app's public key. So, while all apps in the shared app group have access to the shared keychain 135, only the user-selected target app (i.e., linked target app) has the necessary private key to decrypt the encrypted database key. For example, when the target app is unlinked, e.g., to terminate the inter-app communications, the source app 101 removes the encrypted copy of the database key from the shared keychain and then rekeys the database to a new key. The source app 101 updates the database key 126 saved in its private keychain 131.

FIG. 1D is a diagram showing an example of the shared database architecture 120 between a source app and one or more target apps integrated with the device operating system in accordance with some implementations of the present technology. In the example shown in FIG. 1D, in the shared database architecture 120, the public keys 119*a* and 119*b* for the linked target apps 102*a* and 102*b*, respectively, are stored in the shared app group keychain 135, and the private keys for the linked target apps are stored in the respective target apps' private keychains. Private key 117*a* of the target app 102*a* is kept in the target app 1's keychain 132*a*, and private key 117*b* of the target app 102*b* is kept in the target app 2's keychain 132*b*. It is noted, for example, that the private keys of the public/private key pair for the linked target apps (e.g., private keys 117*a* and 117*b* in FIG. 1D) in the shared database architecture 120 may be the same private keys as those for the URL linking architecture 110; whereas in some implementations of the shared database architecture 120, the private keys of the public/private key pair may be different than those if the URL architecture 110 is employed (e.g., for encrypting the data payload). Referring to the example shown in FIG. 1D, the database key 126 is stored in the source app's private keychain 131. The encrypted copies of the database key for the respective linked target apps, i.e., encrypted database key 127*a* for the target app 102*a* and encrypted database key 127*b* for the target app 102*b* for this example, are stored in the shared app group's keychain 135. When data of the encrypted shared database 121 is to be accessed by any of the linked apps, e.g., the source app 101, the target app 102*a* and/or the target app 102*b* in this example, the app can use their respective protected database key to access the shared database 121 and read and/or write to the database.

In some embodiments, the inter-app communications architecture 100 includes the URL linking structure 110 operable in conjunction with a shared database architecture 120 between the source app 101 and the one or more target apps 102*a*, 102*b* . . . 102*n*. In such embodiments, the inter-app communications architecture 100 utilizes the URL linking structure 110 architecture to transition between the source app 101 and the linked target app, and vice versa, and facilitates data distribution between the apps using the payload 112B of the URL data structure 112 and/or the shared database 121.

Figure 1E:
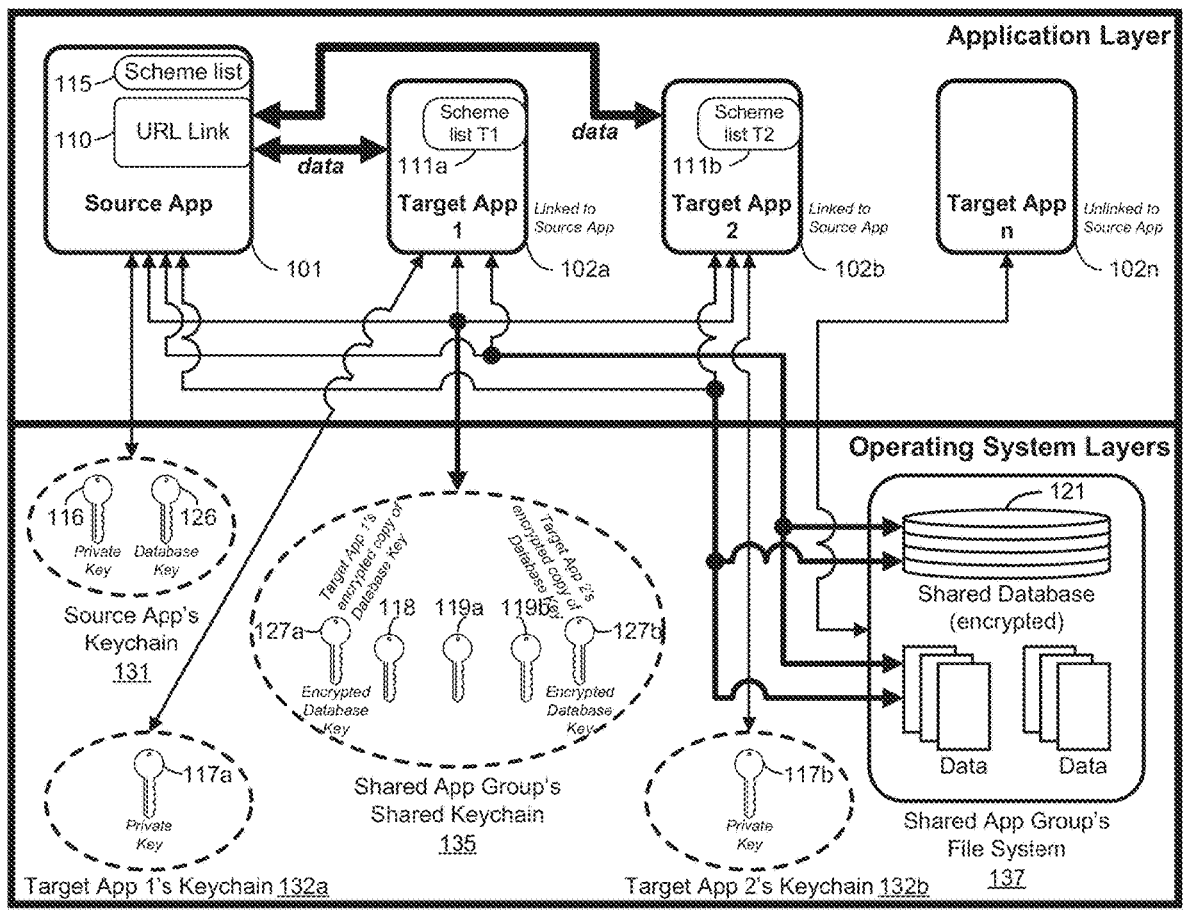
FIG. 1E is a diagram showing an example of an inter-app communications architecture between a source app and one or more target apps integrated with the device operating system using a URL linking architecture and a shared database architecture in accordance with some implementations of the present technology.

FIG. 1E is a diagram showing an example embodiment of the inter-app communications architecture 100 between the source app 101 and the target apps 102*a* and 102*b* integrated with the device operating system using the URL linking architecture 110 and the shared database architecture 120 in accordance with some implementations of the present technology. In the example shown in FIG. 1E, the URL linking architecture 110 is established between the source app 101 and (i) the target app 102*a* and (ii) the target app 102*b* of the preapproved apps of the scheme list. The public keys 118, 119*a*, and 119*b* for the linked apps (e.g., for the source app 101, the target app 102*a*, and the target app 102*b*, respectively) are stored in the shared app group keychain 135; and the private keys 116, 117*a*, and 117*b* for the linked apps are stored in the respective private keychains 131, 132*a*, and 132*b* (e.g., for the source app 101, the target app 102*a*, and the target app 102*b*, respectively). The database key 126 is stored in the source app's private keychain 131. The encrypted copies of the database key for the target apps 1 and 2, i.e., encrypted database key 127*a* for the target app 102*a* and encrypted database key 127*b* for the target app 102*b*, are stored in the shared app group's keychain 135. When data is to be accessed by any of the linked apps, e.g., the source app 101, the target app 102*a* and/or the target app 102*b* in this example, the app can use their respective protected database key to access the shared database 121 and read and/or write to the database. When the URL linking is implemented, e.g., from the source app 101 to transition the target app 102*a* into the foreground, the encrypted payload 112A is provided to the target app 102*a*. For example, the encrypted payload can contain data such as a data point or points. In addition or alternatively, the encrypted payload can contain one or more identifiers to data in the shared app group's file system 137.

Figure 1F:
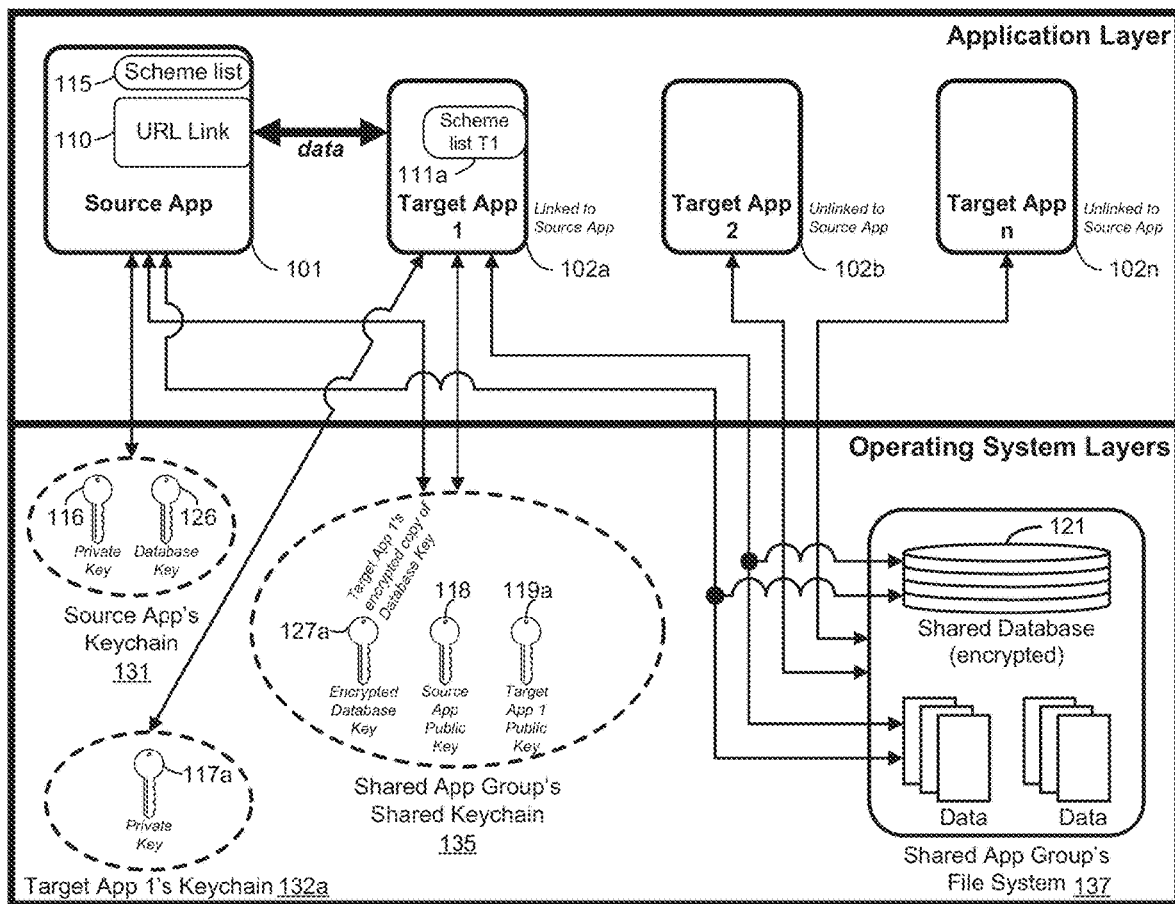
FIG. 1F is a diagram showing an example of an inter-app communications architecture between a source app and one target app using a URL linking architecture and a shared database architecture in accordance with some implementations of the present technology.

FIG. 1F is a diagram of the example inter-app communications architecture between the source app 101 and one target app (e.g., the target app 102*a*) using the URL linking architecture 110 and the shared database architecture 120 in accordance with some implementations of the present technology.

In accordance with certain implementations of the present technology, the inter-app communications architecture 100 provides a process to link two or more software apps on the back end that facilitates the inter-app transition and data distribution. Once linked, a user may seamlessly interchange between the source app 101 and linked target apps 102*a*, 102*b*, . . . and/or 102*n* such that shared data and the user interface (UI) between the linked apps offers a consistent and uniform experience to the user on the front end, virtually simulating a single app experience through the interaction of the two or more independent apps linked through the inter-app communications architecture 100.

In some embodiments, the source app 101 may initially link to a user-selected target app in the following manner. The one or more target apps 102*a*, 102*b* . . . 102*n* that may be linked to the source app 101 are predetermined and listed on the scheme list 115 and to the operating system, e.g., such as on a shared app group list.

Figure 2A:
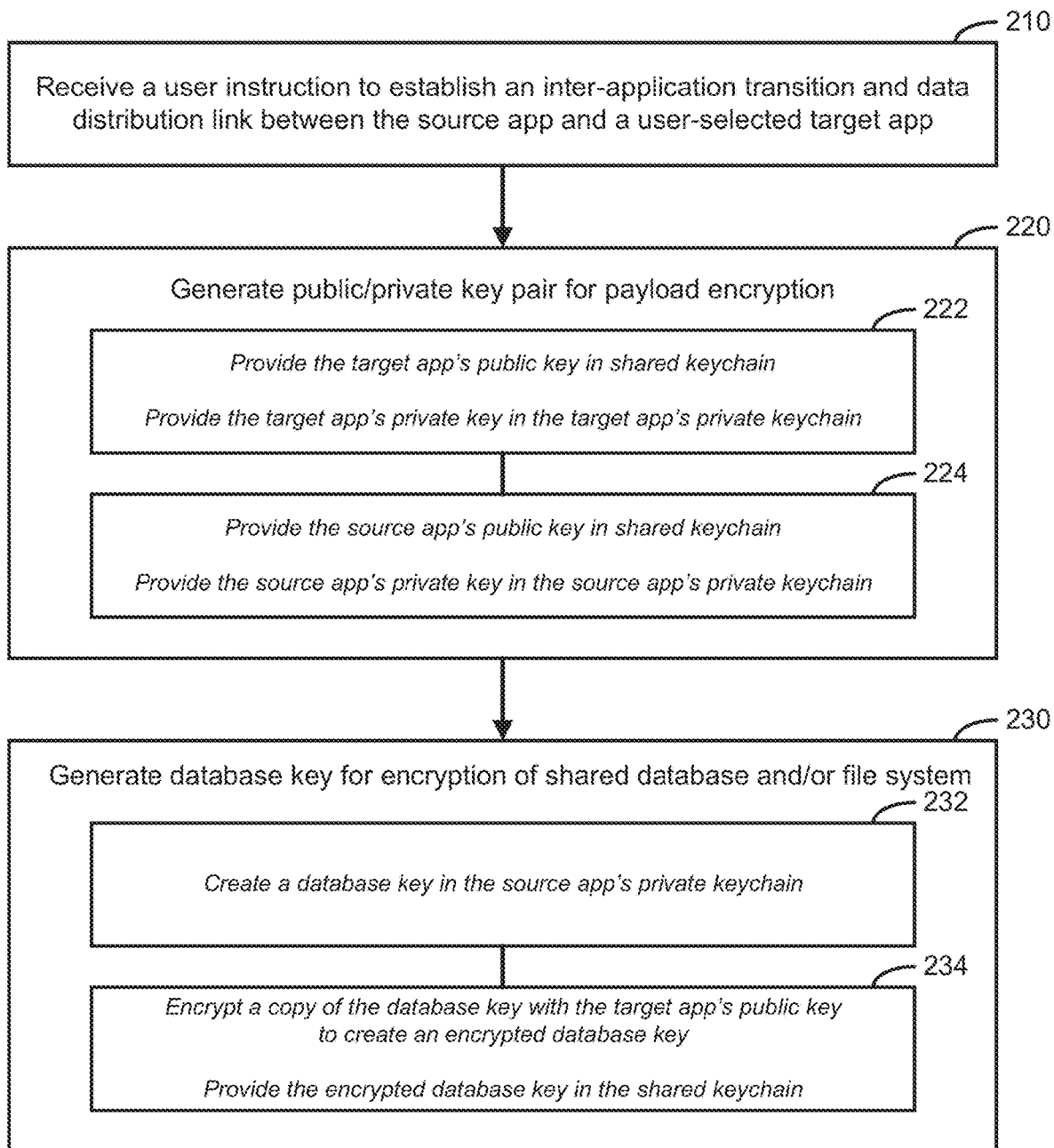
FIG. 2A is a flow diagram of an example method to establish a data communications link between a source app and a target app in accordance with some implementations of the present technology.

FIG. 2A shows a method to establish a link between a source app and a target app in accordance with some implementations of the disclosed inter-app communications architecture 100. The method includes a process 210 to receive a user instruction to establish an inter-application transition and data distribution link between the source app and a target app selected by the user. For example, the source app may include a display screen that lists all of the preapproved target apps listed on its scheme list (e.g., and listed with the operating system on a shared app group list).

Figure 2B:
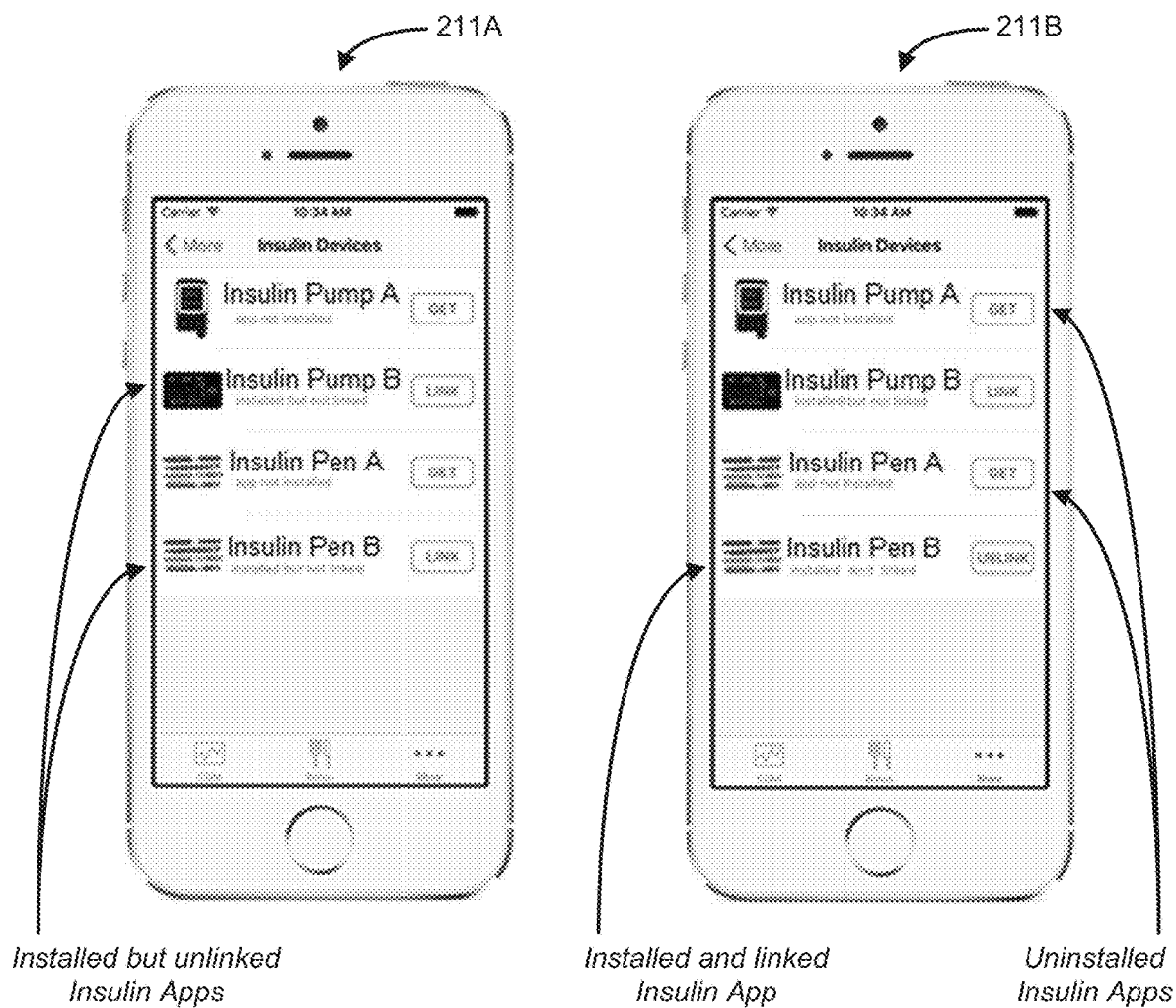
FIG. 2B is a diagram of display screens of the source app depicting an example user interface to select a target app to be linked to the source in accordance with some implementations.

FIG. 2B is a diagram of display screens of the source app depicting an example user interface to select a target app to be linked to the source app in accordance with some implementations of the process 210. The display screen can list the name of the device associated with the target app, an icon or image of the device, and status information indicative of the target app's linking status to the source app and a button to allow the user to change the status. For example, target apps not resident on the user's mobile computing device (e.g., smartphone) can list status information such as "app not installed," and the associated button can be labeled as "GET" to direct the user to the app store (associated with the user device) to facilitate download of the preapproved target app. Target apps already resident on the user's mobile computing device can list the status information such as "installed and linked" and/or "installed but not linked," and the button associated button can be labeled as "LINK" and/or "UNLINK", respectively.

The menu of available target apps (e.g., Insulin apps) is provided by the source app (e.g., CGM app) via a controlled, digitally signed configuration file, which can be updated by the controlling entity of the source app when the partner entities controlling the respective target apps receive approval. For example, in the case of the CGM app and target Insulin apps, the CGM app controlling entity may require that Insulin app partners provide evidence of regulatory approval and/or 510(k) clearance before adding the Insulin app to the menu. The configuration file includes a digital signature, which allows the CGM app to validate the authenticity of the file and verify that it is correct and unaltered. For example, insulin delivery devices will not be visible on the menu or available to the user until approved. Each time an Insulin app is approved and becomes commercially available, the configuration file can be updated to include details of that app. In some implementations, for example, the signed file can be web hosted, which allows the CGM app controlling entity to make updates without requiring their users to upgrade their app version. The configuration file is configured such that it does not alter any display or alert features of the source app. The configuration file only includes the target apps that may link to the shared inter-app communication system. In some implementations, the configuration file can also provide details for each target app, e.g., including a direct link to the app on the associated app store for its installation, a description of the target app to display to the user, and information pertaining to establishment of the link between the source and target apps.

Based on the instruction to establish the link (e.g., user selection of the "LINK" button next to the listing of the target app (associated device) the user intends to link), the method can be implemented to establish the link to the target app. The LINK button initiates the secure communications link between the two apps. Referring back to FIG. 2A, to establish the link, the method includes a process 220 to generate a public/private key pair for encryption and decryption of the payload of the URL linking structure. The process 220 can include a process 222 to provide a public key for the target app in the shared keychain and a private key for the target app in the target app's private keychain. In some implementations, the process 220 can include a process 224 to provide a public key for the source app in the shared keychain and a private key for the source app in the source app's private keychain. The method includes a process 230 to generate a database key for encryption of the shared database of the shared file system. The process 230 can include a process 232 to create a database key in the source app's private keychain, and a process 234 to encrypt a copy of the database key with the target app's public key for creation of an encrypted database key, in which the encrypted database key is provided in the shared keychain. After implementation of the process 230, the target app is linked and is able to read the shared database, e.g., using the encrypted database key. Similarly, the source app is also able to read the shared database, e.g., and access data distributed by the target app into the encrypted shared database.

In some embodiments of the method of FIG. 2A, the method includes a process to facilitate installation of an uninstalled preapproved target app. For example, with reference to FIG. 2B, the source app can include a link, e.g., operable upon selection of the "GET" button on a display screen of the source app, to an app store where the user can obtain the preapproved target app. In some embodiments of the method, the method includes the process 220 and 230 without implementation of the process 210. For example, the method can establish the link between the source app and the target app based on other input not necessarily provided by the user, e.g., such as a received instruction from another application or process. In one example, the source app may receive a command by an authorized source, such as a software program or electronic communication from the user's physician, to cause implementation of the processes 220 and 230 to establish the link.

Figure 3A:
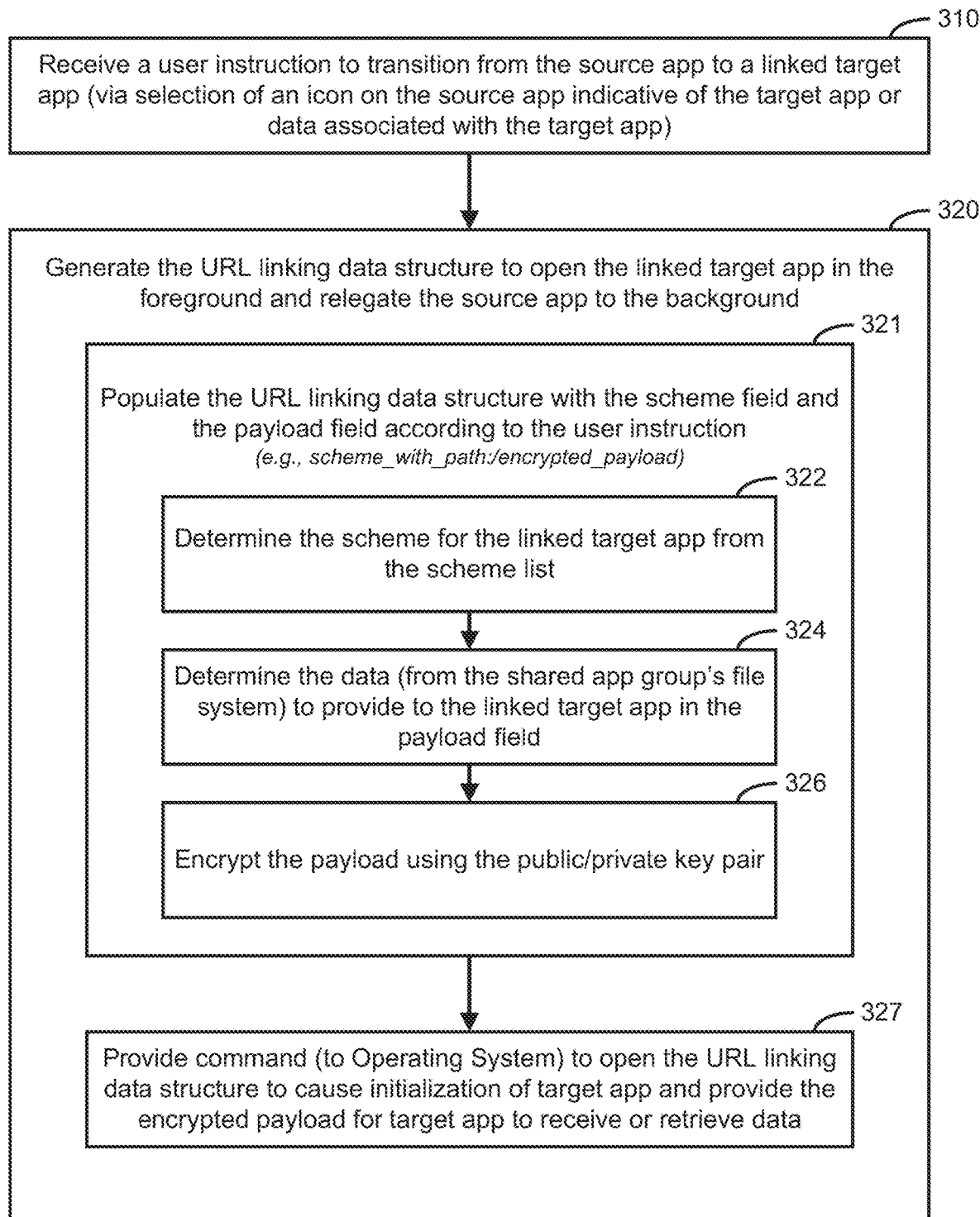
FIG. 3A is a flow diagram of an example method to transition and distribute data between a source app and a target app in accordance with some implementations of the inter-app communications architecture of the present technology.

Once the source app and the target app are linked, the user can seamlessly transition between the source app and the linked target app for operation of both apps with appropriate data distributed between them. FIG. 3A shows a method to link between a source app and a target app in accordance with some implementations of the disclosed inter-app communications architecture 100. The method includes a process 310 to receive a user instruction to transition from the source app to a linked target app. In some implementations, the instruction can be received from a user selection of an icon or other representation of the target app or data associated with the target app presented on a display screen of the source app.

Figure 3B:
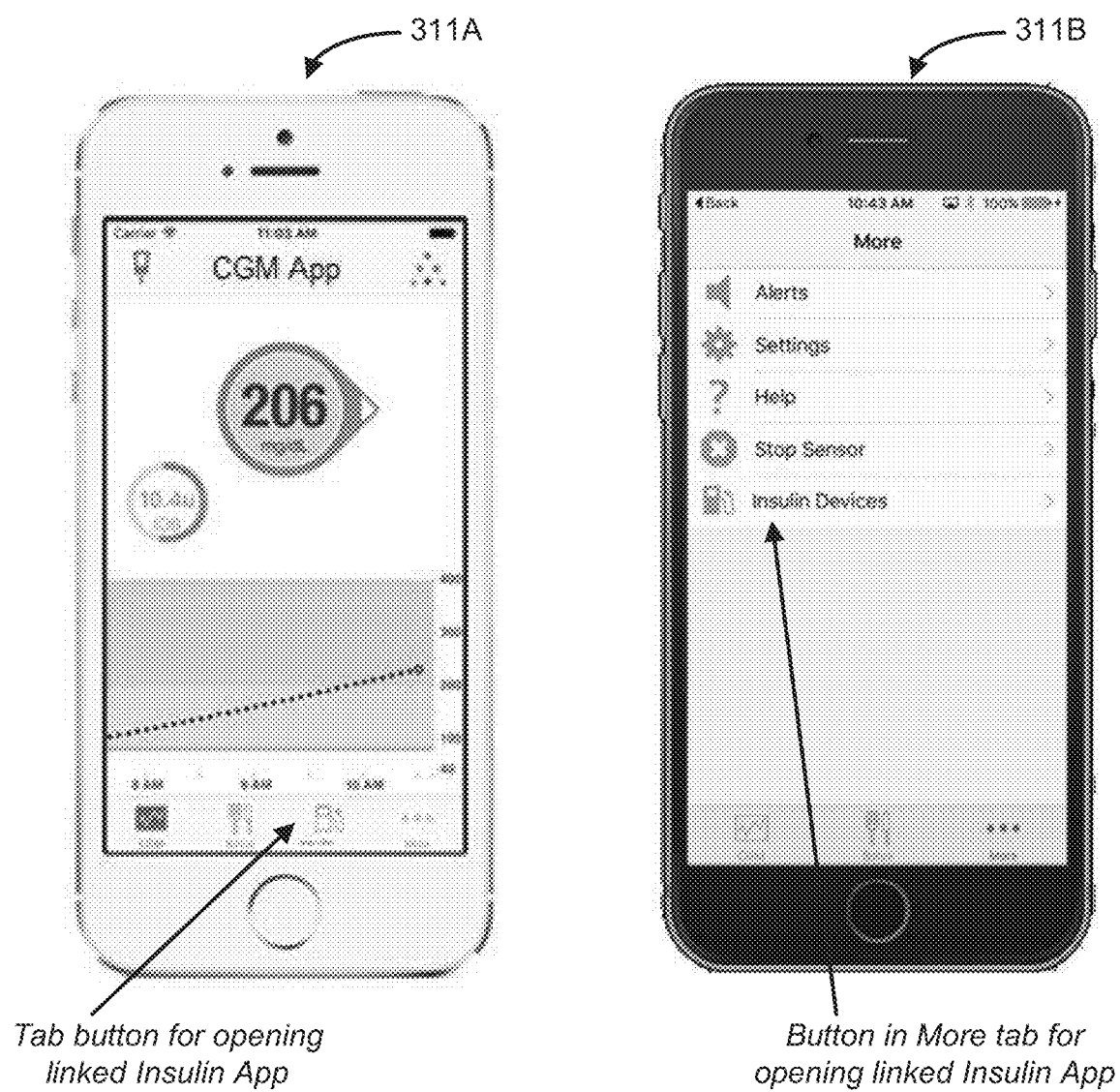
FIG. 3B is a diagram of display screens of the source app depicting an example user interface to select a target app icon to initiate transition from the source app to the target app in accordance with some implementations.

For example, a user using the source app may select an icon indicative of the linked target app or data associated with the target app to seamlessly open the target app (e.g., to operate in the foreground) and exit the source app (e.g., to operate the background or close the app). FIG. 3B is a diagram of display screens of the source app depicting an example user interface to select a target app icon to initiate the target app in accordance with some implementations of the process 310. The display screen can provide a button for the linked target app in a prominent tab list of features of the source app or in a listing of features of the more tab. Also, for example, the user can select data associated with the linked target app to cause the transition from the source app to the target app. In an illustrative example, the CGM app (source app) can display insulin data provided by the linked Insulin app (target app), such as the IOB data (shown as "10.4u IOB" in the figure) on a display screen of the CGM app. The user may select of the data graphic to link to the Insulin app.

Referring back to FIG. 3A, the method includes a process 320 to generate the URL linking data structure (e.g., data structure 112) to open the linked target app in the foreground, e.g., and relegate the source app to the background or close the source app. The process 320 can include a process 321 to populate the URL linking data structure in the scheme portion and the payload portion (e.g., based on information received from the user instruction); and a process 327 to provide a command (e.g., to the operating system) to open the URL linking data structure to cause the target app to open (based on the scheme of the URL linking data structure) and provide the encrypted payload for the target app to receive or retrieve data. In some embodiments, the process 321 includes a process 322 to determine the scheme for the linked target app from the scheme list; the process 321 includes a process 324 to determine the payload to provide the linked target app; and the process 321 includes a process 326 to encrypt the payload using the public/private key pair. In some implementations of the process 324, the payload can include data (e.g., data points, such as estimated glucose values (EGV)) and/or an identification of where data is from the shared app group's file system to be provided to the linked target app.

In some implementations of the process 327, the URL linking data structure is provided to the operating system, which can determine from the scheme portion of the URL linking data structure to open the target app. Once the target app is opened, the target app can then decrypt the encrypted payload of the URL linking data structure and decode the decrypted payload to process what is in the payload, e.g., such as data encoded in the payload portion and/or an identification to data that is stored in the shared file system. In an illustrative example, the source app is a CGM app that includes a bolus calculator engine that determines an insulin bolus amount (e.g., based on user input and/or data from the CGM app such as current glucose concentration and trend) and stores the insulin bolus data in the shared file system, with an identification to locate the stored insulin bolus data. The target app is an Insulin app that benefits from the calculated bolus amount for various features of the Insulin app, such as controlling delivery of insulin. The user may seamlessly transition from the CGM app to the linked Insulin app after operating the bolus calculator engine, where the URL linking data structure includes the identification to the insulin bolus data in the encrypted payload portion. The Insulin app decrypts the encrypted identification (in the payload) and decodes the identification to locate the insulin bolus data, which it can retrieve and process to perform the operations of the Insulin app. Once the payload is decrypted and decoded, the Insulin app can remove the URL linking data structure (e.g., the payload).

In some embodiments, the method of FIG. 3A includes a process implemented by the linked target app to generate a URL linking data structure to open the linked source app in the foreground and relegate the target app to the background, and a process to provide a command (to the operating system) to open the generated URL linking data structure to cause initialization of source app and provide the encrypted payload for the source app to receive or retrieve data from the target app. In such embodiments, the target app includes its own scheme list that includes the scheme ID of the source app. Based on the establishment of the link between the source app and the target app (e.g., described in the method of FIG. 2A), the target app possesses a copy of the encrypted database key to the encrypted shared database in the shared file system and the public/private key pairs for encryption of the payload to send to the source app. In some implementations, the target app's scheme list can include other pre-approved applications beyond the source app to interactively communicate with, e.g., which can include other preapproved apps on the source app's scheme list. In some implementations, the target app's scheme list can include other preapproved applications not on the source app's scheme list, and in such implementations the target app would communicate with that other app through another shared app group and shared file system.

For example, in some implementations, the user instruction from the process 310 can determine the scheme to include a particular site within the target app (e.g., particular display screen of the target app) based on the icon the user selects to open the linked target app. In an illustrative example, selection of a target app icon in the tab menu of the source app can be associated with the main or home screen of the target app, whereas selection of a data icon (e.g., such as IOB data) can be associated with another screen of the target app.

Example Implementations

URL Linking Data Structure

In the Apple iOS operating system environment, an app switch (i.e., change between apps in the foreground) occurs when a URL is sent to the openURL: method in the UIApplication class. An app switch causes the subsequent app to start in the foreground while suspending the initial app. The general URL format includes three primary parts: scheme, authority (user/host/port), and path, e.g., scheme://authority/path.

In some implementations of the URL linking architecture 110, the URL linking data structure (e.g., data structure 112 shown in previous example embodiments and implementations) used for switching between the source app and the target app includes a scheme that identifies the target app and an optional path including an encrypted payload (e.g., a single data payload or identifier to data stored in the shared database). An example URL linking data structure is formatted as a string, as shown in this example below where the target is an Insulin app (e.g., scheme "dxinsulin1") and the path is an encrypted string of data:

dxinsulin1:///2be2Xu8+U1+iGsPZe0PT11Mr . . .

The scheme part of the URL is used by the openURL: method in iOS to determine the target app to be started. The receiving app (i.e., the target app) gets the bundle id of the source app in the launch options dictionary (method application:openURL:options:). The bundle id is a dotted notation starting with the reverse domain of the publisher.

In some implementations of the URL linking architecture 110, the receiving app verifies that the source app is published by the source entity (e.g., the CGM app controlling entity, such as Dexcom) and check the digital signature in the payload. For example, the publisher can be verified by comparing the beginning of the bundle id with the expected reverse domain string (e.g., "com.dexcom." or "com.dexcominc.") including the trailing period. The receiving app checks the digital signature using the public key of the source app from the Shared Keychain.

In an illustrative example implementation, the scheme "dxcgm1" is used for the first app (e.g., CGM app produced by the entity Dexcom) that supports this communications protocol. The scheme for the second app (e.g., an Insulin app that supports the communication protocol) should be assigned from a table of approved target apps, e.g., in which the table is modifiable by the first app entity (e.g., Dexcom) when new target apps are to be added or existing target apps to be removed. For example, the pre-approved target app schemes can be provided in the info.plist. In some implementations, for example, based on certain operating systems, once the first app (e.g., CGM app) is operable on the computing device, new schemes should not be added (but can through an app update to the first app). For example, apps may be required to list the URL schemes with the operating system, from which the source app can search for a listed pre-approved app to link in the app's info.plist. In doing so, the source app can query the operating system (e.g., iOS) to see if there is a target app installed that supports a particular scheme. The schemes are assigned to the specific pre-approved target apps by the source app. For example, the first app can detect app installs by querying iOS for each of the schemes of the apps listed in the server config file that will be downloaded. For example, by pre-defining this list of schemes the CGM app can be frozen and released, and Insulin apps can be associated with a scheme later. For example, Table 1 is an example table for a scheme list of the first ten predefined schemes for Insulin apps.

TABLE 1 dxinsulin1
dxinsulin2
dxinsulin3
dxinsulin4
dxinsulin5
dxinsulin6
dxinsulin7
dxinsulin8
dxinsulin9
dxinsulin10

Encryption Management for URL Linking Data Structure

In some embodiments of the URL linking architecture, the source app and all target apps will generate a public/private key pair during their first time of initialization (e.g., first app linking to second app). The linked apps can store their public key in the app group's shared keychain and their private key in the target app's private keychain. The public keys in the shared keychain are identified by each app's respective bundle id. For example, the bundle identifier (bundle ID) is an identification for a software application used by the system as a domain for which it can store settings and reference the application uniquely, and is typically represented in reverse DNS notation (e.g., "com.dexcom." or "com.dexcominc."). This allows recipients of a URL message to retrieve the source app's public key using the bundle id of the source app.

In some implementations, the payload includes a dictionary of key/value pairs containing the request and its parameters. The dictionary is encoded into binary data, digitally signed, encrypted, and then encoded into a string for the path section of the URL.

Data encrypted with the target app's public key can only be decrypted by the target app because only it has the corresponding private key needed for decryption. Other apps cannot decrypt the data if they were to intercept or eavesdrop. The digital signature allows the target app to both verify the integrity of the data and its authenticity.

In some implementations, for example, the payload dictionary can be encoded into binary format in the following manner. A digital signature can be appended to the binary data, e.g., by computing a SHA-256 hash value that is encrypted with the source app's private key. The combined binary data and digital signature can be encrypted using the target app's public key. Finally, the encrypted binary data and signature can be encoded to a base 64 string for the path section of the URL.

When the URL is received by the target app, it is decoded from a base 64 string into binary data. There the payload data is separated from the digital signature. An expected hash value is computed from the payload data. The digital signature is decrypted using the source app's public key. The expected hash value is compared with the decrypted digital signature value to verify that the payload received is intact and to authenticate the source app.

To ensure privacy of the data exchanged between apps, the inter-app communications architecture 100 can be configured such that payload data sent in the URL linking structure is encrypted. In some implementations, the payload data sent in the URL linking data structure is encrypted using public key cryptography. This ensures that only the target app is able to decrypt the payload. For example, this protects personal data from intercept in cases where there is an unauthorized replacement of the target app or unauthorized apps registering for the same URL scheme.

In some implementations, each payload of the URL linking data structure includes a digital signature, e.g., to ensure the integrity and authenticity of the payload data. The digital signature allows the target app to verify that the payload data was not modified or damaged in transit. It also allows the target app to verify that the source of the payload data is the app that is expected to send requests. For example, in some embodiments, the public keys for the digital signatures are shared between apps using a shared keychain. Only apps that the source entity decides to publish in the shared app group can have access to the shared keychain.

In some implementations, the operating system (e.g., iOS for Apple devices, such as an iPhone smartphone, Apple Watch smartwatch, and iPad tablet) provides the bundle id of the source app that opened the URL. This source bundle id can be used along with the digital signature, to confirm that the source app is authorized to send URL commands.

Shared Database Architecture

In some embodiments, the disclosed inter-app communications architecture includes a shared, encrypted database that is encrypted with a private key securely held in a keychain, e.g., to ensure security and privacy of the data stored in the database. This protects database content from unauthorized modification, intercept or eavesdropping, e.g., such as when on device and also when a back-up of the device is being performed (e.g., when iTunes makes an unencrypted backup to a computer, such as in iOS based implementations).

Access to the shared database is limited to apps published by the source app controlling entity (e.g., such as Dexcom for a CGM app) by the use of the shared app group. In some implementations of the disclosed inter-app communications architecture in the iOS environment, when an app group is used, the iOS provides a shared document area that is only accessible to apps that are in the shared app group. The only apps that can join an app group are apps published with the source app entity's signing certificate and are authorized by the source app entity (e.g., via Apple's developer portal for iOS apps).

Encryption Management for Shared Database Architecture

In some implementations of the inter-app communications architecture in accordance with the present technology, the source app manages the encryption key to the shared database file. The source app keeps the database key in its private keychain. The apps in the shared app group have access to the shared database file and the shared keychain, but only apps that have a copy of the database key can access (e.g., read/write data from/to) the shared database.

For example, the target app is presumed to have generated a public/private key pair during its initial setup. The target app's public key is kept in the shared app group's shared keychain, and the target app's private key is kept in the target app's (private) keychain. The target app's public key is available to the source app in the shared keychain.

In implementations when the user selects a target app to "link", a copy of the database key is made available to target apps in the shared app group by encrypting the copy of the database key with the "linked" target app's public key and storing it in the shared keychain. All apps in the shared app group have access to the shared keychain, but only the selected (i.e., linked) target app(s) has the private key needed to decrypt the database key.

In implementations when the user selects the linked target app to "unlink", the source app removes the database key from the shared keychain and then rekeys the database to a new key. The source app updates the database key saved in its private keychain.

Example Application: CGM App and Insulin App(s)

In some implementations in accordance with the present technology, the inter-app communication architecture can be applied to various types of app groups (e.g., two or more independent software applications) for integrating their data communication and protection capabilities and managing their inter-app transitions on the back end for, while providing a consistent and smooth end-user interface and experience on the front end. In one example application, the source app is a mobile medical app (e.g., a CGM app) that will exchange data with a second mobile application that may or may not be a mobile medical app of the same class (e.g., an Insulin app). It is noted that a mobile medical app is a software application operated on a mobile device that meets the definition of "device" in section 201(h) of the Federal Food, Drug, and Cosmetic Act (FD&C Act); and either is intended (i) to be used as an accessory to a regulated medical device; or (ii) to transform a mobile platform into a regulated medical device. For example, see Mobile Medical Applications Guidance for Industry and Food and Drug Administration Staff, issued on Feb. 9, 2015. In this example application, the Insulin app is developed by an insulin delivery device manufacturer that communicates with their insulin pump or pen. The data exchange can be facilitated by the disclosed embodiments of the inter-app communication architecture. This will enable the CGM app to read, store and display certain insulin information for the patient user, e.g., diabetic person using (i) a continuous glucose sensor device with CGM app and (ii) an insulin delivery device such as an insulin pump or pen. The CGM app can upload the CGM data and insulin data to a real-time server system for secondary display and/or for retrospective diabetes management software applications (e.g., operated by the entity providing the CGM app and/or third-party entities). The inter-app communication protocol can allow (i) the CGM device and CGM app manufacturer and (ii) the Insulin device and Insulin app manufacturer to design and validate their respective apps independently, while sharing data through a standardized interface provided by one entity. This structure allows for a compatibility testing process to validate the data sharing between entities independently.

Figure 4A:
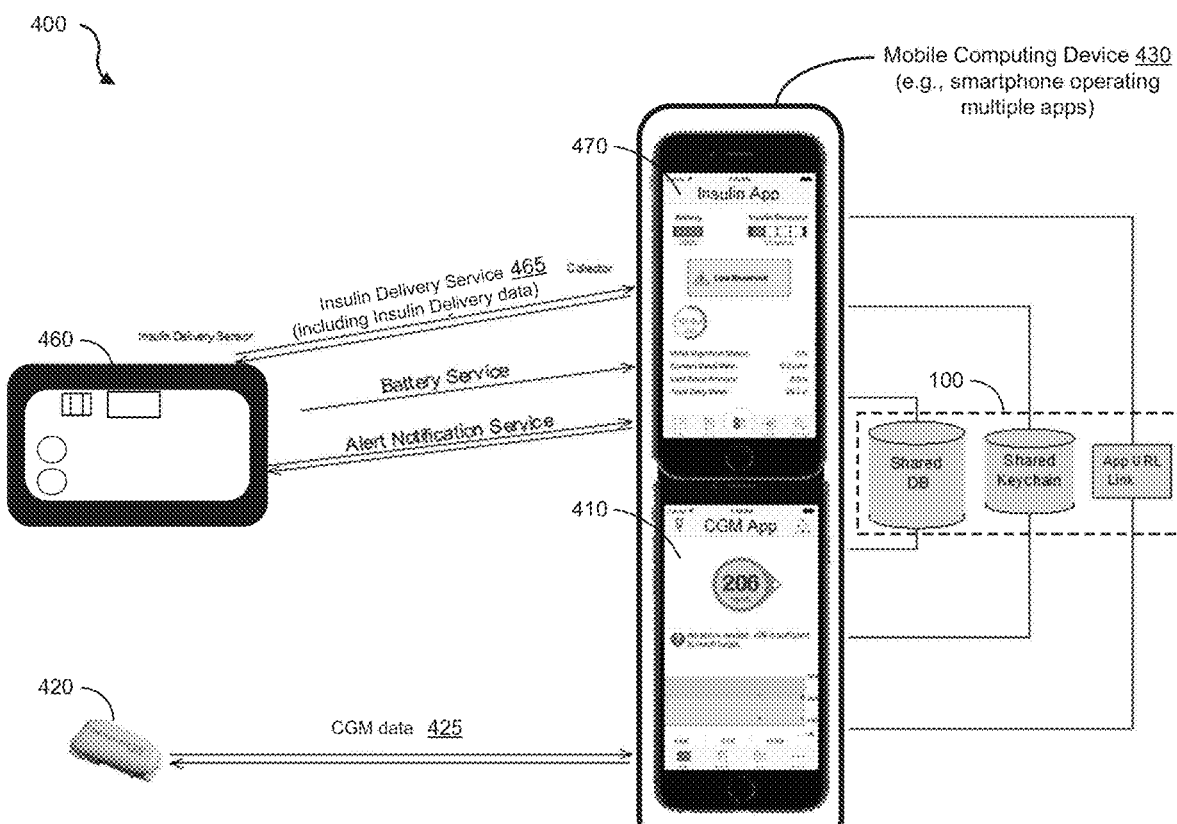
FIG. 4A is a diagram of an example inter-app and data communications architecture in accordance with some implementations of the present technology between a CGM device, insulin delivery device, and a CGM app and Insulin app.

FIG. 4A is a diagram of an example diabetes management system 400 including a CGM device 420, an insulin delivery device 460 (e.g., insulin pump) and mobile computing device 430 (e.g., smartphone) operating various embodiments of the inter-app and data communications architecture 100 between a source app, e.g., CGM app 410, and a target app, e.g., Insulin app 470, in accordance with some implementations of the present technology. In this example, the mobile computing device 430 includes and is able to operate a plurality of apps including the CGM app 410 and 470. The diagram depicts the data communications between the CGM app 410 and the Insulin app 470 on the smartphone 430 in communication with their respective medical devices, i.e., the CGM device 410 and the insulin delivery device 460, respectively. The diagram illustrates that the CGM app 410 and Insulin app 470 communicate data using the inter-app and data communications architecture 100 including the URL linking architecture 110, shared database 120 and encryption architectures operable to protect, store and transfer data between the CGM app 410 and Insulin app 470.

Figure 4B:
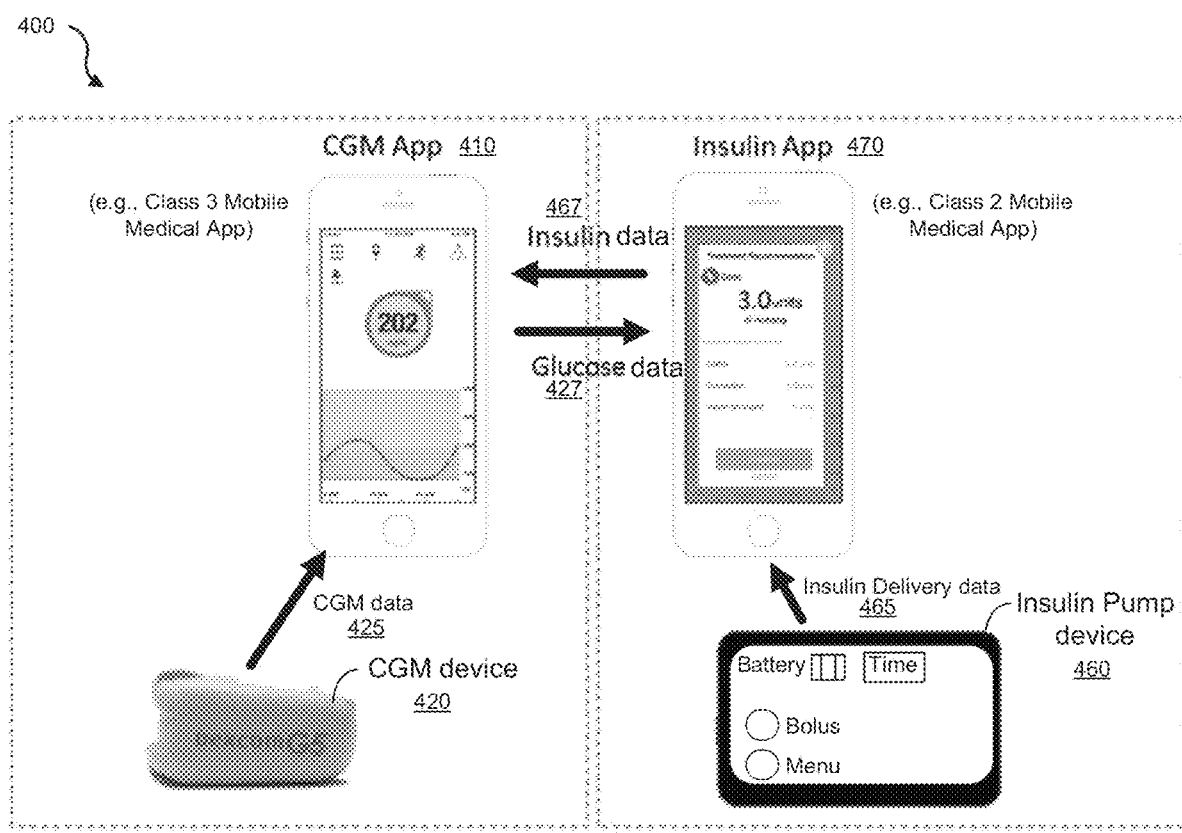
FIG. 4B is a diagram of an example system configuration for a CGM device and CGM app with an insulin delivery device (e.g., insulin pump or pen) and Insulin app in accordance with some implementations.

FIG. 4B is a diagram of an example system configuration of the diabetes management system 400 for the CGM device 420 with the CGM app 410 and the insulin delivery device 460 with the Insulin app 470 in accordance with some implementations of the present technology. In this example, the CGM app 410 is shown as a class 3 mobile medical app that receives CGM data 425 from the CGM device 420 and processes the CGM data 425 to produce processed glucose data 427. Similarly, the Insulin app 470 is shown as a class 2 mobile medical app that receives insulin delivery data 465 from the insulin delivery device (e.g., insulin pump device) 460 and processes the insulin delivery data 465 to produce processed insulin data 467. Using the disclosed inter-app communications architecture, for example, the CGM app 410 is able to share the processed glucose data 427 with and receive the processed insulin data 467 from a partner medical device app, the Insulin app 470.

The CGM app 410 provides an alternative user interface for users of the CGM device 420, e.g., besides an interface on the sensor device or a receiver dedicated to receiving data from the sensor device. In some embodiments, for example, the CGM app 410 is operable on a compatible, BLE-enabled smartphone device 430. In such embodiments, the CGM app 410 communicates via BLE radio with the transmitter of the continuous glucose sensor device 420. The CGM app 410 sends calibration information to the transmitter, receives the continuous glucose measurement from the transmitter, displays glucose information including in the form of a trend graph on a display screen of the smartphone, and alerts patients when glucose is out of a predetermined normal range.

The CGM app 410 is included in a continuous glucose monitoring system, which includes the continuous glucose sensor (CGM) device 420 including a sensor unit, a data processing unit and a transmitter unit on the device; and a receiver device such as a dedicated receiver device to display the processed glucose data or the mobile computing device 430 (e.g., smartphone) operating the CGM app 410. In some implementations, the continuous glucose monitoring system includes multiple receiving devices. The sensor unit of the CGM device 420 is inserted into subcutaneous tissue where it continuously measures glucose concentration. The data processing unit is connected to the sensor unit and uses an onboard algorithm to convert the sensor signals into glucose data, which is provided to the transmitter to wirelessly communicate with the receiver device and/or the CGM app 410, e.g., using Bluetooth Low Energy (BLE) technology. For example, the CGM device 420 sends the glucose data (e.g., a new glucose value) every 5 minutes, and receives reference capillary blood glucose measurements when entered by the user for calibration. The receiver device and CGM app 410 display the glucose readings and alert the user when glucose levels are outside of a target zone. In some implementations, the alerts are generated by the CGM app 410 executed on the smartphone when the received glucose data exceeds a predetermined threshold. The CGM app 410 can also provide connectivity to the remote monitoring service (e.g., Dexcom Share service), e.g., for secondary display on a Remote Monitoring app on a remote monitor's smartphone (e.g., the Dexcom Follow App). The CGM app 410 integrates the functionality of the remote monitoring system for a host (e.g., Dexcom Share), allowing patient CGM data to be shared with remote monitors (e.g., host-selected individuals, like friends and family) in real time.

As noted previously, the CGM app 410 in FIG. 4B is a class 3 mobile medical app and the Insulin app 470 is shown as a class 2 mobile medical app. In this way, one app, in this case the CGM app 410, only handles functionality related to its purview, e.g., only handles monitoring of glucose values, e.g., receiving, performing calibration if such is not performed on a transmitter, and display/handling of glucose concentration values.

Figure 4C:
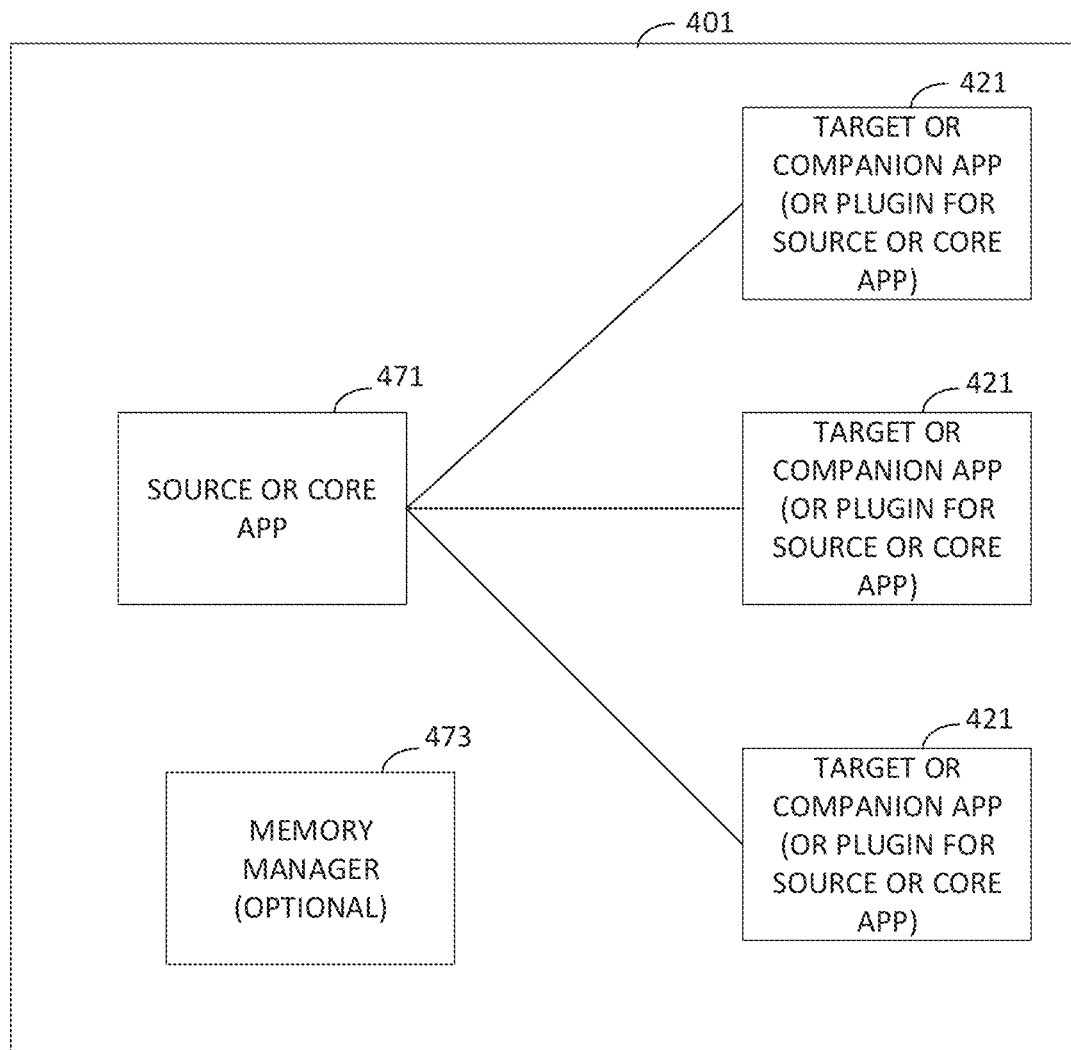
FIG. 4C is a diagram illustrating an arrangement of apps, including source and target apps, operating within a computing environment.

FIG. 4C illustrates an exemplary implementation in which a mobile device 400 includes a source or core app 471 in communication with one are more target or companion apps 421. The source or core app 471 performs functions related to its purview as noted above, e.g., related to receiving and displaying CGM values. The target or companion apps 421 perform functions related to their respective purviews as well, e.g., related to medicament delivery, bolus calculation, and so one.

Having the source or core app perform only these functions generally simplifies memory management of the app and also provides other benefits, including related to the validation of the app from a regulatory perspective. A subset or even in some implementations all other functionality may be performed by one or more of the other target or companion apps. In one implementation, the source app is enabled to handle the class III medical device concerns, e.g., calibration, management of alerts and alarms, etc., and the remainder of the functionality is handled by companion apps, e.g., which may have lesser regulatory concerns, e.g., may be class II or even class II exempt applications.

While the target or companion apps are shown in FIG. 4C as residing on the same device as the source or core mobile app, such co-location is not necessary. For example, the source app could reside on a mobile device while the target app could reside on a wearable, or vice-versa. In another example, the source app could be on a receiver and the target app could reside on a smart phone. Other variations will also be understood given this teaching.

Systems and methods according to such principles provide multiple benefits. For example, such systems and methods provide significantly enhanced operation of the computing device itself, by permitting target apps to be maintained in a more up-to-date fashion, without having to constantly resubmit the source app upon each update. Other advantages include that such systems and methods reduce "function bloat" of the source application, allowing the same to be maintained in a leaner fashion, reducing errors and allowing processing to occur more rapidly than otherwise, which in turn allows the more rapid delivery of life-affecting and in some cases life-saving alerts and alarms.

Other technological benefits include the ability to explore novel or niche target applications without compromising the source app or other target apps. The same enabled a separation of a "dedicated medical application" from a "consumer application".

Other benefits include that systems and methods according to present principles may enable reduced regulatory classification of target apps containing user-desired functionality, speeding up the product development cycle for both core and target apps. Such systems and methods improve the user experience in both the source app and the target app.

From the user's perspective, the target or companion apps seamlessly integrate with the source or core app using the techniques and methods described herein, e.g., as shown in the attached figures and accompanying text. In addition, here it is noted that implementing the seamless integration depends on the particular instantiation. Using two mobile apps as an example, the source app may be instantiated and may continue to operate in the background, but the user may primarily interface with their preferred target app. Prompts for actions to take in the source app can be delivered to the target app, and even a launching of the source app can be achieved through a button press in the target app, as described in systems and methods above, thus reducing or eliminating the necessity of the user having to hunt down the source app or go back to the home screen at all. Upon completing the required source app function, the user can be automatically returned to the target app.

In one variation of the above implementation, instead of being embodied by a source app in communication with multiple target apps, the system and method may be embodied by a source or core app in communication with one or more plug-ins (see again FIG. 4C) that provide the different functionality desired. In this way, it may be that only the core app needs to be certified to a certain level. It is noted in this regard that in many cases, particularly user-intensive app functionality is not part of the portion that requires particularly rigorous certification. For example, the calculation of a CGM value may require high certification, while functionality related to user acknowledgement of alarms may require comparatively less so, and thus the same may be accomplished by a plug in. The same may be true of providing different visualizations, providing convenient methods for food entry, providing certain types of decision support, and the like, which have a higher level of user interaction but a lower level of regulatory concern.

The systems and methods according to present principles, and in particular those with respect to FIG. 4C, may interoperate well with other embodiments disclosed here, and examples are thus provided. In particular, by providing the linking architecture of FIGS. 1-4B, a seamless experience may be provided to the user, negating the need to exit out of a source app in order to enter a target app. As another benefit, linking each of two or more apps to a common data store allows faster and more efficient processing of data by such multiple connected apps, while also reducing data storage requirements. Finally, the modularization of FIG. 4C may be enhanced by providing a common visualization theme for common visualization elements, particularly that the user comes to rely on as acting in a particular way, reacting in a particular way, and so on. For example, a source app may be a CGM app, while a target app may operate a bolus calculator or medicament delivery device. Each may display CGM data. The display of the CGM data may be via a common display scheme, e.g., with a numerical value of glucose concentration situated within, if the glucose is rising or falling, an arrow directed up or down, respectively, with the slope of the arrow indicating the rate of change of the rise or fall. The bolus calculator may have a comparatively smaller display of the glucose indication, due to the need to show also the bolus calculation results, but the use of a common scheme can ensure the user feels comfortable with the reliability, consistency, and uniformity, of the various displays, and is not confused by multiple portrayals of the same data in different ways. In the same way, the user need not learn how to interpret multiple app displays.

Figure 4D:
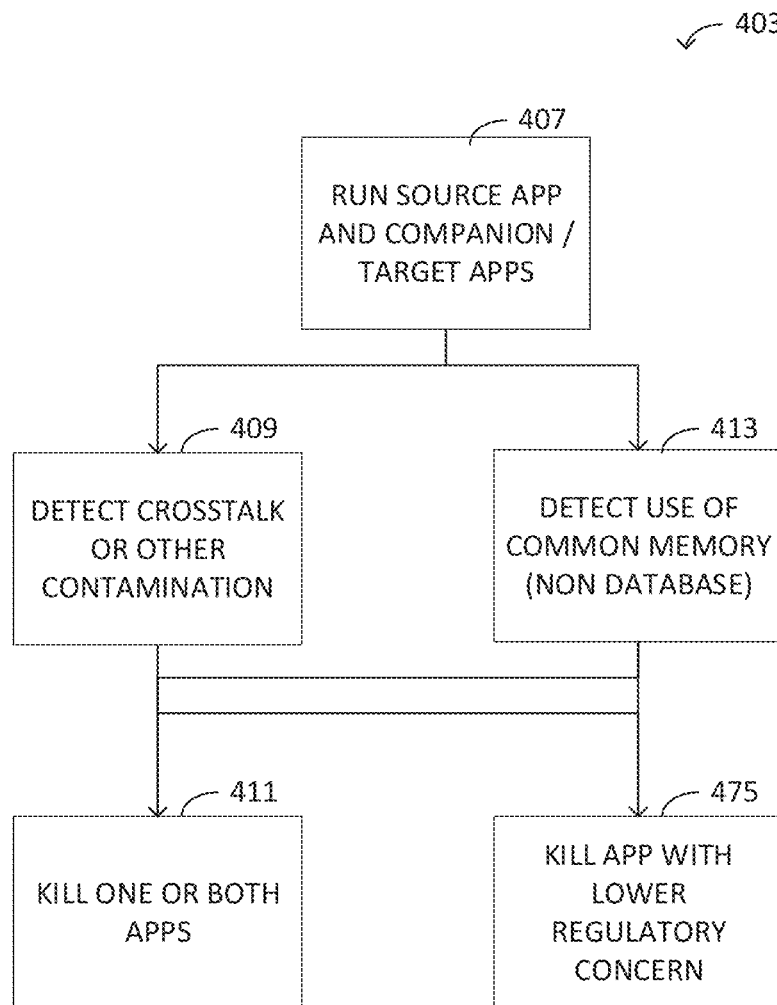
FIG. 4D is a flowchart of a method according to present principles.

One method is indicated by the flowchart 403 of FIG. 4D. In this flowchart, a source app and a companion or target app are both running, or one is running and another is being instantiated or the like.

Generally, an individual app, either source or target, will not have sufficient permissions to allow control of other app's memory usage. However, in some implementations, where such permissions are granted, a source or target app may perform a step of memory management using a memory manager 473 (see FIG. 4C) to ensure that memory used by one app is not accessed or "contaminated" by another app (except for mutual access of a shared database) (step 409), or a step may occur of detecting usage of a common memory location by both apps (step 413). Such may be possible, however, if the apps are implemented on a dedicated receiver or even a dedicated smart mobile device. If such cross-talk is detected, (step 409), or if usage of a common memory location is detected (step 413), then one or both apps may be killed or otherwise terminated (step 411), or in another implementation the app with the lower regulatory concern may be kill or terminated. Other partitioning schemes may also be pursued, so as to allow no app crosstalk, and thus to ensure that a highly regulated app is not affected by the operation of a lower regulated app.

In yet another implementation, in lieu of separating the apps in memory, the higher regulated app may be configured to, upon detecting that a lower regulated app is affecting its operation, kill or terminate operation of the lower regulated app, so as to maintain the effective and accurate operation of the higher regulated app, and thus to maintain the safety of the patient.

Figure 4E:
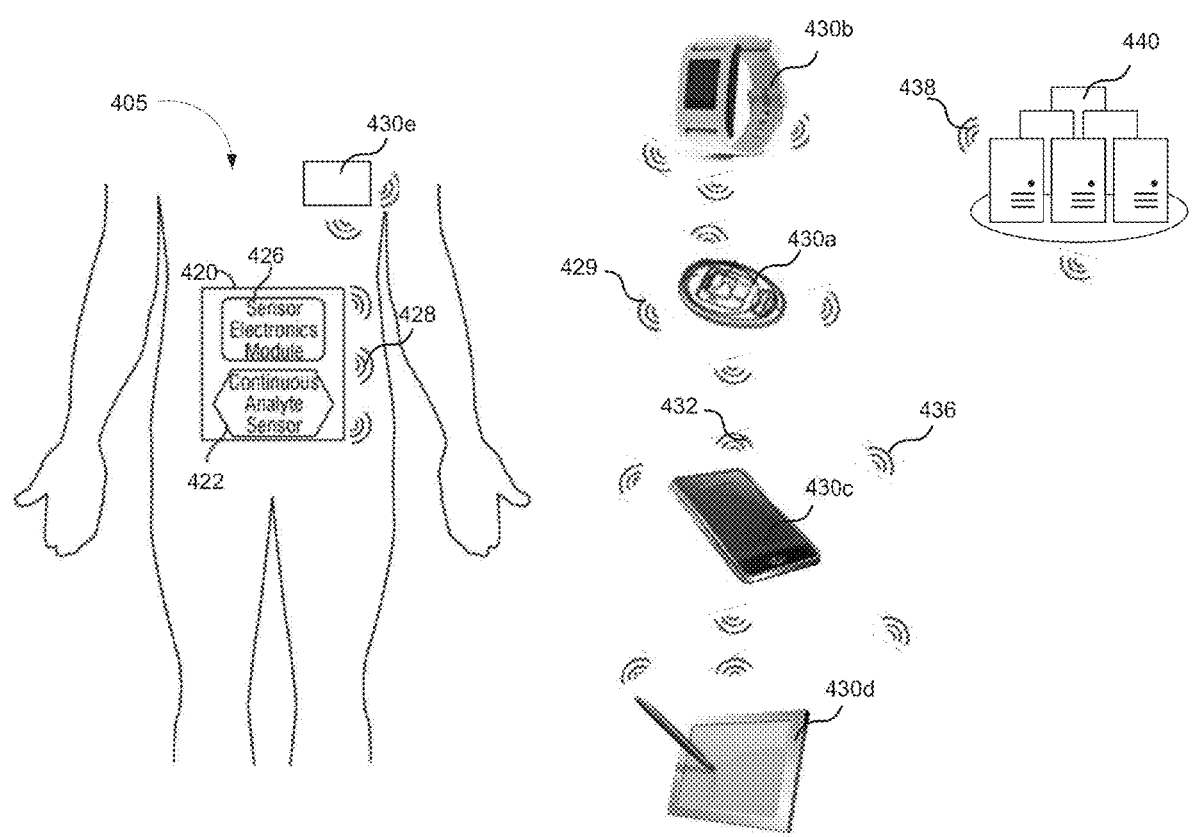
FIG. 4E is a diagram illustrating an example embodiment of a continuous analyte sensor system including a CGM device communicating with at least one mobile computing device in accordance with various technologies described in the present disclosure.

FIG. 4E is a diagram illustrating an example embodiment of a continuous analyte sensor system 405, such as a continuous glucose monitoring system including the CGM device 420, communicating with at least one mobile computing device 430 in accordance with various technologies described in the present disclosure. The example continuous analyte monitoring system 405 includes the continuous glucose monitoring (CGM) device 420 operatively connected to a patient user and a plurality of mobile computing devices 430a-e that may be operated by the patient user according to certain aspects of the present disclosure. It should be noted that mobile computing device 430e alternatively or in addition to being a display device, may be a medicament delivery device (e.g., such as the insulin delivery device 460) that can act cooperatively with the CGM device 420 to deliver medicaments to host. The CGM device 420 may include a sensor electronics module 426 and a continuous analyte sensor 422, e.g., a continuous glucose sensor, associated with the sensor electronics module 426. The sensor electronics module 426 may be in direct wireless communication with one or more of the plurality of the mobile computing devices 430a-e via wireless communications signals. As will be discussed in greater detail below, mobile computing devices 430a-e may also communicate amongst each other and/or through each other to CGM device 420. For ease of reference, wireless communications signals from CGM device 420 to mobile computing devices 430a-e can be referred to as "uplink" signals 428. Wireless communications signals from, e.g., mobile computing devices 430a-e to the CGM device 420 can be referred to as "downlink" signals 429. Wireless communication signals between two or more of mobile computing devices 430a-e may be referred to as "crosslink" signals 432. Additionally, wireless communication signals can include data transmitted by one or more of mobile computing devices 430a-d via "long-range" uplink signals 436 (e.g., cellular signals) to one or more remote servers 440 or network entities, such as cloud-based servers or databases, and receive long-range downlink signals 438 transmitted by remote servers 440.

The sensor electronics module 426 includes sensor electronics that are configured to process sensor information and generate transformed sensor information, e.g., to produce the CGM data 425. In certain embodiments, the sensor electronics module 426 includes electronic circuitry associated with measuring and processing data from continuous analyte sensor 422, including prospective algorithms associated with processing and calibration of the continuous analyte sensor data. The sensor electronics module 426 can be integral with (non-releasably attached to) or releasably attachable to the continuous analyte sensor 422 achieving a physical connection therebetween. The sensor electronics module 426 may include hardware, firmware, and/or software that enables analyte level measurement. For example, the sensor electronics module 426 can include a potentiostat, a power source for providing power to continuous analyte sensor 422, other components useful for signal processing and data storage, and/or a telemetry module for transmitting data from itself to one or more mobile computing devices 430a-e. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entirety for all purposes.

Mobile computing devices 430a-e may be configured for operating a plurality of apps, including the CGM app 410 and the Insulin app 470, which can facilitate the displaying, alarming, and/or basing medicament delivery on the sensor information that has been transmitted by the sensor electronics module 426 (e.g., in a customized data package that is transmitted to one or more of mobile computing devices 430a-e based on their respective preferences). Each of the mobile computing devices 430a-e can include a display such as a touchscreen display for displaying sensor information to a user (most often host or a care taker/medical professional) and/or receiving inputs from the user. In some embodiments, the mobile computing devices 430a-e may include other types of user interfaces such as a voice user interface instead of or in addition to a touchscreen display for communicating sensor information to the user of the mobile computing devices 430a-e and/or receiving user inputs. In some embodiments, one, some or all of the mobile computing devices 430a-e are configured to display or otherwise communicate the sensor information as it is communicated from the sensor electronics module 426 (e.g., in a data package that is transmitted to respective display devices 430a-e), without any additional prospective processing required for calibration and real-time display of the sensor information.

Figure 4F:
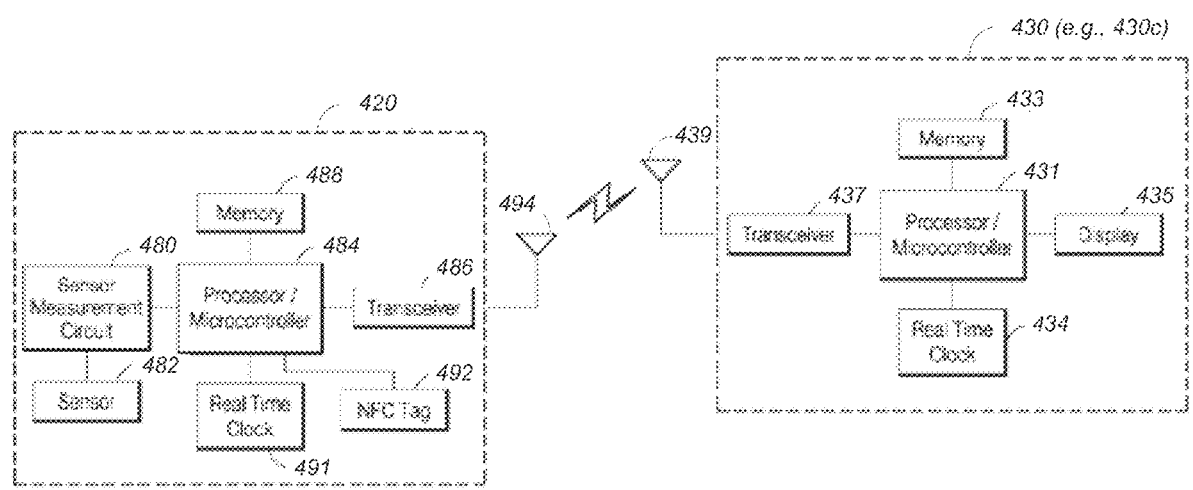
FIG. 4F is a block diagram illustrating example components of an example CGM device and at least one of the plurality of mobile computing devices depicted in FIG. 4E, as well as the communications therebetween.

In the example embodiment of FIG. 4F, one of the plurality of mobile computing devices 430a-e may be a custom medical device receiver and/or display device 430a specially designed for displaying certain types of displayable sensor information associated with analyte values received from the sensor electronics module 426 (e.g., a numerical value and an arrow, in some embodiments). In some embodiments, one of the plurality of mobile computing devices 430a-e may be a smartphone 430c based on the Apple iOS, Android, or other mobile device operating system or other operating system, a palm-top computer and the like, e.g., in which the smartphone or other mobile computing device 430c may have a relatively larger display and be configured to display a graphical representation of the continuous sensor data (e.g., including current and historic data). Other mobile computing devices can include other hand-held devices, such as a tablet 430d, a smartwatch 430b, a medicament delivery device 430e (e.g., an medicament delivery pump or pen), a blood glucose meter, and/or a desktop or laptop computer.

As alluded to above, because the different mobile computing devices 430a-e provide different user interfaces, content of the data packages (e.g., amount, format, and/or type of data to be displayed, alarms, and the like) can be customized (e.g., programmed differently by the manufacture and/or by an end user) for each particular display device and/or display device type. Accordingly, in the example embodiment of FIG. 4E, one or more of mobile computing devices 430a-e can be in direct or indirect wireless communication with the sensor electronics module 426 to enable a plurality of different types and/or levels of display and/or functionality associated with the sensor information, which is described in more detail elsewhere herein.

Generally, the continuous analyte sensor 422 may be an implantable analyte (e.g., glucose) sensor that utilizes amperometric electrochemical sensor technology to measure glucose concentration. Electrodes comprising continuous analyte sensor 422 may include a working electrode, a counter electrode, and a reference electrode. In one embodiment, for example, the counter electrode is provided to balance the current generated by the species being measured at the working electrode. In the case of a glucose oxidase based glucose sensor, the species being measured at the working electrode is $H_2O_2$. Glucose oxidase catalyzes the conversion of oxygen and glucose to hydrogen peroxide and gluconate according to the following reaction:

Glucose+$O_2$ Gluconate+$H_2O_2$

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons ($2H^+$), two electrons ($2e$) and one oxygen molecule ($O_2$).

In some embodiments, additional electrodes can be included within the assembly, for example, a three-electrode system (working, reference, and counter electrodes) and an additional working electrode (e.g., an electrode which can be used to generate oxygen, which is configured as a baseline subtracting electrode, or which is configured for measuring additional analytes). U.S. Pat. No. 7,081,195, U.S. Patent Publication No. 2005/0143635 and U.S. Patent Publication No. 2007/0027385, each of which are incorporated herein by reference, describe some systems and methods for implementing and using additional working, counter, and reference electrodes. In some embodiments where two or more working electrodes are provided, the second working electrode may be configured to be substantially similar to the first working electrode, but without an enzyme disposed thereon. In this way, the baseline signal can be determined and subtracted from the first signal to generate a difference signal, i.e., a glucose-only signal that is substantially not subject to fluctuations in the baseline or interfering species on the signal, such as described in U.S. Patent Publication No. 2005/0143635, U.S. Patent Publication No. 2007/0027385, and U.S. Patent Publication No. 2007/0213611, and U.S. Patent Publication No. 2008/0083617, which are incorporated herein by reference in their entirety.

FIG. 4E is a block diagram illustrating example components of CGM device 420 and at least one of the plurality of mobile computing devices 430 (e.g., the smartphone 430c), as well as the communications therebetween. The CGM device 420 may include an implantable continuous analyte sensor 482 (one embodiment of continuous analyte sensor 422 of FIG. 4E) coupled to a sensor measurement circuit 480 for processing and managing sensor data. The sensor measurement circuit 480 may be coupled to a processor 484 (e.g., part of sensor electronics module 426 in FIG. 4E). In some embodiments, the processor 484 may perform part or all of the functions of the sensor measurement circuit 480 for obtaining and processing sensor measurement values from the implantable continuous sensor 482. The processor may be further coupled to a radio unit or transceiver 486 (e.g., part of sensor electronics module 426 in FIG. 4E) for sending sensor information to and receiving requests and commands from an external device, such as mobile computing device 430 (e.g., smartphone 430c), which is used to display or otherwise provide the glucose information to a user. As used herein, the terms "radio unit" and "transceiver" are used interchangeably and generally refer to a device that can wirelessly transmit and receive data. The transmission and receipt of such data further includes utilization of antenna 494. It should be noted that more than one antenna may be utilized in the CGM device 420. The CGM device 420 can include a memory 488 (e.g., part of sensor electronics module 426 in FIG. 4E) for storing and tracking sensor information. In some embodiments, for example, the CGM device 420 may further include a real time clock (RTC) 491 (e.g., part of sensor electronics module 426 in FIG. 4E) for managing the tracking sensor information. In some embodiments, the CGM device 420 further includes near field communication (NFC) capability. In some embodiments, an NFC tag 492 is implemented/integrated into the electronics in the CGM device 420. While not shown explicitly, NFC tag 492 may be included as part of transceiver of the CGM device 420.

Wireless communication protocols may be used to transmit and receive data between the CGM device 420 and the mobile computing device 430. The wireless communication protocol used may be designed for use in a wireless sensor network that is optimized for periodic and small data transmissions (that may be transmitted at low rates if necessary) to and from multiple devices in a close range (e.g., a personal area network (PAN)). For example, the wireless communication protocol may be optimized for periodic data transfers where transceivers may be configured to transmit data for short intervals and then enter low power modes for long intervals. The wireless communication protocol may have low overhead requirements both for normal data transmissions and for initially setting up communication channels (e.g., by reducing header overhead) to reduce power consumption. In some embodiments, burst broadcasting schemes (e.g., one way communication) may be used. This may eliminate overhead required for acknowledgement signals and allow for periodic transmissions that consume little power.

The wireless communication protocol may further be configured to establish communication channels with multiple display devices, e.g., two or more of mobile computing devices 430a-e, while implementing interference avoidance schemes. In some embodiments, the wireless communication protocol may make use of adaptive isochronous network topologies that define various time slots and frequency bands for communication with several ones of the mobile computing devices 430a-e. The wireless communication protocol may thus modify transmission windows and frequencies in response to interference and to support communication with multiple ones of mobile computing devices 430a-e. Accordingly, the wireless protocol may use time and frequency division multiplexing (TDMA) based schemes. The wireless communication protocol may also employ direct sequence spread spectrum (DSSS) and frequency-hopping spread spectrum schemes. Various network topologies may be used to support short-distance and/or low-power wireless communication such as peer-to-peer, start, tree, or mesh network topologies such as Wi-Fi, Bluetooth and Bluetooth Low Energy (BLE). The wireless communication protocol may operate in various frequency bands such as an open ISM band such as 2.4 GHz. Furthermore, to reduce power usage, the wireless communication protocol may adaptively configure data rates according to power consumption Like antenna 494 of the CGM device 420, a corresponding antenna 439 is utilized in the mobile computing device 430 for transmission/receipt of data to/from the CGM device 420. Again, one or more antennas in addition to antenna 434 may be used to allow for the various aforementioned communication protocols to operate at their requisite frequencies/frequency ranges.

The mobile computing device 430 may be used for alerting and providing sensor information to a user, such as the patient user or a caregiver of the patient user, and may include a processor 431 for processing and managing sensor information. The mobile computing device 430 may include a display 435, a memory 433, and a real time clock 434 for displaying, storing and tracking sensor information, respectively. The mobile computing device 430 may further include a radio unit or transceiver 437 for receiving sensor information and for sending requests, instructions, and data to the CGM device 420. The transceiver 437 may further employ a wireless communication protocol. The memory 433 may also be used for storing an operating system and/or a custom (e.g., proprietary) application designed for wireless data communication between a transceiver, e.g., transceiver 486 and the mobile computing device 430. The memory 433 may be a single memory device or multiple memory devices and may be a volatile or non-volatile memory for storing data and/or instructions for software programs and applications. The instructions may be executed by the processor 431 to control and manage the transceiver 437. In some embodiments, for example, it should be understood that in the case of the mobile computing device 430*e*, which may be a medicament delivery device in addition to or instead of a display device, the alerts and/or sensor information provided by continuous analyte sensor 422 vis-à-vis sensor electronics module 426, can be used to initiate and/or regulate the delivery of a medicament to the patient user.

In some embodiments, when a standardized communication protocol is used, commercially available transceiver circuits may be utilized that incorporate processing circuitry to handle low level data communication functions such as the management of data encoding, transmission frequencies, handshake protocols, and the like. In these embodiments, processors 484 and 431 do not need to manage these activities, but rather provide desired data values for transmission, and manage high level functions such as power up or down, set a rate at which messages are transmitted, and the like. Instructions and data values for performing these high level functions can be provided to the transceiver circuits 486 and 437, respectively, via a data bus and transfer protocol established by the manufacturer of the transceiver circuits 486 and 437.

In accordance with some implementations of the CGM device 420, for example, the CGM device 420 gathers and processes analyte measurements from the continuous analyte sensor 482, and periodically sends sensor information representative of the analyte measurements to the mobile computing device 430. Measurements are gathered and transmitted over the life of continuous analyte sensor 482 (e.g., in the range of 1 to 30 days or more). New measurements may need to be transmitted often enough to adequately monitor analyte levels. Rather than having the transmission and receiving circuitry of each of the CGM device 420 and mobile computing device 430 continuously communicating, the CGM device 420 and mobile computing device 430 may regularly and periodically establish a communication channel between them. Thus, the CGM device 420 can communicate wirelessly with mobile computing device 430 at predetermined time intervals. The duration of the predetermined time interval can be selected to be long enough so that the CGM device 420 does not consume too much power by transmitting data more frequently than needed, yet frequent enough to provide substantially real-time sensor information (e.g., measured analyte values) to one or more of mobile computing device 430*a-e* for output (e.g., display) to a user. While the predetermined time interval is every five minutes in some embodiments, it is appreciated that this time interval can be varied to be any desired length of time. It should be noted that other contemplated embodiments involve irregular or aperiodic transmissions of sensor information, e.g., from the CGM device 420 to one or more of mobile computing device 430*a-e*.

Some implementations of the inter-app communications architecture 100 of the disclosed technology can provide several advantages for patient users managing their diabetic conditions using a glucose monitoring app, such as the CGM app 410, and a linked, independent app connected through one or more embodiments of the inter-app communications architecture 100, such as an insulin delivery device app (Insulin app 470), bolus calculator app, and/or other health tracking app. The example system configuration for the CGM app 410 and Insulin app 470 in accordance with some implementations of the present technology can provide discretion, convenience and confidence for diabetes management. For example, with CGM and insulin data visualization on a patient user's mobile device, i.e., a single app on a single device, the patient user can discreetly and easily make more informed treatment decisions. For example, the example system configuration is envisioned to reduce or eliminate the need for the patient user to pull out his/her insulin pump to see his/her status—by implementing one or more embodiments of the inter-app communications architecture of the disclosed technology, the patient user can view insulin data discreetly on his/her mobile device via the disclosed mobile medical app alongside his/her CGM data. The example system configuration for the CGM app 410 and Insulin app 470 can provide discretion, safety and peace of mind for diabetes management. For example, alert thresholds and sounds can be customized for different times of the day, affording the patient user increased discretion and safety when he/she needs it the most. In some implementations, the system can utilize remote monitoring communication technology for patient users to share data with selected remote monitors, e.g., including family members, friends, and ancillary caregivers. For example, a system comprising independent CGM and insulin delivery devices and apps that employ various embodiments of inter-app communication architecture of the present technology can provide peace of mind to the diabetic patient users by sending information about the patient user's glucose, insulin and meals to his/her loved ones (e.g., remote monitors) so that they know what treatment decisions the patient user has made. The example system configuration for the CGM app 410 and Insulin app 470 can provide versatility, ease of use and confidence for diabetes management. For example, in some implementations, the CGM app 410 can include an enhanced bolus calculator to help the patient user make more accurate/data-driven insulin dosing decisions while actively monitoring their glucose. For example, in some implementations, the CGM app 410 facilities multiple types of insulin treatment users, e.g., such as patient users who treat by multiple daily injections ("MDI users"), in which the MDI users can quickly and easily log their insulin in the disclosed mobile medical app, allowing them to visualize Insulin on Board (JOB) along with their continuous glucose data. The example system configuration for the CGM app 410 and Insulin app 470 can provide convenience in a way that is envisioned to improve outcomes for their diabetes management. For example, in some implementations, the CGM app 410 allows patient users to view and dismiss glucose notifications in the manner most convenient for them, e.g., from their smartphone device's lock screen or their smartwatch. This provides the patient user with convenience to only open the CGM app 410 when more information is needed or to make a treatment decision. For example, meal and exercise data entered into third-party applications, e.g., Healthkit-supported apps or linked apps using example embodiments of the inter-app communications architecture 100, can be viewed in the glucose trend graph of the CGM app 410, e.g., helping the patient user better understand what impacts his/her glucose patterns. For example, the disclosed system can automatically send all of the patient user's CGM, insulin, meal, and/or event data to a cloud-based reports system, which allows the patient user to access the data anywhere, on any device, e.g., even at the doctor's office.

Some implementations of the CGM app 410 can provide the following example functionalities to enhance the end-user's experience and its utility for the user's glucose and health management. For example, by employing various embodiments of the disclosed inter-app communications architecture 100 with one or more Insulin apps 470, the CGM app 410 can provide integrated data visualization capabilities of most-valuable medical data and health information. The CGM app 410 can display features integrating the glucose and insulin data in a specialized way. For example, the CGM app 410 is configured to present insulin on board (JOB) data and other relevant insulin data from approved Insulin apps 470 (e.g., 'partner apps') or from user-entry integratable and displayable along a with continuous glucose data (e.g., such as a glucose level trend graph) in an easy to understand format that provides the user with sufficient information to instantly decide whether treatment is necessary. For example, the medical data and health information (e.g., insulin data, meal data, exercise data, etc.) can be aggregated into the mobile medical app by the disclosed inter-app communications methods and platforms, and are integrated with acquired CGM data by the data processing methods of the CGM app 410. In some implementations, for example, the CGM app 410 can manage presentation of the data using a prominent tool of the operating system (e.g., Today Widget of Apple iOS) of the patient user's smartphone 430c or wearable device 430b (e.g., Apple Watch), enabling the user to glanceably view glucose and insulin data and make instant decisions for their treatment. Moreover, in some implementations of the CGM app 410, for example, the CGM app 410 can include an alert schedule tool (also referred to as Alert Profiles) to allow patient users to set up two distinct schedules for their alerts, thereby allowing more discretion and more protection when it is needed the most. In some implementations of the CGM app 410, for example, the CGM app 410 enables patient users to acknowledge alerts and notifications on their smartphone's lock screen and/or on their connected wearable device (e.g., Apple Watch). In some implementations, for example, the CGM app 410 can include an Escalating Mute Override Alert sequence to allow patient users to hear critical alarms even when their smartphone is muted or turned to very low volume.

The CGM app 410 can provide further functionalities designed to empower the patient user to manage their glucose state, treatment, and overall health. The CGM app 410 can provide an easy-to-use and enhanced Bolus Calculator, set up by a health care professional (HCP) and informed by the CGM trend, which will be available for both insulin pump and MDI users. The CGM app 410 can provide the insulin data and event entry data (received into the mobile medical app by the disclosed inter-app communications methods and platforms) to the Cloud (e.g., uploaded to servers in the Cloud). This data can subsequently be used for retrospective data processing by other applications and/or devices, e.g., such as Dexcom Clarity or other software applications for managing retrospective data. The CGM app 410 can provide the insulin data and event entry data (received into the mobile medical app by the disclosed inter-app communications methods and platforms) to servers that manage real-time data (e.g., real-time glucose data), which can be provided to remote monitors of the patient user's medical data (e.g., caregivers selected by the patient user, including family members, friends, etc.) that remotely monitor the patient user's condition using a mobile software application. For example, the CGM app 410 will be capable of pulling in diabetes-relevant user-logged data from Healthkit or other sources, to be viewed on the landscape trend and also uploaded to the Dexcom servers for use by a remote monitoring app and to enhance statistical reports, e.g., by Dexcom Clarity.

Some of the aforementioned features of the CGM app 410 are discussed below in further detail.

Backfill data: The CGM app 410 can receive older glucose values from the transmitter following periods of missed communication and will fill in data gaps on the trend graph (e.g., EGV data backfill). In some implementations, for example, during each data transfer, current glucose information has priority and is transferred before older information. Various implementations can allow for backfill CGM data to be acquired from the CGM device 420 over the entire record of CGM data on the CGM device 420 or for a predetermined duration from the current time. For example, the CGM app 410 can acquire the backfill CGM data over a 24 hour period, and display up to three hours of backfill CGM data when available.

Alert Profiles: The CGM app 410 allows a user to configure customizable CGM alerts (e.g., high glucose, low glucose, urgent low glucose, rise rate, fall rate and signal loss alert) to have different settings for two customizable time periods referred to as profiles (e.g., different settings for day and night, or work and play, or other user-determined lifestyle profiles). The CGM app 410 provides a set-up menu for these user-customizable alert profiles that makes it simple for a user, e.g., to reduce the risk of unintended alert profiles that might cause a user to not receive an appropriate alert), while also reducing the computational load on the smartphone device due to an otherwise burdensome process to setup the alert profiles.

Figure 5:
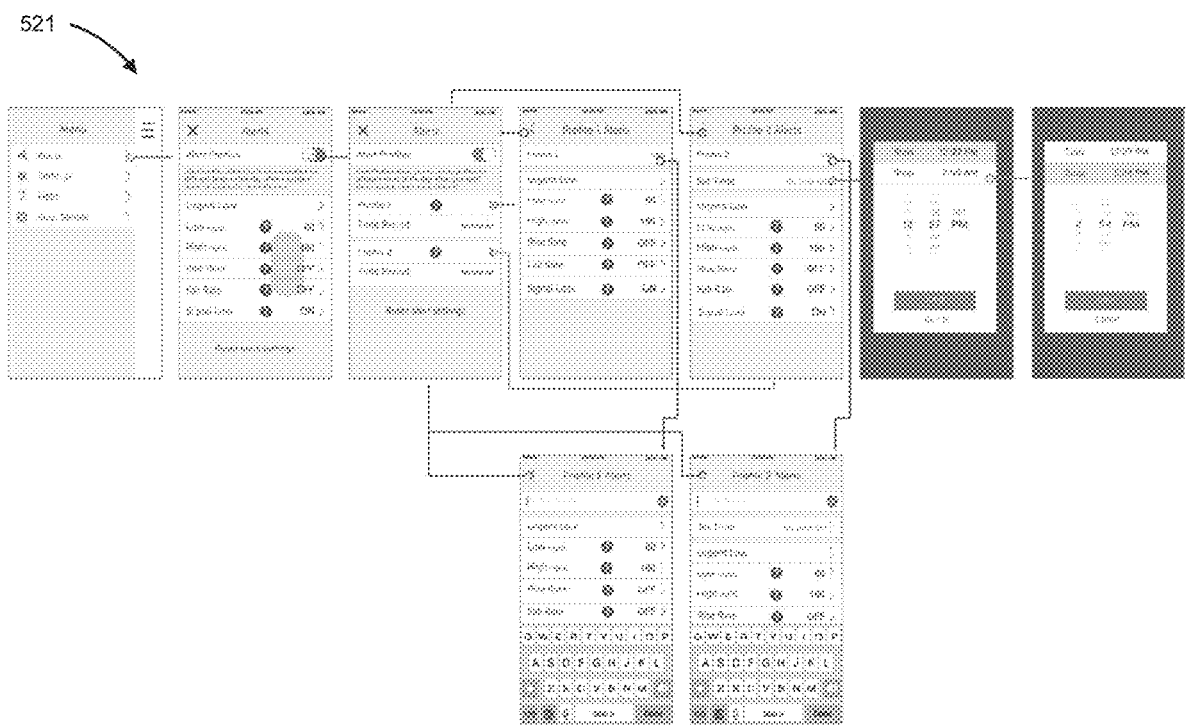
FIG. 5 is a diagram of a sequence of user interface displays of an example method to set up an alert profile for a CGM app in accordance with some implementations of the disclosed technology.

FIG. 5 is a diagram of a sequence of user interface displays 521 of an example method to set up an alert profile for a CGM app 410 in accordance with some implementations of the disclosed technology. In some embodiments of the CGM app 410, an alert profile set-up method includes a process to prompt a user to turn on or off the alert profiles feature. When turned on, the alert profile set-up method includes a process to prompt a user to name the first profile (e.g., default name "Profile 1") and the second profile (e.g., default name "Profile 2"). Upon selection of one of the two profiles, the set-up method displays a menu the name of the respective profile (editable) and a listing of alerts to set to the user-desired settings for that profile. In some implementations, for example, the listing of glucose alerts includes a high glucose alert, a low glucose alert, an urgent low glucose alert, a rise rate alert, a fall rate alert, and/or a signal loss alert, each with a default setting. For example, in some implementations, the default setting may not be changed or may be changed within a limited range based on a standard (e.g., medical standard, regulatory standard, etc.). Upon selection of one of the two profiles (e.g., the second profile in some implementations), the alert profile set-up method includes a process to allow the user to set the start and stop times of that respective profile. Upon setting the start/stop times for the one profile, the alert profile set-up method can include a process to automatically set the other profile to the time period outside the set profile time range. For example, if the user selects a start/stop time for the second profile (e.g., work profile) as 9 am to 5 pm, then the alert profile set-up method can automatically set the first profile (e.g., non-work profile) as 12:00:00 am to 8:59:59 am and 5:00:01 pm to 11:59:59 pm for each calendar day.

Escalating Mute Switch Override: For patient users' mobile computing devices that include appropriate vibration hardware to create a vibrate action (such as smartphones), the CGM app 410 is configured to override the mute switch set by the patient user on their smartphone, such as phone calls, texts, notifications, or other alerts, to reliably alert the patient user of his glucose condition in a manner that respects the user's desire to be uninterrupted, and therefore reduce alert fatigue. As a mobile medical device app, it is necessary that a patient user receives the alarms pertaining to their medical condition (e.g., glucose levels and trend) to promptly and properly react to their condition. However, patient users must manage their medical condition with the numerous interruptions of life, which often occur on the same device as the mobile medical app, i.e., the smartphone, tablet and/or smart wearable device. The CGM app 410 provides an intelligent alert escalation process to deliver glucose-related alerts when user's device is set to mute, low volume, and 'do not disturb' mode. For example, the intelligent alert escalation process is implemented automatically by the CGM app 410, so that setup by the user is not required.

In implementations, the escalating mute override feature can override a user-selected mute button or do not disturb mode for all CGM alarms in an escalating manner as follows. For example, when a high alert is triggered, the CGM app 410 generates an alarm to cause a vibrate action produced by the smartphone. If the user does not acknowledge the alert in a predetermined time (e.g., 5 minutes), then the CGM app 410 generates a second alarm as a low-volume audio alarm produced by the smartphone. If the user does not acknowledge the high alert associated with the second alarm in a second predetermined time (e.g., another 5 minutes), then the CGM app 410 generates a third alarm as a high-volume audio alarm produced by the smartphone. The Escalating Mute Override procedure can differ for the various types of alerts, such as Low, High, Urgent Low, Rise Rate, and Fall Rate glucose alerts. For example, for an urgent low alert, the CGM app 410 would immediately generate an alert produced as a high-volume audio alarm by the smartphone without escalation, whereas a high alert may constitute a first type of escalation and a low alert would be a second type of escalation.

Similarly, for example, the following alerts can be treated as escalating mute override alerts: Failed Sensor, Low Tx Battery, Sensor Expiration 0 min, Tx Error, Forced Sensor Shutoff, Tx EOL Replace, Disk Space Critical, Unrecoverable SQL Error alerts.

When a non-escalatable alert occurs, the CGM app 410 sends a local notification with the selected alert sound (without overriding the mute or do not disturb (DND) selection by the user). Yet, when an escalatable alert occurs, the CGM app 410 performs the mute override alert escalation sequence.

In some implementations, the escalation sequence includes: (i) the smartphone sending, based on instruction from the CGM app 410, a local notification with the selected alert sound (without mute override) and vibrating concurrently (if supported by the smartphone); (ii) playing, based on instruction from the CGM app 410, the alert sound (e.g., override mute/DND) at a medium volume and vibrating concurrently (if supported by the smartphone); and (iii) playing, based on instruction from the CGM app 410, the alert sound (override mute/DND) at a maximum volume and vibrating concurrently (if supported by the smartphone). For example, the CGM app 410 can implement the next escalation step if the user does not acknowledge the previous alarm within a predetermined time, e.g., 5 minutes between escalation steps for some or all escalatable alerts. In some implementations, when the alarm sound is finished for the escalatable alert, the CGM app 410 shall restore the device's volume back to its level before the alert. In some implementations, for example, when alerts are played at a volume greater than zero without headphones, the CGM app 410 can use 50% or the current system volume level or whichever is higher. Also, for example, when alerts are played at a volume greater than zero with headphones, the CGM app 410 can use 25% or the current system volume level or whichever is higher. In some implementations, for example, when alerts are played at Maximum volume without headphones, the CGM app 410 can use 100% volume level. Also, for example, when alerts are played at Maximum volume with headphones, the CGM app 410 can use 50% or the current system volume level, whichever is higher. The escalatable alerts that appear on the smartphone can be presented on the lock screen and include an acknowledge button (e.g., "OK" button). For example, when the acknowledge "OK" button is selected by the user, the CGM app 410 will stop the alert sound escalation and mark the alert as having been seen (e.g., the same or similar as acknowledging the alert in the CGM app's alert screen).

Figure 6A:
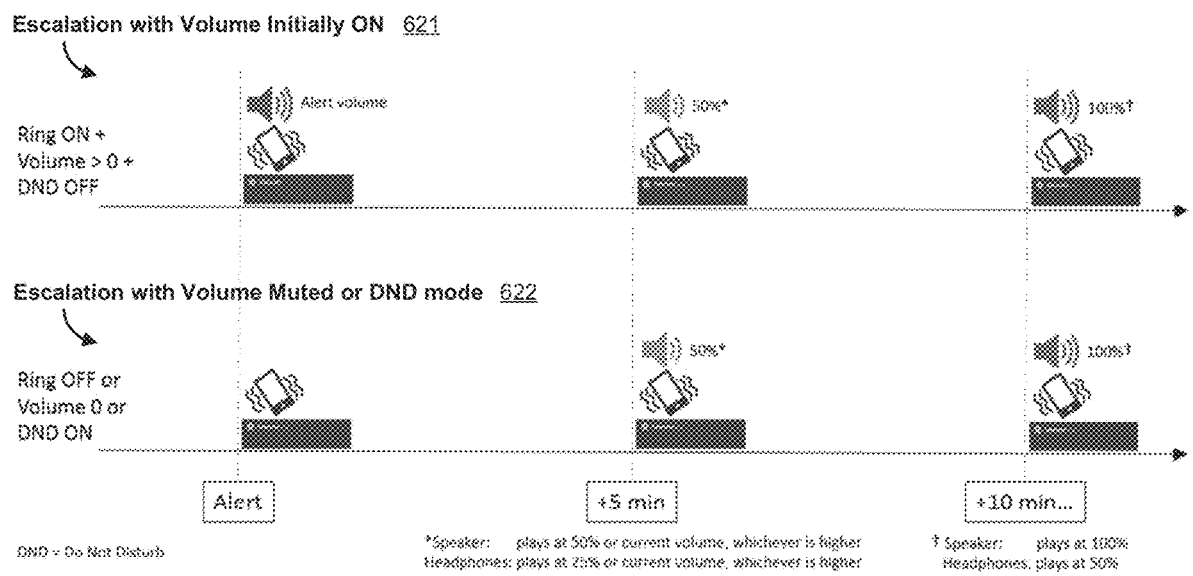
FIGS. 6A and 6B are diagrams of an example alert escalation sequence in accordance with some implementations of the disclosed technology implemented on a smartphone and smartwatch, respectively, that overrides patient user settings of mute, no volume or do not disturb, e.g., within modes corresponding to these settings, to ensure the patient user receives glucose alerts.

FIG. 6A is a diagram of an example alert escalation sequence in accordance with some implementations of the disclosed technology implemented on a smartphone operating the CGM app 410 that overrides a patient user setting of mute, no volume or do not disturb (DND) mode to ensure the patient user receives glucose or CGM device related alerts. As shown in the diagram, when an alert is triggered, the CGM app 410 causes the first instance of the alert to be presented with respect to the volume level, mute or DND preference the user has set. For example, if the smartphone's ringer is on, volume greater than zero, and not in DND mode, as shown in the sequence 621 of FIG. 6A, then the first instance of the alert will be presented at the sound level the user has set on his/her smartphone. If the smartphone's ringer is off, volume at zero, and/or in DND mode, as shown in the sequence 622 of FIG. 6A, then the first instance of the alert will be presented as a vibrational alarm that respects the user's preference. In implementations, the CGM app 410 can cause a visual alert notification to be presented on the display screen of the smartphone concurrently with the first alarm. If the first instance of the alert is not acknowledged, then a second instance of the alert will be presented after a predetermined time. In the example shown in the diagram, the CGM app 410 will cause the second instance of the alert to be presented by the smartphone after 5 minutes. In the second instance, the alert will be presented on the smartphone device as an auditory alarm at a predetermined volume level, e.g., X % of the device's maximum volume if muted, in DND mode, or set to a lower volume (less than X %), or if the volume is set greater than the predetermined volume level, then whichever is the higher. If the second instance of the alert is not acknowledged, then a third instance of the alert will be presented after a predetermined time. In the example shown in the diagram, the CGM app 410 will cause the third instance of the alert to be presented by the smartphone after 10 minutes (i.e., 5 minutes after the second instance of the alert). In the third instance, the alert will be presented on the smartphone device as an auditory alarm at another predetermined volume level, e.g., Y % of the device's maximum volume if muted, in DND mode, or set to a lower volume (less than Y %), or if the volume is set greater than the predetermined volume level, then whichever is the higher. In the example shown in the diagram, the CGM app 410 will cause the third instance of the alert to be presented by the smartphone at maximum (100%) of the device's volume without headphones, and 50% with headphones. In this example, the second and third instances of the alert are also presented as a vibrational alarm in addition to the auditory alarm, e.g., to help ensure the patient user receives the alert. If the third instance of the alert is not acknowledged, then the third instance of the alert can be presented again, e.g., periodically after a predetermined time such as every minute, or continuously until the alert is acknowledged.

Figure 6B:
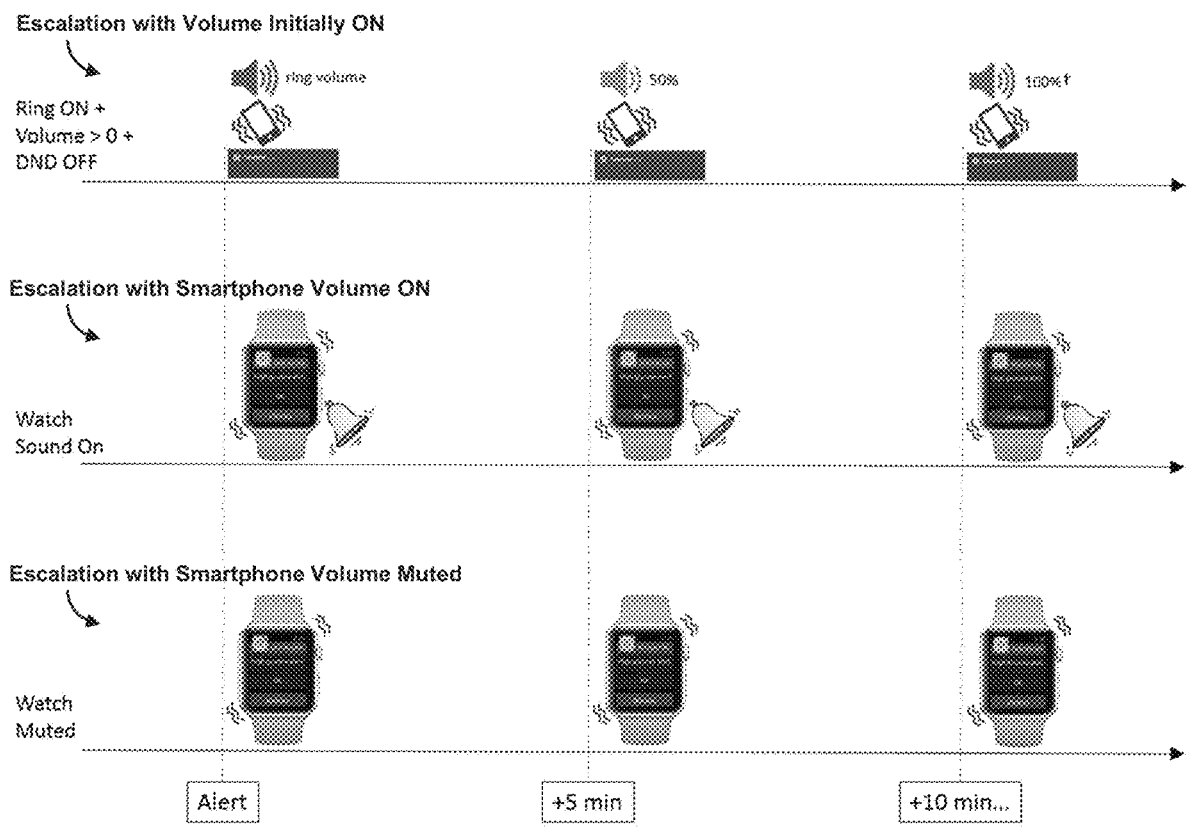

FIG. 6B is a diagram of an example alert escalation sequence in accordance with some implementations of the disclosed technology implemented on a smartwatch that overrides a patient user setting of mute, no volume or do not disturb mode to ensure the patient user receives glucose alerts. In implementations when the patient user's mobile computing device is a smartwatch, for example, when an alert occurs and on each escalation, the CGM smartwatch app can be configured to cause the smartwatch device to play a haptic and beep sound (unless the Watch is muted) except when the smartwatch is set in 'do not disturb' mode. This can be applied even when the "Vibrate Only" sound is selected. The alert notification that appears on the smartwatch can include an acknowledge "OK" button.

Vibrate Only alert option: For patient users' mobile computing devices that include appropriate vibration hardware to create a vibrate action (such as smartphones), the CGM app allows a user to select a Vibrate Only option for each customizable CGM alert, except for the Urgent Low alarm which must select a sound. Currently, the user can select a sound from a predefined list of sounds for each customizable alert, but not a vibrate only feature. Operation of the Vibrate Only feature of the CGM app can include the following. For example, the CGM app provide a "Vibrate Only" option in the sound menu (of the operating system's settings on the mobile computing device) for the Low, High, Rise Rate, and Fall Rate glucose alerts. The Vibrate Only feature is not available for the Urgent Low Alarm. The "Vibrate Only" option can be presented at the beginning of the list of sounds for the applicable alerts. When the "Vibrate Only" sound option is selected for an alert, the CGM app will cause vibration of the mobile computing device (e.g., smartphone) without playing any sounds and without volume escalation for the selected type of alert.

Notification Acknowledgement on Smartphone Lock Screen and Smartwatch—to minimize accidental alert acknowledgment while reducing alert fatigue: Currently, users can receive alerts on their smartphone and smartwatch lock screen. The notifications may include a default response button of "OK", so if the user selects "OK", their expectation is that they have seen and acknowledged the alert. However, the current alert system on the app does not meet the user expectation as it continues to alert the user, causing alert fatigue. This is particular the case for non-urgent or non-emergency type alerts, like high glucose alerts that are within a range about the high threshold.

The CGM app 410 has multiple levels of safety addressing acknowledgement of alerts to avoid an unintentional acknowledgment while minimizing alert fatigue. For example, a hypoglycemia event can cause a low alert first that can be acknowledged on the smartphone lock screen, and then another alert for an urgent low (e.g., 55 mg/dl alert) if the user continues to go lower than the hypoglycemic level that caused the first low alert. Also, if the user acknowledges both of these alerts (e.g., first low alert and urgent low alert), the CGM app 410 will continue to alert the patient user periodically (e.g., every 30 minutes) until their glucose level has risen above the urgent low threshold (e.g., 55 mg/dl). In some implementations, a lock screen and/or smartwatch notification acknowledgment can include providing a swiping button to prompt the user to swipe the screen to acknowledge the alert, and upon swiping the button, find a hidden button and tapping that button. For example, swiping-hidden-tapping button combo can prevent unintentional tapping of an acknowledgement button to mitigate false positive acknowledgements. This configuration addresses scenarios of accidental alert acknowledgement and alert fatigue, where accidental alert acknowledgment is a very low risk, and combined with the multiple redundant alert mitigations for hypoglycemia, such that alerting is safe without causing alert fatigue.

Calibration Entry Usability: The CGM app 410 provides a calibration entry flow from a Calibration Prompt Alert. In some implementations, the user can receive a prompt, e.g., labeled "Calibrate CGM", to directly take the user to the CGM app's calibration entry flow from a Calibration Prompt Alert displayed by the user's mobile computing device. The disclosed calibration entry flow can reduce the number of steps for calibration. For example, the calibration entry flow can be configured to require the user to enter a valid calibration value, select OK and then select OK again to confirm the value. In this manner, the calibration entry flow provides something more than a simple tap to prevent an unintentional calibration entry to occur.

Smartwatch Complications: Complications are features in some smartwatches (e.g., such as Apple Watch®) that provide information about a particular item of interest to a user, e.g., such as the calendar date, weather, or glucose value, in addition to the time. In some examples, complications can be represented as small elements that appear on the smartwatch's face to provide quick access to frequently used data. In the Apple Watch, a complication is a feature that allows a user to view data from multiple applications on their main watch face. The CGM app platform can provide a complication to the CGM app smartwatch version that can include the user's current glucose level and trend arrow immediately visible on the smartwatch face. However, some smartwatches may not allow for complications to update in real time frequently enough for the data to be displayed, and therefore not inform the user of pertinent information in a timely manner. In such situations, for example, the CGM smartwatch app can include a safety feature to prevent older glucose data to be conveyed to the user. For example, if the smartwatch operating the CGM smartwatch app does not receive updated glucose information, the CGM smartwatch app can cause the complication to transition to a 'no data' display. In some instances, the updated glucose information should be received after a predetermined amount of time, e.g., such as 15 minutes. In this manner, the CGM smartwatch app can reliably inform the patient user of his/her accurate glucose data in real time, or otherwise indicate it does not have such data and refer the patient user to check the CGM app on one of the user's other mobile computing device (e.g., smartphone).

Figure 7:
FIG. 7 is a diagram of an example smartwatch user interface including a complication for a CGM smartwatch app in accordance with some implementations of the disclosed technology.

FIG. 7 is a diagram of an example smartwatch user interface including a complication for a CGM smartwatch app in accordance with some implementations of the disclosed technology. The diagram depicts a main screen of the smartwatch showing the time and app complications, e.g., including the example CGM smartwatch app complication (e.g., showing a glucose value and trend), a calendar app complication (e.g., showing a date and day of the week), and other complications.

Data Import (exercise, meal, bolus, etc.): The CGM app 410 is able to import data, e.g., health data related to glucose management such as exercise data and meal (e.g., carbohydrate) data, from other apps that are not target apps included as part of the shared app group. In some implementations, exercise data captured by the patient user's smartphone, smartwatch or other connected fitness device can be exported from a health app (e.g., Apple Healthkit app) and imported to the CGM app 410. The CGM app 410 can process the imported data to log as event data. In some implementations, such imported data includes metadata or associated data that identifies the parameters about the data, such as the type of data, time of the event associated with the data, and specific data associated with the event, e.g., such as calories consumed or burned, type of food eaten or type of exercise performed, etc. The CGM app 410 can present the event data on the user interface. For example, the user is able to view the event data as icons presented on the landscape trend screen, but in a manner that will not affect the glucose display or alerts. The CGM app 410 can also provide the event data to the target apps using various embodiments of the inter-app communications architecture of the present technology. In some implementations, the data can also be manually entered in the CGM app 410 using an event entry tab. For example, the CGM app 410 can enable the user to view meal and/or exercise info on the same screen as historical glucose readings, e.g., which can add further benefits to the user by providing more contextual data that will enable users to associate meals or activity with poor or healthy glucose responses to glucose trends.

IOB—Display of Manually Entered Active Bolus Insulin Insulin stacking is a known issue in diabetes management, in which a diabetic may dose an additional dose or doses after an earlier dose that has not fully acted, which can lead to hypoglycemia. In some implementations of the CGM app 410, Active Bolus Insulin, also known as insulin on board (JOB), will be displayed on the CGM trend screen after the user manually enters a bolus insulin dose into the CGM App 410. Entry of bolus insulin dose can be performed similar to how users enter other event information into the CGM app 410. Displaying active insulin can provide a clear reminder to users that they have recently injected bolus insulin, which will mitigate insulin stacking from forgetting when the last dose was taken. For example, in some implementations, the active insulin is shown as a declining number of units, which will start at the dose time and finish at the insulin action time. No insulin units will remain at the insulin action time, which will default to 4 hours and can be user specified. The CGM app 410 can include IOB algorithms to determine the amount of insulin left based on curvilinear active insulin curves, which are best approximates of the pharmacokinetic actions of insulin. In one example, the curvilinear calculations are derived from measured insulin time-action profiles of different insulins studied by Lutz Heinemann in publications: Lutz Heinemann, "*Time-Action Profiles of Insulin Preparations*". Copyright© 2004, Publishers, Verlag Kirchheim+Co. GmbH, Kaiserstrasse 41, 55116 Mainz, Germany, and Heinemann et al., "*Variability of the Metabolic Effect of Soluble Insulin and the Rapid-Acting Insulin Analog Insulin Aspart*", Diabetes Care, Vol. 21 No. 11, pp 1910-1914, 1998.

Figure 8:
FIG. 8 is a diagram of an example user interface of an example CGM app in accordance with some implementations of the disclosed technology displaying insulin on board (JOB) data.

FIG. 8 is a diagram of an example user interface of an example CGM app 410 in accordance with some implementations of the disclosed technology displaying insulin on board data. The diagram depicts an example of a main screen of the CGM app 410 showing the glucose information (e.g., glucose value and trend), a trend graph of the glucose level (e.g., showing 3 hours of glucose levels), one or more icons proximate the trend graph depicting event data (e.g., such as an insulin bolus) with respect to time the event occurred on the trend graph, and IOB information, e.g., positioned proximate the glucose information and prominently at the top of the main screen of the CGM app 410 for fast, immediate viewing.

Historical Display of Manually Entered Long Acting and Bolus Insulin Injections: The CGM app 410 includes an enhanced display of the historical glucose and glucose-related data (e.g., insulin data) going back a predetermined amount of time (e.g., 24 hr and/or beyond) to more clearly show bolus and long acting insulin injected and logged by the user. For example, the historical display feature of the CGM app 410 can provide a historical glucose view where the user can look back over the last 24 hours of their glucose and manually entered events, including insulin.

Figure 9:
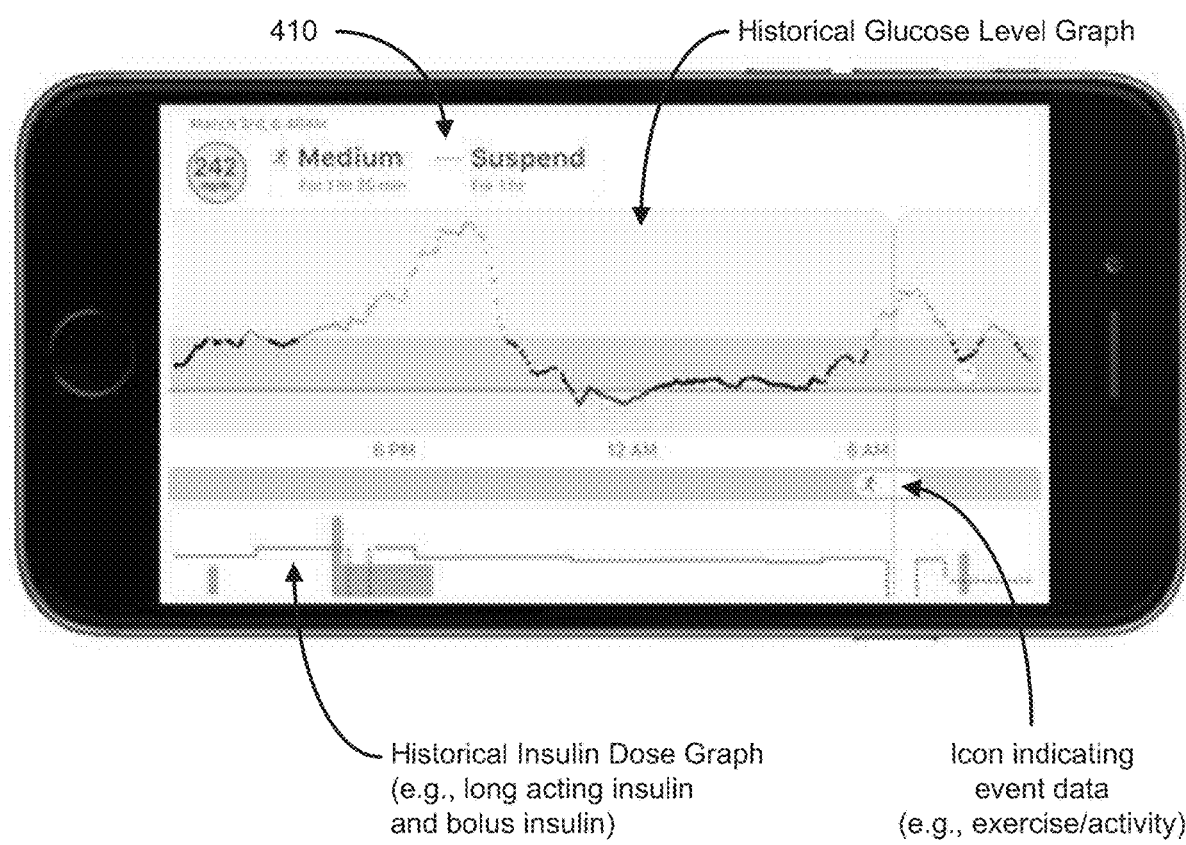
FIG. 9 is a diagram of an example user interface of an example CGM app in accordance with some implementations of the disclosed technology displaying historical glucose and insulin data.

FIG. 9 is a diagram of an example user interface of an example CGM app 410 in accordance with some implementations of the disclosed technology displaying historical glucose and insulin data. In some implementations, for example, the insulin data or other glucose-related data displayed on the historical can be provided to the CGM app 410 using various embodiments of the inter-app communications architecture of the present technology.

Figure 10A:
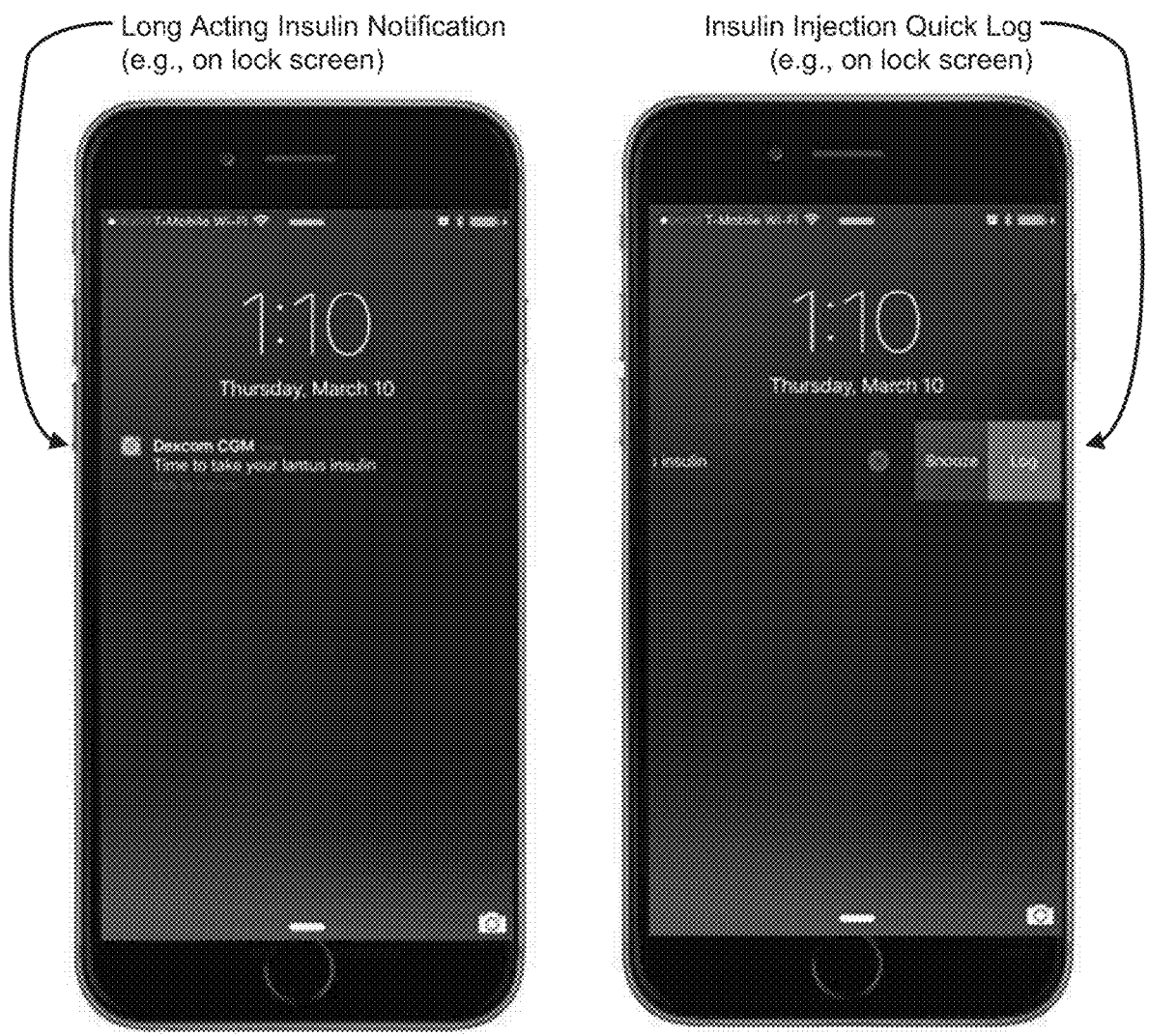
FIGS. 10A and 10B are diagrams of example user interfaces depicting a long acting insulin notification and quick logging feature for an example CGM app in accordance with some implementations of the disclosed technology on a smartphone device and a smartwatch device, respectively.
Figure 10B:

Long Acting Insulin Reminder: In some implementations, the CGM app 410 includes an optional feature to allow users to set a reminder notification for their long acting insulin. For example, the CGM app 410 can provide the long acting insulin notifications through a notification service associated with the operating system (e.g., such as an iOS notification), and to acknowledge the notification, the CGM app 410 can provide a quick log feature for the user to log that they have taken the injection. FIG. 10A is a diagram of example user interfaces depicting a long acting insulin notification and quick logging feature for an example CGM app 410 in accordance with some implementations of the disclosed technology. As shown in the diagram of FIG. 10A, a long acting insulin reminder is received on a lock screen of the user's mobile computing device (e.g., smartphone), in which the user acknowledges the notification and is prompted (by the CGM app) to log their insulin injection or delay the logging feature (e.g., snooze). For example, the long acting insulin notification can be displayed on the lock screen such that, to acknowledge the notification and receive the quick log prompt, the user swipes the notification, and upon swiping the button the quick log feature is presented. For example, this can prevent unintentional tapping of an acknowledgement and/or unintentional logging of an insulin injection to mitigate false positives. FIG. 10B is a diagram of an example user interface depicting a long acting insulin notification and quick logging feature for an example CGM smartwatch app in accordance with some implementations of the disclosed technology.

Launch of Bolus Calculator in a Target App: In some implementations, for example, the CGM app 410 can present the bolus calculator from another app linked to the CGM app 410 through embodiments of the inter-app communication architecture of the present technology. For example, the CGM app 410 can use the URL linking architecture (e.g., as an API) to start the bolus calculator for the inter-app system to provide to a partner Insulin App. In addition or alternatively, the CGM app 410 can use that API to start the bolus calculator in another linked target app such as another glucose management app with a bolus calculator or similarly a bolus calculator app, in particular for MDI users. For example, a 'Bolus Calc' button could automatically appear in the user interface of the CGM app 410 if a separate glucose management or bolus calculator app is linked such that, upon selection of the button, the URL linking architecture, e.g., via the data structure 112, would automatically take the user to that app's bolus calculator screen.

Figure 11:
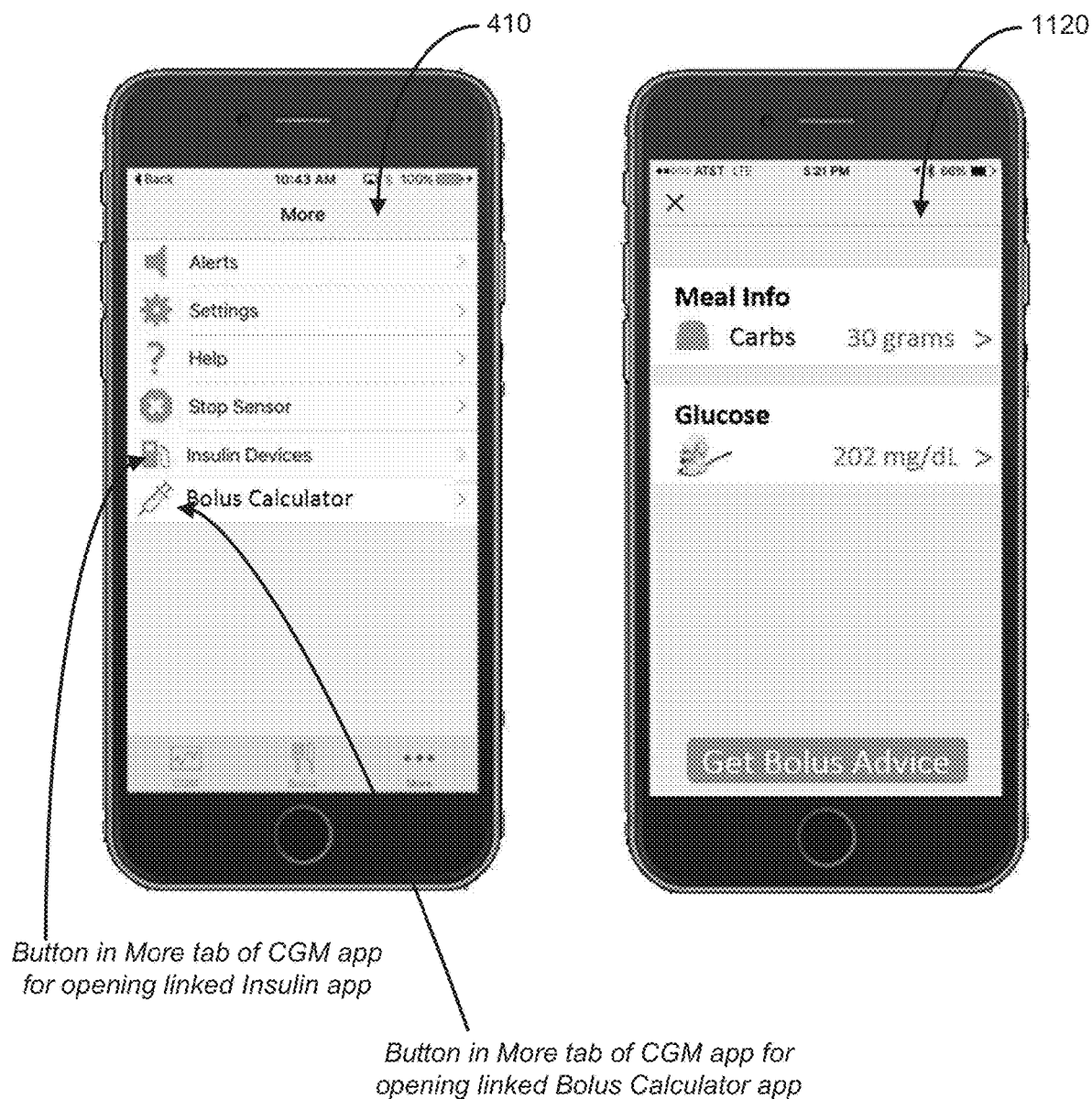
FIG. 11 is a diagram of display screens depicting an inter-app transition from an example CGM app to an example bolus calculator app in accordance with some implementations of the inter-app communications architecture of the present technology.

FIG. 11 is a diagram of display screens of the CGM app 410 and a bolus calculator app 1120 depicting an inter-app transition from the CGM app 410 to the bolus calculator app 1120 by selection of an icon (e.g., bolus calculator button in CGM app 410) to initiate the transition in accordance with some implementations of the inter-app communications 100 architecture of the present technology. In some implementations, the CGM app 410 can distribute CGM data to the bolus calculator app 1120 that the bolus calculator app 1120 may employ in determining a bolus. In the example shown in FIG. 11, the bolus calculator app 1120 includes a feature to enter or import data relevant to bolus calculation, e.g., such as meal data. The data generated by the bolus calculator app 1120 can in turn, for example, distribute the data (e.g., calculated insulin bolus data) to the CGM app 410 through the inter-app communications architecture 100, e.g., ensuring secure and immediate data transfer.

Authentication Code for Real Time CGM data: In some implementations, the CGM app 410 can be configured to require an authentication code be transferred from the CGM app 410 to the partner's Insulin app in order for a 'smart transmitter' of the CGM sensor to provide real time CGM data to the Insulin app. In such implementations, for example, if the CGM app 410 is not running, the partner's Insulin app cannot get real time CGM data from the pump that is connected to the smart transmitter. The exemplary authentication scheme can apply to an Insulin partner's closed loop systems that utilize a smart phone as the primary controller for their system.

Further Example Implementations

Android Operating System Environment

In some implementations of the systems and methods in accordance with the present technology, the inter-app communications architecture 100 can be implemented in the Android operating system environment. In such implementations in the Android operating system environment, the user interface of the source app 101 and the one or more target apps 102 can be configured to limit selection by the user for sharing data to the approved app or apps. For example, once the link is established, the source app 101 is available to share and receive data with the one or more approved and linked target apps 102, and the inter-app communications architecture 100 provides the ability to terminate the link and/or establish a new link with a different application that is available (e.g., approved).

In some implementations, e.g., in the Android operating system, enabling a third party application to work with the source app 101 may occur at runtime from the target app 102 via an Intent or via the source app 101 via a chooser of currently installed whitelisted (e.g., approved) software applications. For example, the UID and package name of the linked application process is stored locally to ensure that only the target application that the user intends will receive data. The option to link may be initiated via either the target app 102 or the source app 101 as shown in FIGS. 12A and 12B.

Figure 12A:
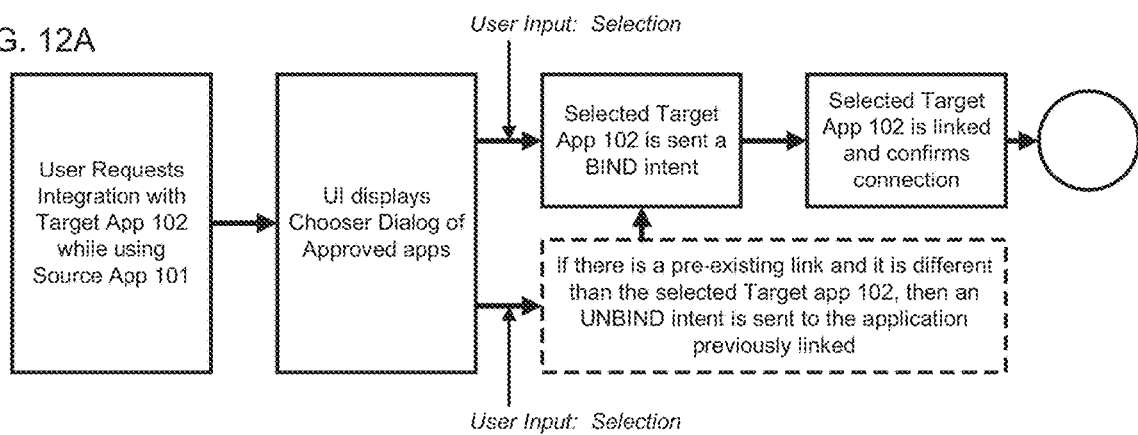
FIGS. 12A and 12B are diagrams of example methods to establish an inter-app communication link between a source app and a target app when a user is using the source app or the target app in accordance with some implementations of the inter-app communications architecture of the present technology.

FIG. 12A illustrates an example method to establish an inter-app communication link between the source app 101 and the target app 102 when a user is using the source app 101. In the example method, the user interface (UI) of the source app 101 displays a Chooser Dialog of the approved target apps. The user provides an input selection of a target app among the listed approved target apps. The inter-app communication architecture 101 facilitates the source app 101 to send the target app 102 a BIND intent. The selected target app 102 is linked, and confirms the connection. In some implementations of the inter-app communication architecture where only a single inter-app communication link may be established with the source app, and if there is a pre-existing link and if the user-selected target app is different than the previously linked target app, then an UNBIND intent is sent to the previously linked target app.

Figure 12B:
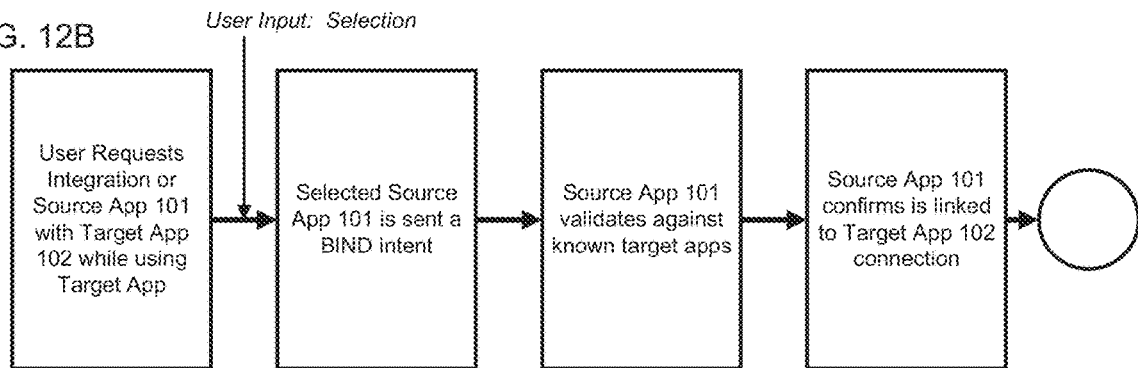

FIG. 12B illustrates an example method to establish an inter-app communication link between the source app 101 and the target app 102 when a user is using the target app 102. In the example method, the user provides an input selection of the source app 101, e.g., which can be presented via a tab or other display of the target app 102's UI. The inter-app communication architecture 101 facilitates the target app 102 to send a BIND intent to the source app 101. The source app 101 validates the target app 102 against a whitelist of approved target apps (e.g., analogous to the scheme list 115). The source app 101 is then linked, and confirms the connection.

In some implementations, the inter-app communication architecture can allow two applications to become unlinked via the UNBIND message. This may be sent either when the user selects to link a separate different target application, or if the user explicitly indicates that the two applications should no longer be associated. UNBIND may also be sent if the bound application is removed from the whitelist (e.g., due to changes in agreements between the source app entity and the target app entity). For example, UNBIND should not be sent as part of an upgrade process unless the newer version no longer supports the link. In addition, the source app 101 can be configured to listen for system INSTALL Intents for newly installed whitelisted applications and prompt the user to link the applications if there is no existing link to any application (e.g., do not overwrite an existing link). Conversely, for example, the source app 101 can be configured to listen for UNINSTALL system Intents and disconnect the link if an existing linked application is removed.

In some implementations in the Android operating system, the inter-app communication architecture 100 stores data in Android's internal SQLite database within the applications internal storage area. In such implementations, this can ensure that the data will be encrypted and not available to external sources. For example, security for the physical database can match the existing CgmDatabaseComponent for encryption and security practices.

For example, access to the data access layer from the source app 101 (e.g., such as the CGM app) is restricted via a signature level permission. The Android OS will then dis-allow access from applications that were not signed by a certificate from the CGM app. For example, the source app entity can make arrangements with third parties to allow access to read or write a subset of data to the database. Via the whitelist, e.g., which includes package name, signature, supported version numbers and permitted access criteria, the source application can validate all requests. The whitelist shall be updated periodically or nonperiodically and offer the option to force an update, e.g., via the UI.

In some implementations in the Android operating system environment, the calling application can be determined in response to StartActivityForResult( ), and ContentProvider and Service calls. In some examples, the method for identifying the caller varies based on the type of request, as follows:

1) StartActivityForResult( ) contains getCallingPackage( )

2) ContentProviders and Services return the calling process access via Binder.getCallingUid( )

The target process then uses the PackageManager, accessed via the context, to acquire the signature of the calling process. If the signature matches that of the previously linked application, the request is allowed to proceed. If not and it is a whitelisted application, the option to link may be provided. Otherwise, the request should be rejected possibly notifying the user of an unrecognized application request.

In some implementations, from time to time, the whitelist of target applications may need to be updated. This may be triggered by external event (e.g., a new contractual obligation), on a regular timer, by a system based event, and/or by request of the user. In such cases a REST request for the latest whitelist is made using the existing framework for making a secure internet request. An example of the format of request and response is shown as follows. The response is securely stored on the device until it either times out or is replaced by a new response.

```
Request:
GET https://{secure_dexcom_server}/whitelist&country={US, UK, etc}
Headers:
Accept-Language
Response (JSON):
{ "version" : "current_version",
whitelist : [
  { "id" : "Dexcom defined id"
  "displayName": "display name of application",
  "company" : "name of the company producing the application"
  "expires" : "when this whitelist entry expires"
  "androidPackage" : "package name as installed"
  "androidSignature" : "string version of public key"
  "androidUrl" : "install url for android"
  +iOS data - See iOS document for definition
  },
]
}
```

To support seamless integration, the following example Intent actions can be supported. The Intents containing INSULIN are intended to be sent to the example insulin delivery device application, and those containing a CGMentity are intended to be sent to a CGM device application. If neither CGM nor INSULIN is contained, either the insulin delivery device application or the CGM device application should be able to support the request. In implementations, the target activity can produce an error if the request cannot be authenticated. Example Intents include the following.

com.CGMentity.cgm.action.BIND—used to link an insulin device app to CGM app.

com.CGMentity.cgm.action.UNBIND—used to indicate that the application will no longer respond to messages sent by the target application.

com.CGMentity.cgm.action.INSULIN_HOME—request to open the target application's (e.g., insulin device app) home screen.

com.CGMentity.cgm.action.CGM_HOME—used to open the graph screen if currently logged in, or the login welcome page otherwise.

In some implementations in the Android operating system environment, the inter-app communication architecture 100 includes a database to make data access available through a content provider. In addition, to simplify integration with target apps, e.g., associated with medical devices or other health-related devices or applications, a thin wrapper can be provided to potential clients. At a minimum, a contract class describing URIs and columns available can be made available to partners. For example, some advantages provided by a content provider include: cursors work with standard UI widgets, ability to set update listeners, known documented interface style allows new developers to come up to speed relatively quickly, and/or simple to configure security for signature permissions on a per URI basis.

In some implementations in the Android operating system environment, the source app 101 includes an embodiment of the CGM app that includes an escalating mute switch override. For users' mobile computing devices that include appropriate vibration hardware to create a vibrate action (such as smartphones) and do not disturb (DND) modes on their operating systems, the CGM app can be configured to override the mute switch or DND modes set by the user on their smartphone, such as phone calls, texts, notifications, or other alerts, to reliably alert the patient user of his glucose condition in a manner that respects the user's desire to be uninterrupted, and therefore reduce alert fatigue. As a mobile medical device app, it is necessary that a patient user receives the alarms pertaining to their medical condition (e.g., glucose levels and trend) to promptly and properly react to their condition. However, patient users must manage their medical condition with the numerous interruptions of life, which often occur on the same device as the mobile medical app, i.e., the smartphone, tablet and/or smart wearable device. The CGM app provides an intelligent alert escalation process to deliver glucose-related alerts when user's device is set to mute, low volume, and 'do not disturb' mode. For example, the intelligent alert escalation process is implemented automatically by the CGM app, so that setup by the user is not required.

An operating system (e.g., such as Android, iOS, or others) may block applications from changing such user settings like DND mode, mute, or low volume (or others, like screen brightness, vibrate, or the like). While such restrictions set by the operating system on software apps operating in the operating system environment respect or adhere to user preferences, they can harm the functionality of a mobile medical software application to perform necessary steps. For example, in some versions of the Android operating system, the DND mode doesn't provide a mechanism to query and find out the DND state of the device. In such situations, there is a serious technical problem posed on the CGM app to guarantee that the glucose alerts can be delivered and/or presented to the patient user without any disruption.

Systems and methods in accordance with some embodiments of the present technology provide a technique to override user preferences such as DND mode, mute, and/or volume settings by generating and executing an override file that is able to be executed by the operating system regardless of the particular user preference setting to provide the desired functionality of the software app, and in some implementations, may not alter or affect the user preference setting yet still provide the desired functionality of the app, e.g., by employing an alternate audible pathway. In some implementations, the override file includes a sound file such as a music file that the operating system will allow to be played by the mobile computing device even when a particular user preference setting like DND mode or mute is set. In such implementations, the mobile medical app such as the example CGM app in accordance with the present technology can deliver and/or present glucose-related alerts (and/or insulin-related alerts in implementations of the inter-app communication architecture) on the patient user's mobile computing device regardless of the DND mode or mute setting.

Figure 13:
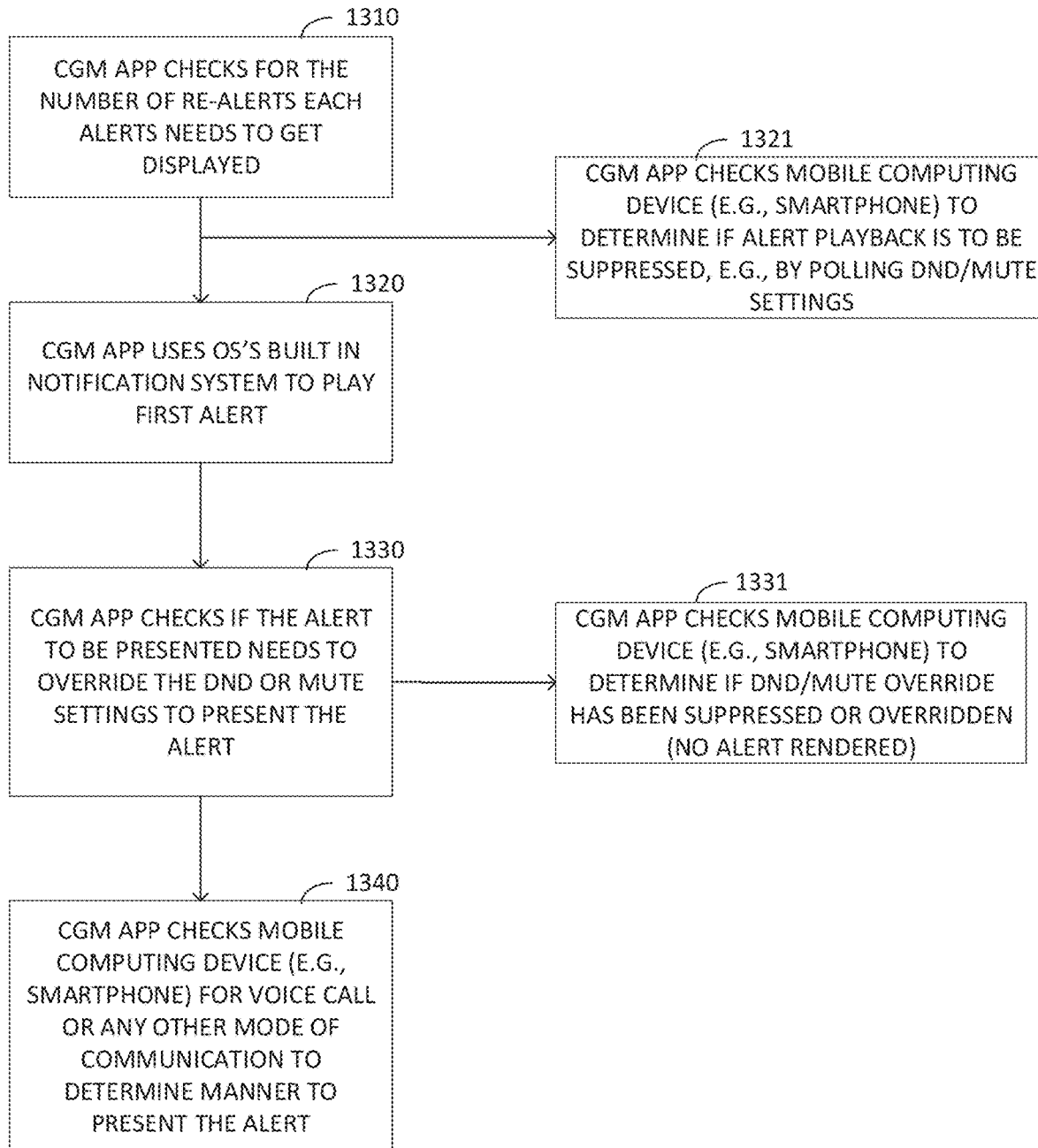
FIG. 13 is a diagram of an example method to determine if a mobile computing device is in a do not disturb mode, and/or to override such a do not disturb (DND) mode, to provide an alert, unless such a "DND/mute" override mode has been suppressed.

FIG. 13 illustrates an example method to determine if the mobile computing device is in DND mode, and if so, override DND mode to provide the alert, e.g., which can be implemented in the escalating alert sequence method previously described. For example, in implementations of the method, the CGM app can provide the alert to the user on the mobile computing device (e.g., smartphone) by playing a sound volume as the alert from the CGM app as a piece of music. In the Android operating system environment, instead of letting the system handle the notification sound, the CGM app can control the play of the sound itself as though the sound were a music file. For example, the intention of muting the smartphone is typically intended to disable notification sounds, not disable music. Also, in some implementations of the method, when the user is on a phone call on his/her smartphone device, the CGM app can play the audio through the "phone call" audio stream instead of the music phone stream, as the phone call audio stream suppresses the music audio stream.

In the Android operating system environment, for example, Music stream and Voice stream are not bound by the same audio limitations as the Notification stream which is used by in built Notification system (which doesn't override the user settings such as DND, Mute & volume settings). For example, Music stream and Voice stream are not managed and used by Android in built Notification system. Mobile device manages different audio streams, and the App can choose the stream to play the notification sound file.

As shown in FIG. 13, the method includes a process 1310 in which the CGM app checks for the number of Re-Alerts each alert needs to get displayed. At process 1320, the CGM app uses Android in built Notification system to play the First alert. This may or may not override the user volume settings on the mobile device. At process 1330, the CGM app checks if the alert that was supposed to be presented needs to override the DND or Mute settings to present the alert. For example, not all alerts requires DND or Mute override. At process 1340, the CGM app checks mobile computing device (e.g., smartphone) for Voice Call or any other mode of communication to determine the manner to present the alert. In some implementations, the processes of the method shown in FIG. 13 can be implemented in different orders than that shown in FIG. 13.

In some implementations of the process 1340, if in Voice call or any other mode of communication, the CGM app gets the current volume level of the Voice Stream and/or gets the current volume level of the Music Stream. For the alerts other than the First Alert, the CGM app checks if current volume level is lower than a predetermined volume threshold (e.g., referred to as Mute Override Volume) based on the alert count. In this example, the current volume level is determined by "x" % of max volume of a particular stream. This "x" is again determined based on the headphones On/Off on that device. If the current volume level is lower, than the CGM app increases the current volume level to the Mute Override Volume. If the current volume level is higher than Mute Override Volume, then no changes are made to the current volume level. Based on the state of mode of communication (e.g., Voice call) the device is in, the CGM app initiates the media player and sets the media player stream to, for example: STREAM_VOICE_CALL, or STREAM_MUSIC, and play the sound file through media player. The CGM app sets the stream (e.g., Music or Voice) volume to user set volume as soon as the sound is played or the alert is acknowledged by the user.

Table 2 shows an alert count sequence for volume level when head phones are on or when sound is played through the device's speakers.

TABLE 2

| Alert Count | Mute override Volume level when Head Phones are ON | Mute override Volume level when sound played through Speakers |
| --- | --- | --- |
| 0 | 0% of Max Volume | 0% of Max Volume |
| 1 | 25% of Max Volume | 50% of Max Volume |
| 2 | 50% of Max Volume | 100% of Max Volume |

Table 3 shows a device mode or setting override escalation and non-escalation sequence for providing alerts.

TABLE 3

| | 1$^{st}$ Alert | 2$^{nd}$ Alert | 3$^{rd}$ Alert |
| --- | --- | --- | --- |
| Escalatable | Normal Sound | Override Sound | Override Sound |
| | Override Vibrate | Override Vibrate | Override Vibrate |
| Non-Escalatable | Normal Sound | Normal Sound | Normal Sound |
| | Normal Vibrate | Normal Vibrate | Normal Vibrate |

In some implementations, users may be enabled to disable, override, or otherwise defeat the above-mentioned overrides, so as to provide greater control over their alerts and alarms. This step can be performed in several ways. For example, in one arrangement, the CGM app may check or poll the mobile computing device to determine if the user has indicated a desire to have alerts and alarms suppressed or overridden (collectively, "suppressed"), in other words, the user does not want to receive such. This is indicated by step 1321, where a first alert is determined to be appropriate, but a user has indicated a desire to have the same suppressed. Put another way, this implementation contemplates the case where no DND/mute override has occurred.

In another technique, some implementations as noted above are configured to override certain user settings, e.g., some configurations override DND/mute settings. In such cases, the override itself may be suppressed overridden as indicated by step 1331, where the DND/mute override has been overridden by the user settings. If so, no alert will be rendered.

Variations may occur in such situations where user settings prevail, and the user is not notified. For example, in some cases, to accomplish device safety goals, if alerts and/or alarms are allowed to be suppressed, or overridden by DND/mute settings, the configuration may be such that alerts may be suppressed but not alarms. In another configuration, either or both may be suppressed but only for a predetermined and limited duration of time, e.g., 1 hour, 2 hours, 3 hours, and so on. In yet another configuration, only certain types of alerts/alarms may be suppressed. For example, urgent overnight lows may be disallowed from being suppressed, and may thus always be provided to the user. In yet another configuration, a "vibrate" mode may be provided, where in this mode, if the device is muted, the alerts/alarms will only vibrate instead of making a sound (exceptions may also occur in this mode, e.g., for urgent lows, which may cause an audible alarm). Other variations, implementations, and configurations will also be understood given this teaching.

In any of the variations, an icon on the home screen may be employed to display whether a particular mode is active, e.g., if the vibrate mode is active. Such icons may also provide quick access to the settings screen(s), that allow users to turn such functions on and off, and also allow the user to assign certain time periods to certain respective profiles. For example, the user may have one profile active at night and another during the day.

EXAMPLES

The following examples are illustrative of several embodiments and implementations in accordance with the present technology. Other example embodiments and implementations of the present technology may be presented prior to the following fisted examples, or after the following listed examples.

In some embodiments in accordance with the present technology (Example 1), a method for initiating inter-application communication between software applications includes designating software apps to a shared app group for an operating system of a mobile computing device, the shared app group including a first software app and one or more preapproved software apps, the first software app stored on a computer-readable medium of the mobile computing device and comprising instructions executable by a processor of the mobile computing device; establishing an inter-app data communication architecture on the mobile computing device to link the first software app and a second software app included among the preapproved software apps, in which the inter-app data communication architecture includes a data structure including (i) a scheme field to identify a software app from a scheme list and (ii) a payload field that is encrypted and includes data and/or an identification where to access data in a shared file system of the shared app group; generating a public/private key pair for encryption and decryption of the payload field of the data structure by: providing a first public key for the first software app in a shared keychain of the shared app group, providing a first private key for the first software app in a first private keychain accessible to the first software app, providing a second public key for the second software app in the shared keychain, and providing a second private key for the second software app in a second private keychain accessible to the second software app; and generating a database key for encryption of a shared database in the shared file system by producing a database key in the first private keychain accessible to the first software app, and creating an encrypted database key by encrypting a copy of the database key with the second public key, in which the encrypted database key is stored in the shared keychain.

Example 2 includes the method of Example 1, in which the first software app includes a first version of the scheme list that includes the preapproved software apps, and the second software app includes a second version of the scheme list that includes at least the first software app.

Example 3 includes the method of Example 1, further including displaying on a display of the mobile computing device a user interface of the first software app including a list of at least some of the preapproved software apps including the second software app on the scheme list; receiving, at the first software app, a link instruction to establish the inter-app data communication architecture between the first software app and the second software app, in which the link instruction is based on a user selection of the second software app from the list; and creating a link between the first software app and the second software app based on the inter-app data communication architecture.

Example 4 includes the method of Example 3, in which the user interface of the first software app includes one or both of a name of the second software app or of a device associated with the second software app, an icon or graphic indicative of the second software app or of the device associated with the second software app.

Example 5 includes the method of Example 4, in which the user interface of the first software app includes status information indicative of the link between the first software app and the second software app.

Example 6 includes the method of Example 5, in which the user interface of the first software app includes an unlink button to allow the user to provide an unlink instruction to remove the inter-app data communication architecture between the first software app and the second software app, in which the unlink instruction is generated responsive to a user selection of the unlink button.

Example 7 includes the method of Example 5, in which the list of the at least some of the preapproved software apps includes software apps not installed on the mobile computing device; and the method further includes receiving, at the first software app, a get instruction to obtain an uninstalled software app; and generating a command to open an app page for the uninstalled software app on an app store application resident on the mobile computing device.

Example 8 includes the method of Example 1, in which the first software app is independent of the second software app.

Example 9 includes the method of Example 1, in which the established inter-app data communication architecture provides permission to the second software app to read and write to data stored in the shared database using the encrypted database key.

Example 10 includes the method of any of Examples 1-9, in which the mobile computing device includes a smartphone, a tablet, or a wearable electronics device including a smartwatch or a smartglasses.

Example 11 includes the method of any of Examples 1-10, in which the first software app is a continuous glucose monitoring (CGM) app associated with a CGM device, and the second software app is an insulin app associated with an insulin delivery device.

In some embodiments in accordance with the present technology (Example 12), a method provides for inter-application communication between software applications in a shared app group for an operating system of a mobile computing device, in which the software applications are stored on a computer-readable medium of the mobile computing device and each comprise their own instructions executable by a processor of the mobile computing device. The method includes operating a first software app in a foreground on the mobile computing device; generating a data structure to initiate a transition from the first software app to a second software app in the foreground, the generating including (i) populating a scheme field of the data structure with a scheme id associated with the second software app from a scheme list stored with the first software app, (ii) populating a payload field of the data structure with data and/or an identification where to access data in a shared file system accessible to the software applications in the shared app group, and (iii) encrypting at least the payload field of the data structure; providing the data structure to cause initiation of the second software app to the foreground; and providing at least the encrypted payload field of the data structure for the second software app.

Example 13 includes the method of Example 12, in which the encrypting the payload field of the data structure includes using a public/private key pair for encryption and decryption of the payload field.

Example 14 includes the method of Example 13, in which the public/private key pair includes a first public key for the first software app stored in a shared keychain of the shared app group, a first private key for the first software app in a first private keychain accessible to the first software app, a second public key for the second software app in the shared keychain, and a second private key for the second software app in a second private keychain accessible to the second software app.

Example 15 includes the method of Example 12, in which the data structure is provided to the operating system as a command to initiate the second software app to the foreground.

Example 16 includes the method of Example 15, further including, upon initiation of the second software app to the foreground, relegating the first software app to the background or closing the first software app.

Example 17 includes the method of Example 12, in which the providing the at least the encrypted payload field includes providing a copy of the data structure.

Example 18 includes the method of Example 12, in which the shared file system includes an encrypted shared database accessible to the first software app using a master database key in a first private keychain accessible to the first software app and accessible to the second software app using an asymmetric encrypted database key in a shared keychain of the shared app group.

Example 19 includes the method of Example 18, in which the asymmetric encrypted database key is created by encrypting a copy of the master database key using a second public key for the second software app in the shared keychain, and is decrypted using a second private key for the second software app in a second private keychain accessible to the second software app.

Example 20 includes the method of Example 12, further including displaying on a display of the mobile computing device a user interface of the first software app including an icon representing the second software app or data associated with the second software app; and receiving, at the first software app, a transition instruction to cause the providing the data structure to cause the initiation of the second software app and the providing at least encrypted payload field for the second software app, in which the transition instruction is based on a user selection of the icon on the user interface.

Example 21 includes the method of any of Examples 12-20, in which the mobile computing device includes a smartphone, a tablet, or a wearable electronics device including a smartwatch or a smartglasses.

Example 22 includes the method of any of Examples 12-21, in which the first software app is a continuous glucose monitoring (CGM) app associated with a CGM device, and the second software app is an insulin app associated with an insulin delivery device.

Example 23 includes the method of Example 22, in which the data included in the payload field includes data points associated with glucose values.

In some embodiments in accordance with the present technology (Example 24), a system for managing care of diabetes includes a continuous glucose monitoring (CGM) device operable to obtain glucose measurements and wirelessly transmit the glucose measurements to an external device; an insulin delivery device operable to inject a dose of insulin; and a mobile computing device, comprising a wireless receiver to receive the glucose measurements, a memory to store data including the received glucose measurements, a processor to process the data, a first software application pertaining to the CGM device and a second software application pertaining to the insulin delivery device. The first software application includes instructions stored in the memory which, when executed by the processor, generate a data structure to initiate a transition from the first software app to the second software app in the foreground, provide the data structure to cause initiation of the second software app to the foreground, and provide at least the encrypted payload field of the data structure for the second software app. The second software application includes instructions stored in the memory which, when executed by the processor, receive the at least encrypted payload field.

Example 25 includes the system of Example 24, in which instructions of the first software application to generate the data structure includes instructions to populate a scheme field of the data structure with a scheme id associated with the second software app from a scheme list stored with the first software app, populate a payload field of the data structure with data and/or an identification where to access data in a shared file system accessible to the software applications in in a shared app group for an operating system of the mobile computing device, and encrypt at least the payload field of the data structure.

Example 26 includes the system of Example 25, in which the payload field of the data structure is encrypted by a public/private key pair.

Example 27 includes the system of Example 26, in which the public/private key pair includes a first public key for the first software app stored in a shared keychain of the shared app group, a first private key for the first software app in a first private keychain accessible to the first software app, a second public key for the second software app in the shared keychain, and a second private key for the second software app in a second private keychain accessible to the second software app.

Example 28 includes the system of Example 25, in which the shared file system includes an encrypted shared database accessible to the first software app using a master database key in a first private keychain accessible to the first software app and accessible to the second software app using an asymmetric encrypted database key in a shared keychain of the shared app group.

Example 29 includes the system of Example 28, in which the asymmetric encrypted database key is an encrypted copy of the master database key encrypted using a second public key for the second software app in the shared keychain and decrypted using a second private key for the second software app in a second private keychain accessible to the second software app.

Example 30 includes the system of Example 24, in which, the second software application includes instructions stored in the memory which, when executed by the processor receive a copy of the data structure.

Example 31 includes the systems of any of Examples 24-30, in which the mobile computing device includes a smartphone, a tablet, or a wearable electronics device including a smartwatch or a smartglasses.

Example 32 includes the systems of any of Examples 24-31, in which one or both of the first and second software apps are mobile medical apps approved by a regulatory body of medical devices, and the first software app is a CGM app associated with the CGM device, and the second software app is an insulin app associated with the insulin delivery device.

In some embodiments in accordance with the present technology (Example 33), a computer-readable medium on a mobile computing device comprising instructions which, when executed by a processor of the mobile computing device, perform a method for transitioning and distributing data between software applications in a shared app group for an operating system of a mobile computing device, including generating a data structure to initiate a transition from a first software app operating in the foreground to a second software app to operate in the foreground, the generating including (i) populating a scheme field of the data structure with a scheme id associated with the second software app from a scheme list stored with the first software app, (ii) populating a payload field of the data structure with data and/or an identification where to access data in a shared file system accessible to the software applications in the shared app group, and (iii) encrypting at least the payload field of the data structure; providing the data structure to cause initiation of the second software app to the foreground; and providing at least the encrypted payload field of the data structure for the second software app.

In some embodiments in accordance with the present technology (Example 34), a computer-readable medium on a mobile computing device comprising an inter-application communication data structure to facilitate transitioning and distributing data between software applications in a shared app group for an operating system of the mobile computing device, including a scheme field of the data structure providing a scheme id associated with a target software app to transition to from a source software app, in which the scheme id is listed on a scheme list stored with the source software app; and a payload field of the data structure providing data and/or an identification where to access data in a shared file system accessible to the software applications in the shared app group, in which the payload field is encrypted.

Example 35 includes the computer-readable medium of Example 34, in which the payload field of the data structure is encrypted using a public/private key pair comprising a first public key for the source software app stored in a shared keychain of the shared app group, a first private key for the source software app in a first private keychain accessible to the source software app, a second public key for the target software app in the shared keychain, and a second private key for the target software app in a second private keychain accessible to the target software app.

Example 36 includes the computer-readable medium of Examples 34 or 35, in which the mobile computing device includes a smartphone, a tablet, or a wearable electronics device including a smartwatch or a smartglasses.

Example 37 includes the computer-readable medium of any of Examples 34-36, in which the source software app is a continuous glucose monitoring (CGM) app associated with a CGM device, and the target software app is an insulin app associated with an insulin delivery device.

In some embodiments in accordance with the present technology (Example 38), a method for facilitating inter-app communications between software applications, includes receiving, by a first software app on a mobile computing device, a first instruction to transition from the first software app to a second software app on the mobile computing device; generating a data structure to initiate the transition and provide a data payload to the second software app; and providing, by the first software app, the data structure to cause initiation of the second software app in a foreground mode of the mobile computing device.

Example 39 includes the method of Example 38, including generating, by the first software app, the first instruction based on a user selection of an identifier of the second software app presented on a display screen of the first software app.

Example 40 includes the method of Example 39, in which the identifier includes one or both of an icon and text associated with the second software app.

Example 41 includes the method of Example 38, in which the generating includes (i) populating a first field of the data structure with a scheme id associated with the second software app, (ii) populating a second field of the data structure with the data payload, and (iii) encrypting at least the second field of the data structure.

Example 42 includes the method of Example 41, in which the scheme id is listed on a predetermined scheme list stored with the first software app.

Example 43 includes the method of Examples 38 or 41, in which the data payload includes at least one of data or an identification where to access data in a shared file system accessible among at least the first and the second software apps.

Example 44 includes the method of Example 38, in which the encrypting the second field of the data structure includes using a public/private key pair for encryption and decryption of the payload data.

Example 45 includes the method of Example 44, in which the public/private key pair includes a first public key for the first software app stored in a shared keychain among at least the first and second software apps, a first private key for the first software app in a first private keychain accessible to the first software app, a second public key for the second software app in the shared keychain, and a second private key for the second software app in a second private keychain accessible to the second software app.

Example 46 includes the method of Example 38, in which the providing the data structure includes providing at least the encrypted payload field of the data structure for the second software app.

Example 47 includes the method of Example 38, in which the data structure is provided to an operating system of the mobile computing device as a command to initiate the second software app to the foreground.

Example 48 includes the method of any of Examples 38, 39, 41, 44, 46 or 47, further including providing, by the first software app, data to an encrypted shared database accessible with reading and writing data privileges to the first software app and the second software app based on one or more encryption keys.

Example 49 includes the method of Example 48, in which the encrypted shared database is in a shared file system able to be accessed among at least the first and the second software apps, and the data in the encrypted shared database is available to only software applications with the one or more encryption keys.

Example 50 includes the method of Example 48, in which at least one encryption key is based on a master database key stored in a first private keychain accessible to the first software app.

Example 51 includes the method of Example 48, in which at least one encryption key includes an asymmetric encrypted database key by encrypting a copy of the master database key using a second public key for the second software app in the shared keychain.

Example 52 includes the method of any of Examples 38-51, in which the mobile computing device includes a smartphone, a tablet, or a wearable electronics device including a smartwatch or a smartglasses.

Example 53 includes the method of any of Examples 38-52, in which the first software app is a continuous glucose monitoring (CGM) app associated with a CGM device, and the second software app is an insulin app associated with an insulin delivery device.

In some embodiments in accordance with the present technology (Example 54, as well as other Examples), a computer-readable medium on a computing device comprising an inter-application communication architecture to facilitate transitioning and distributing data between software applications.

In some embodiments in accordance with the present technology (Example 54), a method of establishing an inter-app communication link between a source app and a target app when a user is using the source app, includes receiving input from a user, the input received on a user interface of a source app, the input including a selection of a target app from among one or more target apps; transmitting a bind intent from the source app to the target app; and upon receipt of the bind intent, linking the target app to the source app.

Example 55 includes the method of Example 54, in which only one inter-app communication link is allowed between a source app and a target app, and further including transmitting an unbind intent to a prior linked target app.

Example 56 includes the Example of any of Examples 54-55, in which the source app is a continuous glucose monitoring application and the target app is a medicament delivery app, or in which the target app is a continuous glucose monitoring application and the source app is a medicament delivery app.

In some embodiments in accordance with the present technology (Example 57), a method of establishing an inter-app communication link between a target app and a source app when a user is using the target app, includes receiving input from a user, the input received on a user interface of a target app, the input including a selection of a source app; transmitting a bind intent from the target app to the source app; at the source app, validating the target app; and if the target app is validated, linking the source app to the target app.

Example 58 includes the method any of Examples 57, in which the validating includes determining if the target app is on a whitelist of approved target apps.

Example 59 includes the method any of Examples 57-58, in which the source app is a continuous glucose monitoring application and the target app is a medicament delivery app, or in which the target app is a continuous glucose monitoring application and the source app is a medicament delivery app.

In some embodiments in accordance with the present technology (Example 60), a method for providing an alert or alarm to a user using a mobile communications device, includes detecting or determining an alert or alarm state on the mobile communications device, the alert or alarm state pertaining to an instantiated app; determining if the mobile communications device is in a state inhibiting audible alerts or alarms; if the communications device is in a state inhibiting audible alerts or alarms, then determining if an alternate audible pathway exists on the mobile communications device; and if an alternate audible pathway exists, then rendering the alert or alarm using the alternate audible pathway.

Example 61. The method of Example 60, in which the alternate audible pathway includes a voice channel or a music or other sound playback channel.

In some embodiments in accordance with the present technology (Example 62), a method for providing an alert or alarm to a user using a mobile communications device, includes detecting or determining an alert or alarm state on the mobile communications device, the alert or alarm state pertaining to an instantiated app; determining if the mobile communications device is in a state inhibiting audible alerts or alarms; if the communications device is in a state inhibiting audible alerts or alarms, then creating an override file, the override file configured to be capable of being executed by the operating system regardless of the particular user preference setting to provide the desired functionality of the software app, such that the override file causes a rendering of the alert or alarm on the mobile communications device.

In some embodiments in accordance with the present technology (Example 63), a method for providing an alert or alarm to a user using a mobile communications device, includes detecting or determining an alert or alarm state on the mobile communications device, the alert or alarm state pertaining to an instantiated app; determining if the mobile communications device is in a state inhibiting audible alerts or alarms; and if the communications device is in a state inhibiting audible alerts or alarms, rendering the alert or alarm using a vibratory alert, such that the user is enabled to cause a vibration mode, and such that vibrations are employed to alert or alarm the user.

In some embodiments in accordance with the present technology (Example 64), a method of running multiple apps while minimizing the effects of errors on either, includes: running a CGM app on a mobile device; running a bolus calculator or a medicament delivery app on the mobile device; detecting that the CGM app, and the bolus calculator or medicament delivery app, are accessing a common memory location, the common memory location not associated with a shared database; upon the detecting, shutting down the CGM app, or the bolus calculator or medicament delivery app, or causing the CGM app, or the bolus calculator or medicament delivery app, to indicate an error.

In some embodiments in accordance with the present technology (Example 65), a method of running multiple apps while minimizing the effects of errors on either, includes: running a CGM app on a mobile device; running a bolus calculator or a medicament delivery app on the mobile device; detecting that the CGM app, and the bolus calculator or medicament delivery app, are experiencing crosstalk or sharing data; upon the detecting, shutting down the CGM app, or the bolus calculator or medicament delivery app, or causing the CGM app, or the bolus calculator or medicament delivery app, to indicate an error.

In some embodiments in accordance with the present technology (Example 66), a method of running multiple apps, includes running a CGM app on a mobile device; running a bolus calculator or a medicament delivery app on the mobile device; causing at least one visualization experience to be common across the mobile device for both of the CGM app, and the bolus calculator or medicament delivery app.

Example 67 includes the method of Example 66, in which the common visualization experience relates to display of CGM data.

In some embodiments in accordance with the present technology (Example 71), a method for providing an alert or alarm to a user using a mobile communications device includes detecting or determining an alert or alarm state on the mobile communications device, the alert or alarm state pertaining to an instantiated app; determining if the mobile communications device is in a state inhibiting audible alerts or alarms; if the communications device is in a state inhibiting audible alerts or alarms, then determining if an alternate audible pathway exists on the mobile communications device; and if an alternate audible pathway exists, then rendering the alert or alarm using the alternate audible pathway.

Example 72 includes the method of Example 71, wherein the alternate audible pathway includes a voice channel or a music or other sound playback channel.

Example 73 includes the method of any of Examples 71-72, further comprising, following the determining if an alternate audible pathway exists on the mobile communications device, determining if a user has indicated that the alternate audible pathway is not to be used, and if so, then suppressing the rendering of the alert or alarm using the alternate audible pathway.

In some embodiments in accordance with the present technology (Example 74), a method for providing an alert or alarm to a user using a mobile communications device includes detecting or determining an alert or alarm state on the mobile communications device, the alert or alarm state pertaining to an instantiated app; determining if the mobile communications device is in a state inhibiting audible alerts or alarms; if the communications device is in a state inhibiting audible alerts or alarms, then creating an override file, the override file configured to be capable of being executed by the operating system regardless of the particular user preference setting to provide the desired functionality of the software app, such that the override file causes a rendering of the alert or alarm on the mobile communications device.

Example 75 includes the method of Example 74, wherein the override file causes a vibratory alert, such that the user is enabled to cause a vibration mode, and such that vibrations are employed to alert or alarm the user.

Example 76 includes the method of any of Examples 74-75, further comprising, following the determining of an alert or alarm state on the mobile communications device, determining if a user has indicated that a rendering of the alert or alarm on the mobile communications device is to be suppressed, and if so, then suppressing the rendering of the alert or alarm using the override file.

In some embodiments in accordance with the present technology (Example 77), a method of running multiple apps while minimizing the effects of errors on either includes running a CGM app on a mobile device; running a bolus calculator or a medicament delivery app on the mobile device; detecting that the CGM app, and the bolus calculator or medicament delivery app, are accessing a common memory location, the common memory location not associated with a shared database; upon the detecting, shutting down the CGM app, or the bolus calculator or medicament delivery app, or causing the CGM app, or the bolus calculator or medicament delivery app, to indicate an error.

Example 78 includes the method of Example 77, further comprising configuring the CGM app and the bolus calculator or medicament delivery app to have a common user interface for rendering of data from the shared database.

Example 79 includes the method of Example 78, wherein the data from the shared database includes glucose concentration data.

Example 80 includes the method any of Examples 77-79, further comprising: displaying on a display of the mobile computing device a user interface of the CGM app including a list of at least some of the preapproved software apps including the bolus calculator or a medicament delivery app on the scheme list; receiving, at the CGM app, a link instruction to establish the inter-app data communication architecture between the CGM app and the bolus calculator or a medicament delivery app, wherein the link instruction is based on a user selection of the bolus calculator or a medicament delivery app from the list; and creating a link between the CGM app and the bolus calculator or a medicament delivery app based on the inter-app data communication architecture.

Example 81 includes the method of any of Examples 77-80, further comprising: operating the CGM app in a foreground on the mobile computing device; generating a data structure to initiate a transition from the CGM app to the bolus calculator or a medicament delivery app in the foreground, the generating including (i) populating a scheme field of the data structure with a scheme id associated with the bolus calculator or a medicament delivery app from a scheme list stored with the CGM app, (ii) populating a payload field of the data structure with data and/or an identification where to access data in a shared file system accessible to the CGM app and the bolus calculator or a medicament delivery app, and (iii) encrypting at least the payload field of the data structure; providing the data structure to cause initiation of the bolus calculator or a medicament delivery app to the foreground; and providing at least the encrypted payload field of the data structure for the bolus calculator or a medicament delivery app.

Example 82 includes the method of any of Examples 77-81, further comprising: receiving, by the CGM app or by the bolus calculator or a medicament delivery app, a first instruction to transition to the other of the CGM app or by the bolus calculator or a medicament delivery app; generating a data structure to initiate the transition and provide a data payload to the other app; and providing, by the CGM app or by the bolus calculator or a medicament delivery app, the data structure to cause initiation of the other app in a foreground mode of the mobile computing device.

Example 83 includes the method of any of Examples 77-82, wherein the mobile computing device includes a smartphone, a tablet, or a wearable electronics device including a smartwatch or a smartglasses.

In some embodiments in accordance with the present technology (Example 84), a method of running multiple apps while minimizing the effects of errors on either includes running a CGM app on a mobile device; running a bolus calculator or a medicament delivery app on the mobile device; detecting that the CGM app, and the bolus calculator or medicament delivery app, are experiencing crosstalk or sharing data; upon the detecting, shutting down the CGM app, or the bolus calculator or medicament delivery app, or causing the CGM app, or the bolus calculator or medicament delivery app, to indicate an error.

Example 85 includes the method of Example 84, further comprising configuring the CGM app and the bolus calculator or medicament delivery app to have a common user interface for rendering of data from the shared database.

Example 86 includes the method of Example 85, wherein the data from the shared database includes glucose concentration data.

Example 87 includes the method of any of Examples 84-86, further comprising: displaying on a display of the mobile computing device a user interface of the CGM app including a list of at least some of the preapproved software apps including the bolus calculator or a medicament delivery app on the scheme list; receiving, at the CGM app, a link instruction to establish the inter-app data communication architecture between the CGM app and the bolus calculator or a medicament delivery app, wherein the link instruction is based on a user selection of the bolus calculator or a medicament delivery app from the list; and creating a link between the CGM app and the bolus calculator or a medicament delivery app based on the inter-app data communication architecture.

Example 88 includes the method of any of Examples 84-87, further comprising: operating the CGM app in a foreground on the mobile computing device; generating a data structure to initiate a transition from the CGM app to the bolus calculator or a medicament delivery app in the foreground, the generating including (i) populating a scheme field of the data structure with a scheme id associated with the bolus calculator or a medicament delivery app from a scheme list stored with the CGM app, (ii) populating a payload field of the data structure with data and/or an identification where to access data in a shared file system accessible to the CGM app and the bolus calculator or a medicament delivery app, and (iii) encrypting at least the payload field of the data structure; providing the data structure to cause initiation of the bolus calculator or a medicament delivery app to the foreground; and providing at least the encrypted payload field of the data structure for the bolus calculator or a medicament delivery app.

Example 89 includes the method of any of Examples 84-88, further comprising: receiving, by the CGM app or by the bolus calculator or a medicament delivery app, a first instruction to transition to the other of the CGM app or by the bolus calculator or a medicament delivery app; generating a data structure to initiate the transition and provide a data payload to the other app; and providing, by the CGM app or by the bolus calculator or a medicament delivery app, the data structure to cause initiation of the other app in a foreground mode of the mobile computing device.

Example 90 includes the method of any of Examples 84-89, wherein the mobile computing device includes a smartphone, a tablet, or a wearable electronics device including a smartwatch or a smartglasses.

In further aspects and embodiments, the above method features of the various aspects are formulated in terms of a system as in various aspects. Any of the features of an embodiment of any of the examples or aspects, including but not limited to any embodiments of the examples and aspects referred to above, is applicable to all other aspects and embodiments identified herein, including but not limited to any embodiments of any of the examples and aspects referred to above. Moreover, any of the features of an embodiment of the various aspects, including but not limited to any embodiments of any of the examples and aspects referred to above, is independently combinable, partly or wholly with other embodiments described herein in any way, e.g., one, two, or three or more embodiments may be combinable in whole or in part. Further, any of the features of an embodiment of the various aspects, including but not limited to any embodiments of any of the examples and aspects referred to above, may be made optional to other aspects or embodiments. Any aspect or embodiment of a method can be performed by a system or apparatus of another aspect or embodiment, and any aspect or embodiment of a system or apparatus can be configured to perform a method of another aspect or embodiment, including but not limited to any embodiments of any of the examples and aspects referred to above.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A mobile communications device, comprising:
a memory comprising a first software module and a second software module;
a processor in data communication with the memory and configured to:
receive, via the first software module, glucose measurements from a glucose monitoring system;
determine, via the second software module, an insulin dosage based on the received glucose measurements, wherein:
the first and second software modules are different software modules,
the second software module is operable to receive patient specific input data and calculate the insulin dosage based on the patient specific input data and the received glucose measurements, and
the second software module is a plug-in for a software application comprising the first software module; and
transmit a command indicative of the determined insulin dosage to an insulin delivery device to cause the insulin delivery device to administer the insulin dosage to a patient.

2. The mobile communications device of claim 1, wherein the processor is configured to transmit the command via the second software module.

3. The mobile communications device of claim 1, wherein the processor is further configured to store, via the first software module, the glucose measurements in a shared database.

4. The mobile communications device of claim 3, wherein the processor is further configured to retrieve, via the second software module, the glucose measurements stored in the shared database.

5. The mobile communications device of claim 1, wherein:
the memory further comprises a third software module, wherein the first software module, the second software module, and the third software module are different software modules; and
the processor is configured to transmit the command via the third software module.

6. The mobile communications device of claim 5, wherein the processor is further configured to:
store, via the second software module, the determined insulin dosage; and
retrieve, via the third software module, the determined insulin dosage.

7. The mobile communications device of claim 1, wherein the processor is further configured to:
generate, via the first software module, a symmetric database key for encryption of a shared database;
encrypt, via the first software module, information in the shared database using the symmetric database key;
create, via the first software module, an encrypted symmetric database key by encrypting a copy of the symmetric database key;
decrypt, via the second software module, the encrypted symmetric database key to obtain the copy of the symmetric database key; and
access, via the second software module, the information in the shared database using the copy of the symmetric database key.

8. The mobile communications device of claim 7, wherein:
the copy of the symmetric database key is encrypted using a public key of the second software module; and
the encrypted symmetric database key is decrypted using a private key of the second software module.

9. The mobile communications device of claim 1, wherein the first software module and the second software module communicate using an inter-application communications architecture.

10. The mobile communications device of claim 9, wherein the inter-application communications architecture comprises a shared file system.

11. The mobile communications device of claim 9, wherein the inter-application communications architecture comprises a shared database.

12. A method for use by a mobile communications device operable to execute a first software module and a second software module, the method comprising:
- receiving, via the first software module, glucose measurements from a glucose monitoring system;
- determining, via the second software module, an insulin dosage based on the received glucose measurements, wherein:
  - the first and second software modules are different software modules,
  - the second software module is operable to receive patient specific input data and calculate the insulin dosage based on the patient specific input data and the received glucose measurements, and
  - the second software module is a plug-in for a software application comprising the first software module; and
- transmitting a command indicative of the determined insulin dosage to an insulin delivery device to cause the insulin delivery device to administer the insulin dosage to a patient.

13. The method of claim 12, wherein the transmitting is performed via the second software module.

14. The method of claim 12, further comprising storing, via the first software module, the glucose measurements in a shared database.

15. The method of claim 14, further comprising retrieving, via the second software module, the glucose measurements stored in the shared database.

16. A non-transitory computer readable medium comprising instructions that, when executed by a processor, causes the processor to perform a method comprising:
- receiving, via a first software module, glucose measurements from a glucose monitoring system;
- determining, via a second software module, an insulin dosage based on the received glucose measurements, wherein:
  - the first and second software modules are different software modules,
  - the second software module is operable to receive patient specific input data and calculate the insulin dosage based on the patient specific input data and the received glucose measurements, and
  - the second software module is a plug-in for a software application comprising the first software module; and
- transmitting a command indicative of the determined insulin dosage to an insulin delivery device to cause the insulin delivery device to administer the insulin dosage to a patient.

* * * * *